(12) United States Patent
Malcuit et al.

(10) Patent No.: US 9,982,270 B2
(45) Date of Patent: *May 29, 2018

(54) ORGANIC COMPOUNDS

(75) Inventors: Isabelle Malcuit, Norwich (GB); Alexander Sorokin, Norwich (GB)

(73) Assignee: Algentech SAS, Envry (FR)

( * ) Notice: Subject to any disclaimer, the term of this patent is extended or adjusted under 35 U.S.C. 154(b) by 470 days.

This patent is subject to a terminal disclaimer.

(21) Appl. No.: 12/601,384

(22) PCT Filed: May 22, 2008

(86) PCT No.: PCT/GB2008/001741
§ 371 (c)(1),
(2), (4) Date: Mar. 16, 2010

(87) PCT Pub. No.: WO2008/142411
PCT Pub. Date: Nov. 27, 2008

(65) Prior Publication Data
US 2010/0186120 A1    Jul. 22, 2010

(30) Foreign Application Priority Data

May 23, 2007 (GB) .................................. 0709886.6

(51) Int. Cl.
*C12N 15/09* (2006.01)
*C12N 15/11* (2006.01)
*C12N 15/63* (2006.01)
*C12N 15/62* (2006.01)
*C12N 15/82* (2006.01)

(52) U.S. Cl.
CPC ................................ *C12N 15/8214* (2013.01)

(58) Field of Classification Search
None
See application file for complete search history.

(56) References Cited

U.S. PATENT DOCUMENTS

| 2,561,330 A | * | 7/1951 | Ayers ........................... 554/198 |
| 9,567,598 B2 | * | 2/2017 | Malcuit ............. C12N 15/8214 |
| 2003/0104352 A1 | * | 6/2003 | Lambowitz et al. ............. 435/4 |
| 2009/0142838 A1 | * | 6/2009 | Cui et al. ...................... 435/455 |

OTHER PUBLICATIONS

Blythe et al, 2004, Mol. Biochem. Parasitol. 134:11-15.*
Byers et al, 2007, Biochem Cell. Biol. 85:649-662.*
Lambowitz et al, p. 6, left column, paragraph 2.*
Nielsen et al, 2009, RNA Biology 6:4 375-383.*
Deshpande et al (Curr Genet. Jul. 1995; 28(2): 122-7).*
Ostersetzer et al (Plant Cell. Jan. 2005; 17(1): 241-255).*
Ralph Bock et al., "Correct Splicing of a Group II Intron From a Chimeric Reporter Gene Transcript in Tobacco Plastids", Nucleic Acids Research, 1995, pp. 2544-2547, vol. 23, No. 13.
Obed W. Odom et al., "Mobile Self-Splicing Group I Introns from the psbA Gene of Chlamydomonas Reinhardtii: Highly Efficient Homing of an Exogenous Intron Containing Its Own Promoter", Molecular and Cellular Biology, May 2001, pp. 3472-3481, vol. 21, No. 10.
Georg Mohr and Alan M. Lambowitz, Putative Proteins Related to Group II Intron Reverse Transcriptase/Maturases are Encoded by Nuclear Genes in Higher Plants, Nucleic Acids Research, 2003, vol. 31, No. 2, pp. 647-652.
Reimo Zoschke, et al., An Organellar Maturase Associates With Multiple Group II Introns, Institute of Biology, PNAS, Feb. 16, 2010, vol. 107, No. 7, pp. 3245-3250.

* cited by examiner

*Primary Examiner* — Stephen Uyeno
(74) *Attorney, Agent, or Firm* — Sughrue Mion, PLLC

(57) ABSTRACT

Method for heterologous protein production in plant cell plastids comprising introducing into plant cells nucleic acid components that encode heterologous proteins under the control of promoters operative in plastids, vectors, host cells, plants and uses thereof.

18 Claims, 11 Drawing Sheets

ORGANIC COMPOUNDS

CROSS REFERENCE TO RELATED APPLICATION

Figure 1A:
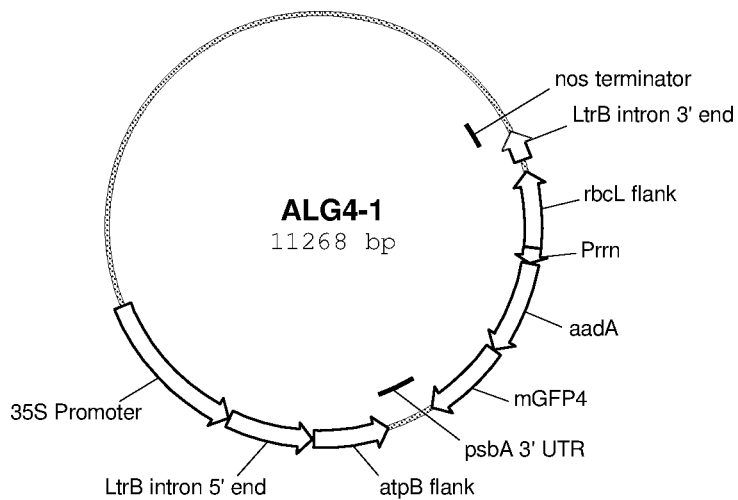

This application is a National Stage of International Application No. PCT/GB2008/001741 filed May 22, 2008, claiming priority based on United Kingdom Patent Application No. GB 0709886.6, filed May 23, 2007, the contents of all of which are incorporated herein by reference in their entirety.

The present invention relates to a method for producing heterologous or exogenous proteins in plant cell material such as transformed plant cells in culture or in plant tissue derived from transformed plant cells. In particular, the method relates to a method for producing proteins in plastids comprised in plant cell material, the genetic material required therefor, such as DNA and RNA, vectors, host cells, methods of introduction of genetic material into plant cells, and uses thereof.

A US Patent application to Biesgen C. (publication number 2006/0253916) relates to methods for the generation of transgenic plants possessing genetically modified plastids. The technical teaching behind the methods described therein does not rely on the use of an intron-derived RNA vehicle that makes use of endogenous cellular processes for the transfer of RNA from the cytoplasm of the cell into the plastid.

A disadvantage of prior art plastid transformation methods is that the transformation efficiency in terms of numbers of transformed plastids per cell tends to be low, and hence the amount of exogenous protein produced per cell tends also to be low. A further disadvantage of prior art methods is that the delivery of genetic information into the plastid is patchy. Prior art methods do not rely on endogenous cellular processes for transfer of RNA into the plastid genome, and as such, prior art processes for genetically modifying plastids are generally inefficient. These and other disadvantages of prior art plastid transformation technology will become apparent from the foregoing description.

The present inventors have found that by using or adapting endogenous cellular processes for the transfer of polynucleotides, such as RNAs, from the cytoplasm to plastids in the plant cell, polynucleotide sequences derived from nuclear transformation of the nucleus of a plant cell can be efficiently transferred to the plastid genome, within a plant cell that is so transformed, and expressed in the plastid of interest as described herein. For the purposes of the present invention the terms "plastid" and "plastids" and "plastid population" are used interchangeably, unless context demands otherwise. Also, for the purposes of the present invention the terms "plant cell" and "plant cells" are used interchangeably, unless context demands otherwise. By employing or adapting endogenous cellular processes for the transfer of RNA to the plastid genome as described herein, the method of the invention is considered to be unique over prior art methods for the generation of plants possessing genetically modified plastids: the plastid population of the cell or of cells comprising plant tissue transformed according to the present invention is constantly bombarded by RNA that is derived from the nucleus of the cell, which is carried over from the plastid membrane and into the plastid genome where it is reverse transcribed, integrated and then expressed, resulting in the generation of proteins of interest.

There exists a need for an alternative plastid transformation method for the transformation of plant cells over those of the prior art.

The basis for the present invention, which does not appear to have been realised in the prior art, is to insert at least one polynucleotide sequence of interest into a suitable site of a domain of an intron, or into suitable sites within the domains of several introns, of either bacterial or plastid origin, or of both bacterial and plastid origin, such as a group I intron or a group II intron, and to engineer the insertion of the modified intron into the nucleus of a plant host cell where it is expressed as RNA. The nucleotide sequence of introns of interest in the invention may be further modified to eliminate cryptic splicing sites, thus improving expression in the plant cell. The expressed RNA is then transferred to the cytoplasm where it binds with a multifunctional protein that carries it over to the membrane of the plastid, where the RNA sequence is reverse transcribed into DNA which then inserts into the plastid genome where the polynucleotide sequence of interest under the control of a plastid specific promoter is then expressed, giving rise to a polypeptide or of polypeptides of interest, depending on design.

The present invention also relates to the production of transgenic plant cells and transgenic plants comprising plastids that are genetically modified with intron-derived polynucleotide sequences carrying polynucleotide sequences of interest under operational control of a plant plastid promoter.

According to the present invention there is provided a method of producing at least a heterologous or exogenous polypeptide in a plant cell that comprises:

1) introducing into the said plant cell a plant nuclear promoter that drives expression in a plant nucleus operably linked to an intron that comprises a first isolated nucleic acid sequence wherein the said first isolated nucleic acid sequence comprises a plant plastid promoter that drives expression in a plant plastid operably linked to a second nucleic acid sequence that encodes at least an heterologous or exogenous polypeptide;
2) growing said plant cell of (1) under conditions wherein said plant nuclear promoter drives expression of said intron;
3) selecting a plant cell of (2) wherein said first isolated nucleic acid sequence is integrated into the plastid genome;
4) growing the plant cell of (3) under conditions wherein said plant plastid promoter expresses said heterologous or exogenous protein from said second nucleic acid sequence therefrom.

In a further embodiment of the invention there is provided a method of producing at least a heterologous or exogenous polypeptide in a plant that comprises:

1) introducing into a regenerable plant cell a plant nuclear promoter that drives expression in a plant nucleus operably linked to an intron that comprises a first isolated nucleic acid sequence wherein the said first isolated nucleic acid sequence comprises a plant plastid promoter that drives expression in a plant plastid operably linked to a second nucleic acid sequence that encodes at least an heterologous or exogenous polypeptide;
2) growing said plant cell of (1) under conditions wherein said plant nuclear promoter drives expression of said intron;
3) selecting a plant cell of (2) wherein said first isolated nucleic acid sequence is integrated into the plastid genome;

4) regenerating a plant from the plant cell of (3); and
5) growing the plant of (4) under conditions wherein said plant plastid promoter expresses said heterologous or exogenous protein from said second nucleic acid sequence therefrom.

The intron of 1) is derived from a bacterium, a fungus or a plastid from a plant and may be selected or derived from group I and group II introns or modified versions thereof in which cryptic splicing sites have been eliminated. Preferably, the intron is a group II intron, such as the *Lactococcus lactis* Ll.ltrB intron or a modified version of it in which cryptic splicing sites have been eliminated as outlined herein. Group II introns are widely represented in the organelles of plants (eg 25 introns in the tobacco plastid genome) and fungi, and in bacteria. Group II introns useful in the method of the invention are mobile, highly structural retroelements that encode multifunctional protein (intron encoded protein or IEP) which possesses reverse transcriptase (RT) activity. The IEP facilitates splicing of intron RNA by stabilization of the catalytically active RNA structure, performs reverse transcription and insertion of the intron into specific DNA target sites of the bacterial genome at high frequency (Moran et al. (1995) Mol Cell Biol 15:2828-2838; Cousineau et al. (1998) Cell 94:451-462).

Group II introns of bacterial origin, such as those derived from *Lactococcus* that comprise a modified LtrA gene, are preferably used in the method of the invention. The LtrA polynucleotide sequence of a *Lactococcus* bacterium, such as *Lactococcus lactis* may be modified for optimum expression in plants by inserting into it at least one polynucleotide sequence comprising one or more introns from at least one plant nucleic acid sequence, such as from one or more plant genes and by substituting certain selected codons having a low frequency of usage in native plants with codons that occur with a higher frequency in such plants. Typically, the bacterial LtrA sequence of interest is analysed with reference to plant codon usage using in silico comparisons such as those found at the website www.kazusa.or.jp/codon for bacterial codons that occur with low frequency in plants. Such codons may then be substituted with codons that have a high frequency of occurrence in plants, and an in silico-derived modified polynucleotide sequence is generated. From this optimised LtrA sequence a synthetic LtrA polynucleotide sequence corresponding to the in silico generated sequence is made using standard polynucleotide synthesis procedures known in the art, and may then be used in the preparation of constructs of use in the present invention as outlined herein. It is thought that by using a modified sequence that comprises plant codon substitutions as outlined above more plant cell environment stable polynucleotide RNA sequences are generated.

Other introns that may be used in the method of the invention are those which naturally occur in the plastids of higher plants, especially group II introns, such as in the trnK genes of the plastid genome. Suitable trnk introns are found in plastids of *Arabidopsis*, maize and tobacco.

Other types of introns that may be used in the method of the invention include, for example, the group I intron from Tetrahymena (GenBank Acc. No.: X54512; Kruger K et al. (1982) Cell 31:147-157; Roman J and Woodson S A (1998) Proc Natl Acad Sci USA 95:2134-2139), the group II rIl intron from Scenedesmus obliquus (GenBank Acc. No.: X17375.2 nucleotides 28831 to 29438; Hollander V and Kuck U (1999) Nucl Acids Res 27: 2339-2344; Herdenberger F et al. (1994) Nucl Acids Res 22: 2869-2875; Kuck U et al. (1990) Nucl Acids Res 18:2691-2697), the Ll.LtrB intron (GenBank Acc. No.: U50902 nucleotides 2854 to 5345), the *Arabidopsis* trnK intron (GenBank Acc. No.: AP000423, complementary nucleotides 1752 to 4310) [0222], the maize trnK intron (GenBank Acc. No.: X86563, complementary nucleotides 1421 to 3909), and the tobacco trnK intron (GenBank Acc. No.: Z00044, complementary nucleotides 1752 to 4310).

Aside from heterologous introns described herein, endogenous introns that occur naturally in the plastids of the plant cells of the plant of interest may be used in the method of the invention. However, it is thought that heterologous introns, such as trnk introns, are preferred since they may be used to avoid potential instabilities brought about by sequence duplication. Introns which occur naturally in the plastids of the plant of interest may be modified such that they have a sequence homology of about 50%, 60%, 70%, 75%, 80%, 85%, 90% or 95%, or of any percentage sequence homology therebetween, with the sequence of the starting intron, while retaining functionality, may also be employed in the method of the invention.

A plant nuclear promoter (for example, an exogenous nucleus specific promoter) is one that denotes a promoter that is introduced in front of a nucleic acid sequence of interest and is operably associated therewith. Thus a plant nuclear promoter is one that has been placed in front of a selected polynucleotide component, such as an introduced group I or group II intron. Thus a promoter may be native to a plant cell of interest but may not be operably associated with the group I or group II intron of the invention in a wild-type plant cell. Typically, a plant nuclear promoter, such as an exogenous nucleus specific promoter, is one that is transferred to a host cell or host plant from a source other than the host cell or host plant.

The cDNA's encoding a polynucleotide of the invention, such as a group I or a group II intron, contain at least one type of promoter that is operable in a plant cell, for example, an inducible or a constitutive promoter operatively linked to a first and/or second nucleic acid sequence or nucleic acid sequence component as herein defined and as provided by the present invention. As discussed, this enables control of expression of the polynucleotide of the invention. The invention also provides plants transformed with polynucleotide sequences or constructs and methods including introduction of such polynucleotide nucleic acid sequences or constructs into a plant cell and/or induction of expression of said first or second nucleic acid sequence or construct within a plant cell, e.g. by application of a suitable stimulus, such as an effective exogenous inducer.

The term "inducible" as applied to a promoter is well understood by those skilled in the art. In essence, expression under the control of an inducible promoter is "switched on" or increased in response to an applied stimulus (which may be generated within a cell or provided exogenously). The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level, which brings about the desired phenotype. One example of an inducible promoter is the ethanol inducible gene switch disclosed in Caddick et al (1998) Nature Biotechnology 16: 177-180. A number of inducible promoters are known in the art.

Chemically regulated promoters can be used to modulate the expression of a gene or a polynucleotide sequence of the invention in a plant through the application of an exogenous chemical regulator. Depending upon the objective, the promoter may be a chemically inducible promoter, where application of the chemical induces gene expression, or a chemical-repressible promoter, where application of the chemical represses gene expression. Chemically inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemically regulated promoters of interest include steroid-responsive promoters (see, for example, the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991) *Mol. Gen. Genet.* 227:229-237, and U.S. Pat. Nos. 5,814,618 and 5,789,156), herein incorporated by reference.

Where enhanced expression in particular tissues is desired, tissue-specific promoters can be utilized. Tissue-specific promoters include those described by Yamamoto et al. (1997) *Plant J.* 12(2)255-265; Kawamata et al. (1997) *Plant Cell Physiol.* 38(7):792-803; Hansen et al. (1997) *Mol. Gen Genet.* 254(3):337-343; Russell et al. (1997) *Transgenic Res.* 6(2):157-168; Rinehart et al. (1996) *Plant Physiol.* 112(3):1331-1341; Van Camp et al. (1996) *Plant Physiol.* 112(2):525-535; Canevascini et al. (1996) *Plant Physiol.* 112(2):513-524; Yamamoto et al. (1994) *Plant Cell Physiol.* 35(5):773-778; Lam (1994) *Results Probl. Cell Differ.* 20:181-196; Orozco et al. (1993) *Plant Mol Biol.* 23(6): 1129-1138; Matsuoka et al. (1993) *Proc Natl. Acad. Sci. USA* 90(20):9586-9590; and Guevara-Garcia et al. (1993) *Plant J.* 4(3):495-505.

So-called constitutive promoters may also be used in the methods of the present invention. Constitutive promoters include, for example, CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. application Ser. No. 08/409,297), and the like. Other constitutive promoters include those in U.S. Pat. Nos. 5,608,149; 5,608, 144; 5,604,121; 5,569,597; 5,466,785; 5,399,680; 5,268, 463; and 5,608,142.

The expression in plastids is effected by employing a plant plastid promoter such as plastid specific promoters and/or transcription regulation elements. Examples include the RNA polymerase promoter (WO 97/06250) and other promoters described in the art, eg in WO 00/07431, U.S. Pat. No. 5,877,402, WO 97/06250, WO 98/55595, WO 99/46394, WO 01/42441 and WO 01/07590; the rpo B promoter element, the atpB promoter element, the clpP promoter element (see also WO 99/46394) and the 16S rDNA promoter element. The plastid specific promoter may also have a polycistronic "operon" assigned to it (EP-A 1 076 095; WO 00/20611).

Further promoters that may be used in the method of the invention also include the PrbcL promoter, the Prps16 promoter, and the Prrn16 promoter described in US Patent application 2006/0253916, the plastid specific promoters Prrn-62, Pycf2-1577, PatpB-289, Prps2-152, Prps16-107, Pycf1-41, PatpI-207, PclpP-511, PclpP-173 and PaccD-129 (WO 97/06250; Hajdukiewicz P T J et al. (1997) EMBO J 16:4041-4048), the PaccD-129 promoter of the tobacco accD gene (WO 97/06250), the PclpP-53 promoter of the clpP gene as highly active NEP promoter in chloroplasts (WO 97/06250), the Prrn-62 promoter of the rrn gene, the Prps16-107 promoter of the rps16 gene, the PatpB/E-290 promoter of the tobacco atpB/E gene (Kapoor S et al. (1997) Plant J 11:327-337), and the PrpoB-345 promoter of the rpoB gene (Liere K & Maliga P (1999) EMBO J 18: 249-257). Furthermore, all those promoters which belong to class III (Hajdukiewicz P T J et al. (1997) EMBO J 16:4041-4048) and all fragments of the class II promoters which control the initiation of transcription by NEP may be utilized in the method of the invention. Such promoters or promoter moieties are not generally known to be highly conserved. ATAGAATAAA is given as consensus near the transcription initiation site of NEP promoters (Hajdukiewicz P T J et al (1997) EMBO J 16:4041-4048).

Naturally, the man skilled in the art will appreciate that terminator DNA sequences will be present in constructs used in the invention. A terminator is contemplated as a DNA sequence at the end of a transcriptional unit which signals termination of transcription. These elements are 3'-non-translated sequences containing polyadenylation signals, which act to cause the addition of polyadenylate sequences to the 3' end of primary transcripts. For expression in plant cells the nopaline synthase transcriptional terminator (A. Depicker et al., 1982, J. of Mol. & Applied Gen. 1:561-573) sequence serves as a transcriptional termination signal.

Those skilled in the art are well able to construct vectors and design protocols for recombinant nucleic acid sequences or gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992. The disclosures of Sambrook et al. and Ausubel et al. are incorporated herein by reference. Specific procedures and vectors previously used with wide success upon plants are described by Bevan (Nucl. Acids Res. 12, 8711-8721 (1984)) and Guerineau and Mullineaux (1993) (Plant transformation and expression vectors. In: Plant Molecular Biology Labfax (Croy RRD ed.) Oxford, BIOS Scientific Publishers, pp 121-148).

Naturally, the skilled addressee will appreciate that each introduced group I and/or group II intron will be under regulatory control of its own exogenous promoter and terminator. When two or more target proteins are destined to be produced from a single carrier RNA it is preferable if they are able to be readily separated, for example by binding to different protein-specific antibodies (monoclonal or polyclonal) in the harvesting phase of the plant cell culture system.

Selectable genetic markers may facilitate the selection of transgenic plants and these may consist of chimaeric genes that confer selectable phenotypes such as resistance to antibiotics such as spectinomycin, streptomycin, kanamycin, neomycin, hygromycin, puramycin, phosphinotricin, chlorsulfuron, methotrexate, gentamycin, spectinomycin, imidazolinones and glyphosate.

When introducing selected nucleic acid sequences according to the present invention into a cell, certain considerations must be taken into account, well known to those skilled in the art. The nucleic acid to be inserted should be assembled within a construct, which contains effective regulatory elements, which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with DNA segments containing sequences of interest as provided herein may be produced by standard techniques, which are already known for the genetic manipulation of plants. DNA can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984), particle or micro projectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1-11.

Thus once a nucleic acid sequence or gene has been identified, it may be reintroduced into plant cells using techniques well known to those skilled in the art to produce transgenic plants of the appropriate phenotype.

*Agrobacterium* transformation is widely used by those skilled in the art to transform dicotyledonous species. Production of stable, fertile transgenic plants in almost all economically relevant monocot plants is also now routine: (Toriyama, et al. (1988) *Bio/Technology* 6, 1072-1074; Zhang, et al. (1988) *Plant Cell Rep.* 7, 379-384; Zhang, et al. (1988) *Theor. Appl. Genet* 76, 835-840; Shimamoto, et al. (1989) *Nature* 338, 274-276; Datta, et al. (1990) *Bio/Technology* 8, 736-740; Christou, et al. (1991) *Bio/Technology* 9, 957-962; Peng, et al. (1991) International Rice Research Institute, Manila, Philippines 563-574; Cao, et al. (1992) *Plant Cell Rep.* 11, 585-591; Li, et al. (1993) *Plant Cell Rep.* 12, 250-255; Rathore, et al. (1993) *Plant Molecular Biology* 21, 871-884; Fromm, et al. (1990) *Bio/Technology* 8, 833-839; Gordon-Kamm, et al. (1990) *Plant Cell* 2, 603-618; D'Halluin, et al. (1992) *Plant Cell* 4, 1495-1505; Walters, et al. (1992) *Plant Molecular Biology* 18, 189-200; Koziel, et al. (1993) *Biotechnology* 11, 194-200; Vasil, I. K. (1994) *Plant Molecular Biology* 25, 925-937; Weeks, et al. (1993) *Plant Physiology* 102, 1077-1084; Somers, et al. (1992) *Bio/Technology* 10, 1589-1594; WO92/14828). In particular, *Agrobacterium* mediated transformation is now a highly efficient alternative transformation method in monocots (Hiei et al. (1994) *The Plant Journal* 6, 271-282).

The generation of fertile transgenic plants has been achieved in the cereals rice, maize, wheat, oat, and barley (reviewed in Shimamoto, K. (1994) *Current Opinion in Biotechnology* 5, 158-162.; Vasil, et al. (1992) *Bio/Technology* 10, 667-674; Vain et al., 1995, *Biotechnology Advances* 13 (4): 653-671; Vasil, 1996, *Nature Biotechnology* 14 page 702). Wan and Lemaux (1994) *Plant Physiol.* 104: 37-48 describe techniques for generation of large numbers of independently transformed fertile barley plants.

Micro projectile bombardment, electroporation and direct DNA uptake are preferred where *Agrobacterium* is inefficient or ineffective. Alternatively, a combination of different techniques may be employed to enhance the efficiency of the transformation process, e.g. bombardment with *Agrobacterium* coated micro particles (EP-A-486234) or micro projectile bombardment to induce wounding followed by co-cultivation with *Agrobacterium* (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol. I, II and III, Laboratory Procedures and Their Applications*, Academic Press, 1984, and Weiss Bach and Weiss Bach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

The invention further encompasses a host cell transformed with vectors or constructs as set forth above, especially a plant or a microbial cell. Thus, a host cell, such as a plant cell, including nucleotide sequences of the invention as herein indicated is provided. Within the cell, the nucleotide sequence may be incorporated within the chromosome.

Also according to the invention there is provided a plant cell having incorporated into its genome at least a nucleotide sequence, particularly heterologous nucleotide sequences, as provided by the present invention under operative control of regulatory sequences for control of expression as herein described. The coding sequence may be operably linked to one or more regulatory sequences which may be heterologous or foreign to the nucleic acid sequences employed in the invention, such as those not naturally associated with the nucleic acid sequence(s) for its (their) expression. The nucleotide sequence according to the invention may be placed under the control of an externally inducible promoter to place expression under the control of the user. A further aspect of the present invention provides a method of making such a plant cell involving introduction of nucleic acid sequence(s) contemplated for use in the invention or a suitable vector including the sequence(s) contemplated for use in the invention into a plant cell and causing or allowing recombination between the vector and the plant cell genome to introduce the said sequences into the genome. The invention extends to plant cells containing a nucleotide sequence according to the invention as a result of introduction of the nucleotide sequence into an ancestor cell.

The term "heterologous" may be used to indicate that the gene/sequence of nucleotides in question have been introduced into said cells of the plant or an ancestor thereof, using genetic engineering, ie by human intervention. A transgenic plant cell, i.e. transgenic for the nucleotide sequence in question, may be provided. The transgene may be on an extra-genomic vector or incorporated, preferably stably, into the genome. A heterologous gene may replace an endogenous equivalent gene, ie one that normally performs the same or a similar function, or the inserted sequence may be additional to the endogenous gene or other sequence. An advantage of introduction of a heterologous gene is the ability to place expression of a sequence under the control of a promoter of choice, in order to be able to influence expression according to preference. Furthermore, mutants, variants and derivatives of the wild-type gene, e.g. with higher activity than wild type, may be used in place of the endogenous gene. Nucleotide sequences heterologous, or exogenous or foreign, to a plant cell may be non-naturally occurring in cells of that type, variety or species. Thus, a nucleotide sequence may include a coding sequence of or derived from a particular type of plant cell or species or variety of plant, placed within the context of a plant cell of a different type or species or variety of plant. A further possibility is for a nucleotide sequence to be placed within a cell in which it or a homologue is found naturally, but wherein the nucleotide sequence is linked and/or adjacent to nucleic acid which does not occur naturally within the cell, or cells of that type or species or variety of plant, such as operably linked to one or more regulatory sequences, such as a promoter sequence, for control of expression. A sequence within a plant or other host cell may be identifiably heterologous, exogenous or foreign.

Plants which include a plant cell according to the invention are also provided, along with any part or propagule thereof, seed, selfed or hybrid progeny and descendants. Particularly provided are transgenic crop plants, which have been engineered to carry genes identified as stated above. Examples of suitable plants include tobacco (*Nicotiana tabacum*) and other *Nicotiana* species, carrot, vegetable and oilseed *Brassica's*, melons, Capsicums, grape vines, lettuce, strawberry, sugar beet, wheat, barley, (corn) maize, rice, soybean, peas, sorghum, sunflower, tomato, cotton, and potato. Especially preferred transgenic plants of the invention include cotton, rice, oilseed *Brassica* species such as canola, corn (maize) and soybean.

In addition to a plant, the present invention provides any clone of such a plant, seed, selfed or hybrid progeny and descendants, and any part of any of these, such as cuttings, seed. The invention provides any plant propagule,that is any part which may be used in reproduction or propagation, sexual or asexual, including cuttings, seed and so on. Also encompassed by the invention is a plant which is a sexually or asexually propagated offspring, clone or descendant of such a plant, or any part or propagule of said plant, offspring, clone or descendant.

The present invention also encompasses the polypeptide expression product of a nucleic acid molecule according to the invention as disclosed herein or obtainable in accordance with the information and suggestions herein. Also provided are methods of making such an expression product by expression from a nucleotide sequence encoding therefore under suitable conditions in suitable host cells e.g. *E. coli*. Those skilled in the art are well able to construct vectors and design protocols and systems for expression and recovery of products of recombinant gene expression.

The heterologous or exogenous target protein is contemplated to be any protein of interest that may be produced by the method of the invention. Types of target proteins that are contemplated for production in a method of the present invention include plant proteins and pharmaceutical proteins for use in mammals, including man, such as insulin, pre-proinsulin, proinsulin, glucagon, interferons such as α-interferon, β-interferon, γ-interferon, blood-clotting factors selected from Factor VII, VIII, IX, X, XI, and XII, fertility hormones including luteinising hormone, follicle stimulating hormone growth factors including epidermal growth factor, platelet-derived growth factor, granulocyte colony stimulating factor and the like, prolactin, oxytocin, thyroid stimulating hormone, adrenocorticotropic hormone, calcitonin, parathyroid hormone, somatostatin, erythropoietin (EPO), enzymes such as β-glucocerebrosidase, haemoglobin, serum albumin, collagen, insect toxic protein from *Bacillus thuringiensis*; herbicide resistance protein (glyphosate); salt-tolerance proteins; nutritional enhancement proteins involved in the biosynthesis of phenolics, starches, sugars, alkaloids, vitamins,and edible vaccines, and the like. Furthermore, the method of the invention can be used for the production of specific monoclonal antibodies or active fragments thereof and of industrial enzymes.

All proteins mentioned hereinabove are of the plant and human type. Other proteins that are contemplated for production in the present invention include proteins for use in veterinary care and may correspond to animal homologues of human proteins, such as the human proteins mentioned hereinabove.

A polypeptide according to the present invention may be an allele, variant, fragment, derivative, mutant or homologue of the(a) polypeptides as mentioned herein. The allele, variant, fragment, derivative, mutant or homologue may have substantially the same function of the polypeptides alluded to above and as shown herein or may be a functional mutant thereof.

"Homology" in relation to an amino acid sequence or polypeptide sequence produced by the method of the invention may be used to refer to identity or similarity, preferably identity. As noted already above, high level of amino acid identity may be limited to functionally significant domains or regions.

In certain embodiments, an allele, variant, derivative, mutant derivative, mutant or homologue of the specific sequence may show little overall homology, say about 20%, or about 25%, or about 30%, or about 35%, or about 40% or about 45%, with the specific sequence. However, in functionally significant domains or regions, the amino acid homology may be much higher. Putative functionally significant domains or regions can be identified using processes of bioinformatics, including comparison of the sequences of homologues.

Functionally significant domains or regions of different polypeptides may be combined for expression from encoding nucleic acid as a fusion protein. For example, particularly advantageous or desirable properties of different homologues may be combined in a hybrid protein, such that the resultant expression product, may include fragments of various parent proteins, if appropriate.

Similarity of amino acid sequences may be as defined and determined by the TBLASTN program, of Altschul et al. (1990) *J. Mol. Biol.* 215: 403-10, which is in standard use in the art. In particular, TBLASTN 2.0 may be used with Matrix BLOSUM62 and GAP penalties: existence: 11, extension: 1. Another standard program that may be used is BestFit, which is part of the Wisconsin Package, Version 8, September 1994, (Genetics Computer Group, 575 Science Drive, Madison, Wis., USA, Wisconsin 53711). BestFit makes an optimal alignment of the best segment of similarity between two sequences. Optimal alignments are found by inserting gaps to maximize the number of matches using the local homology algorithm of Smith and Waterman (*Adv. Appl. Math.* (1981) 2: 482-489). Other algorithms include GAP, which uses the Needleman and Wunsch algorithm to align two complete sequences that maximizes the number of matches and minimizes the number of gaps. As with any algorithm, generally the default parameters are used, which for GAP are a gap creation penalty=12 and gap extension penalty=4. Alternatively, a gap creation penalty of 3 and gap extension penalty of 0.1 may be used. The algorithm FASTA (which uses the method of Pearson and Lipman (1988) *PNAS USA* 85: 2444-2448) is a further alternative.

Use of either of the terms "homology" and "homologous" herein does not imply any necessary evolutionary relationship between compared sequences, in keeping for example with standard use of terms such as "homologous recombination" which merely requires that two nucleotide sequences are sufficiently similar to recombine under the appropriate conditions. Further discussion of polypeptides according to the present invention, which may be encoded by nucleic acid according to the present invention, is found below.

The teaching of all references cited herein is incorporated in its entirety into the present description.

There now follow non-limiting examples and figures illustrating the invention.

Figure 1B:
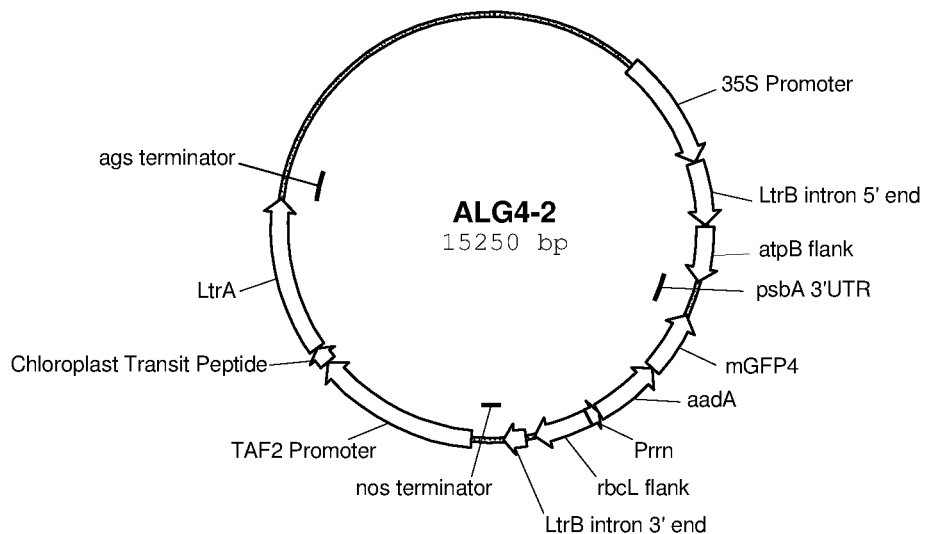
Figure 1C:
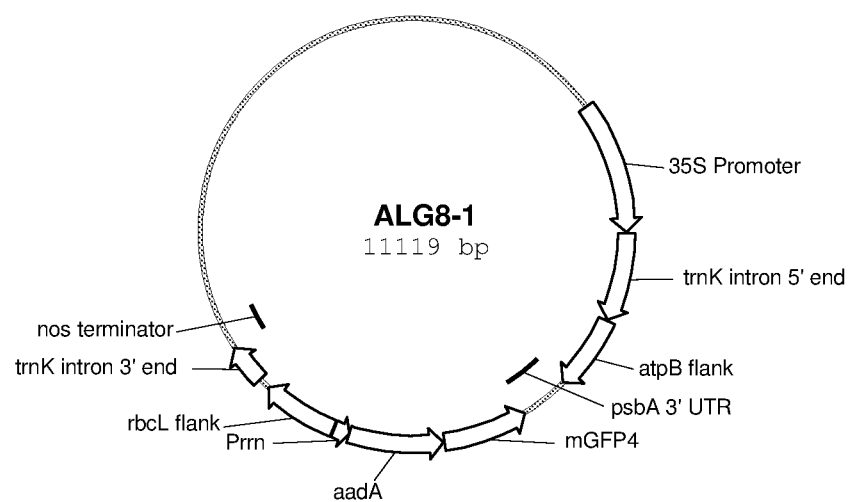
Figure 2A:
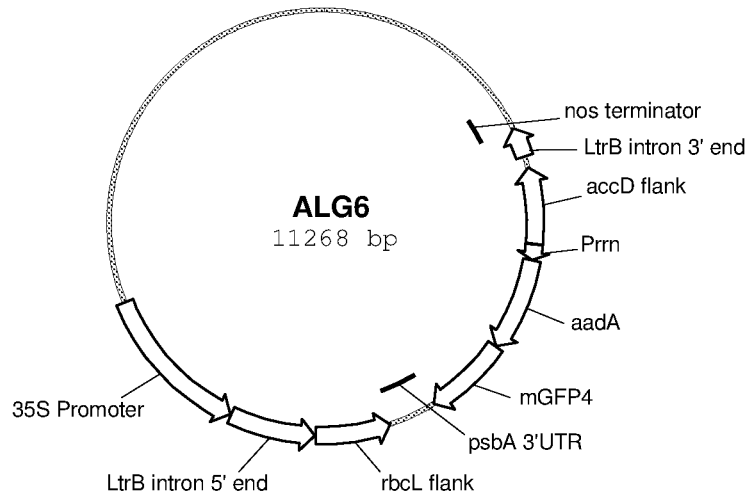
Figure 2B:
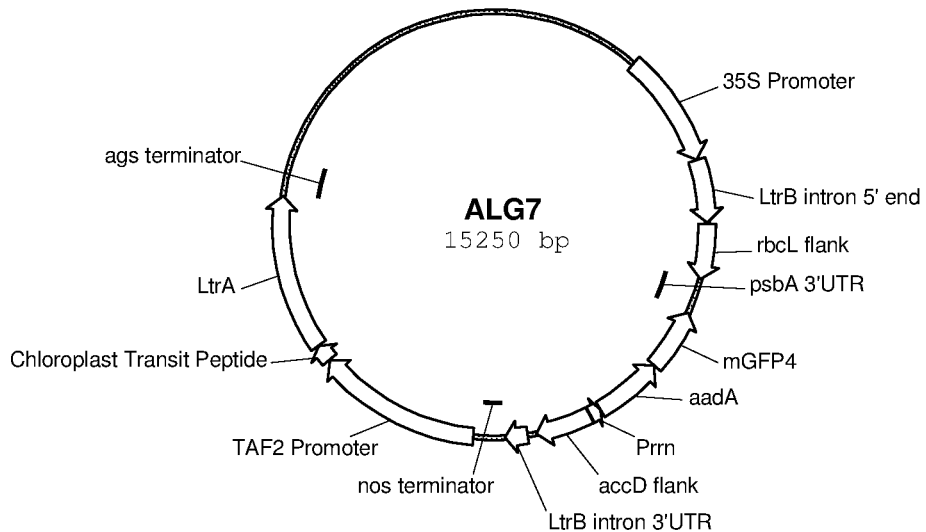
Figure 2C:
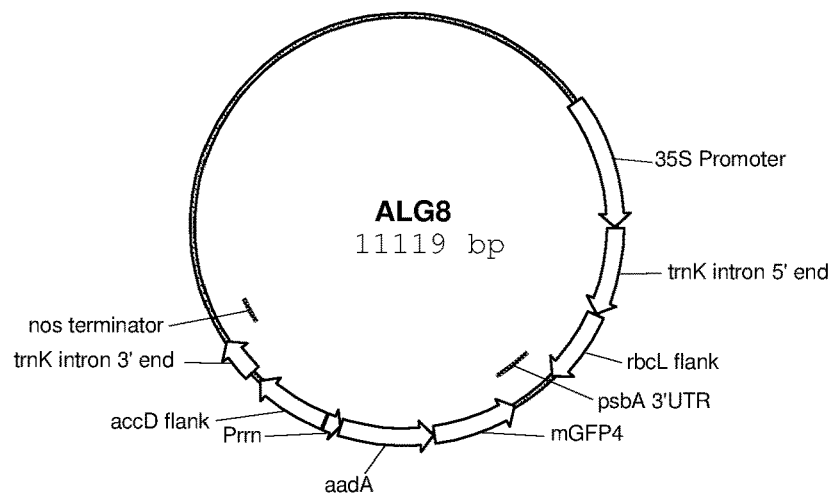
Figure 2D:
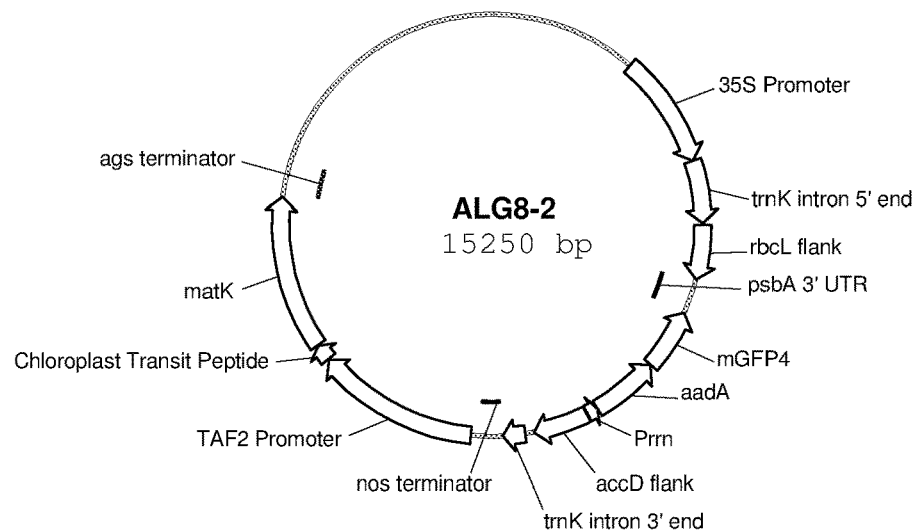
Figure 2E:
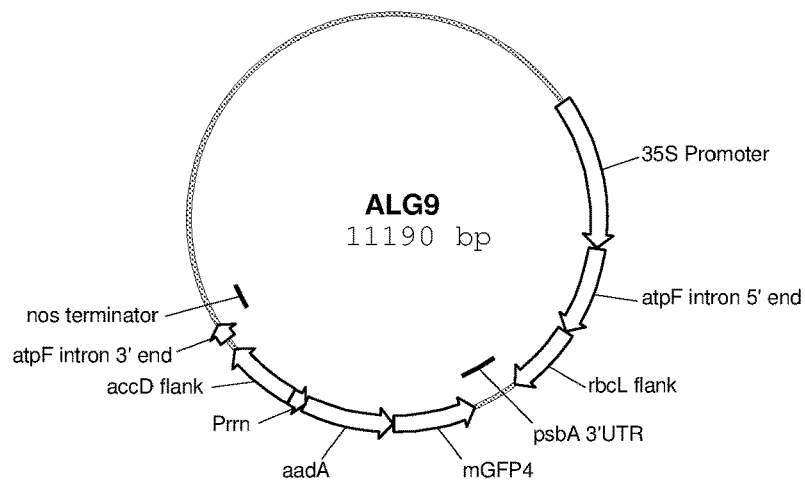
Figure 2F:
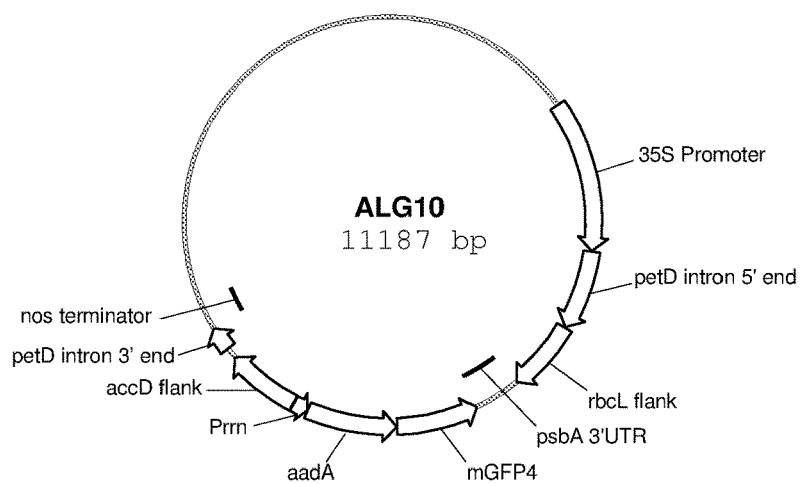

FIGS. 1A to 1C: Set of constructs for *Arabidopsis* chloroplast transformation.

FIGS. 2A-2F: Set of constructs for tobacco chloroplast transformation.

Figure 3A:
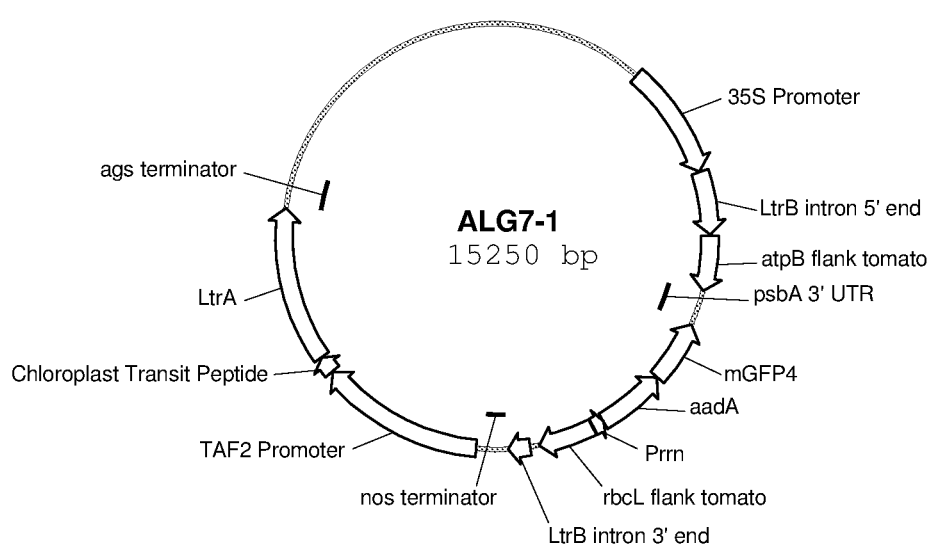
Figure 3B:
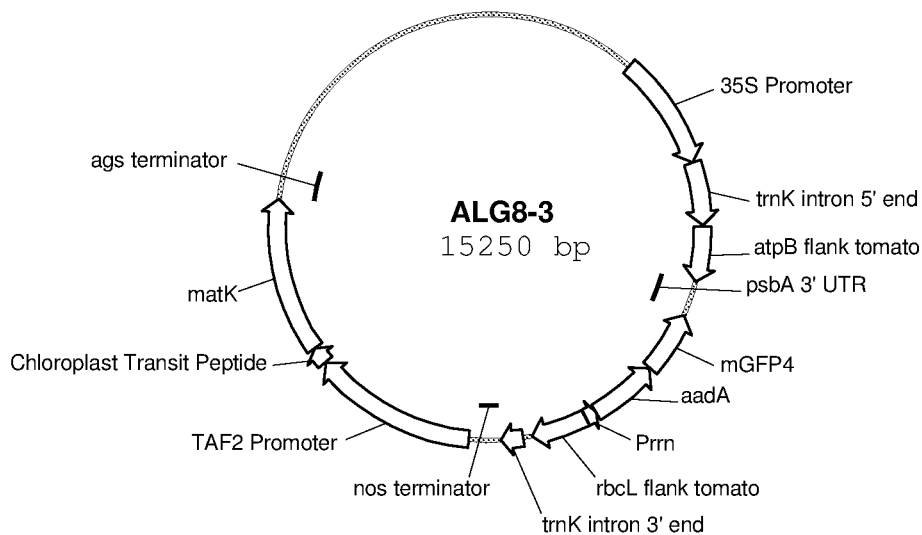

FIGS. 3A and 3B: Set of constructs for tomato chloroplast transformation.

Figure 4A:
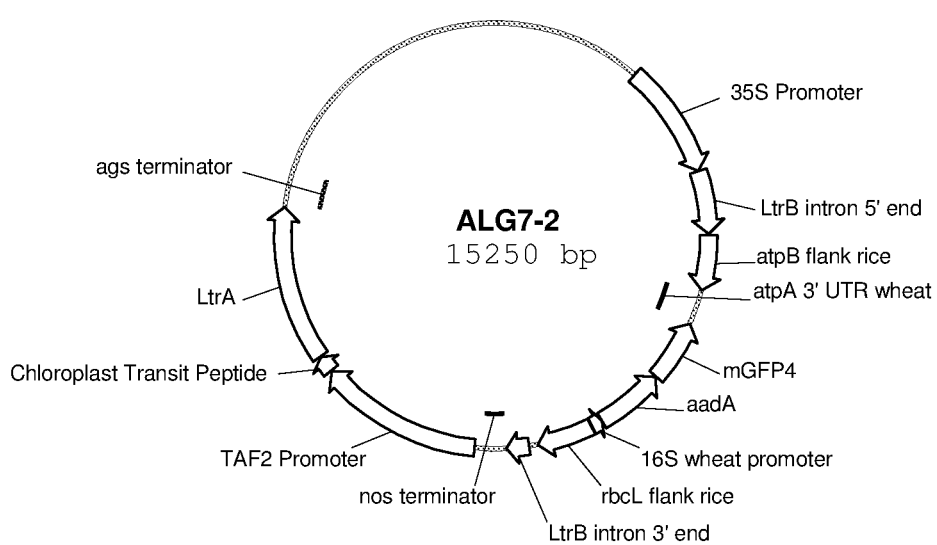
Figure 4B:
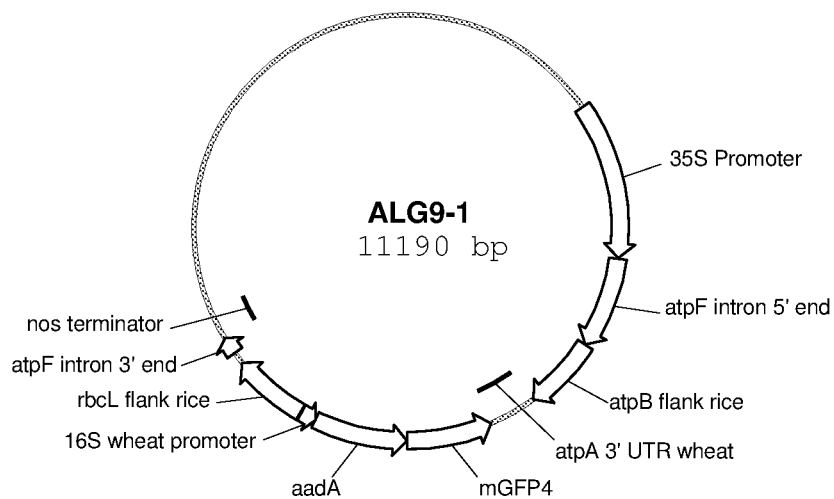
Figure 4C:
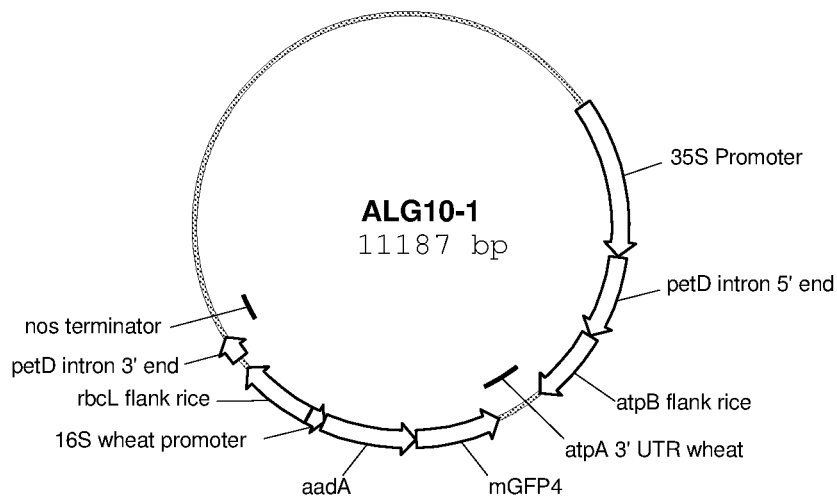

FIGS. 4A to 4C: Set of constructs for rice chloroplast transformation.

Figure 5:
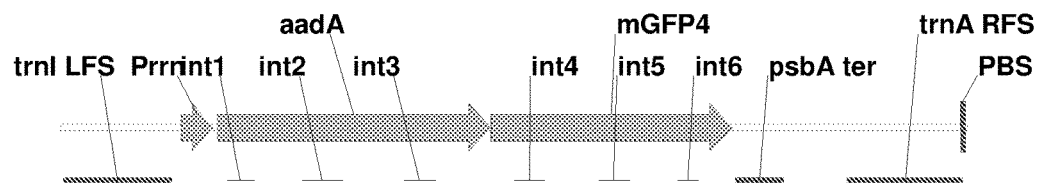

FIG. 5: Optimised chloroplast transformation cassette which includes introns in aadA and mGFP gene to stabilise transcript. trnI-LFS and trnA RFS-trnI and trnA flanking sequence; Prrn-chloroplast promoter from rrn16 gene; int1-int6-introns from the *Arabidopsis* genome introduced into coding sequences of aadA and mGFP4 genes in order to stabilise the transcript; psbA ter-chloroplast terminator from the chloroplast psbA gene; PBS-primer binding site for induction of the reverse transcriptase reaction.

Figure 6:
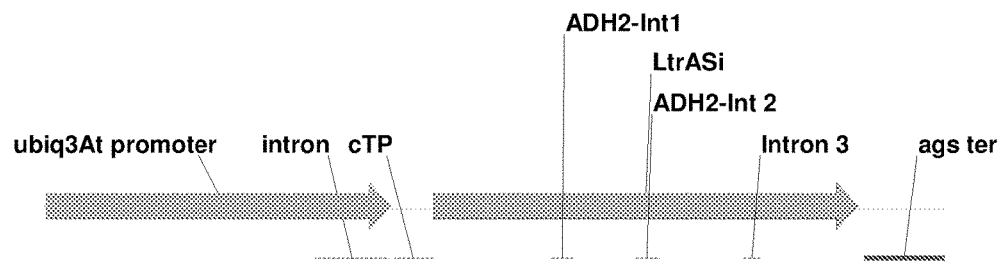

FIG. 6: Optimised cassette of LtrASi gene for expression in plants. Ubiq3At-ubiquitine 3 gene promoter from *Arabidopsis*; cTP-chloroplast transit peptide; LtrASi-synthetic LtrA gene synthesised for optimal expression in plants; ADH2-Int1, ADH2-Int2, intron 3-intron from *Arabidopsis* genome introduce to stabilise transcript of sLtrA in plants; ags ter-plant polyadenylation sequence.

Figure 7:
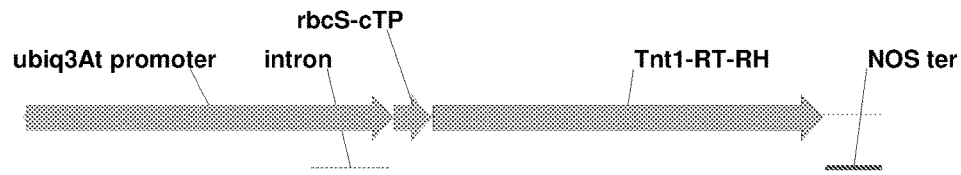

FIG. 7: Tnt1 reverse transcriptase (RT)-RNase H (RH) (RT-RH) gene cassette facilitating reverse transcription of the chloroplast transgene cassette in the chloroplasts.

Figure 8A:
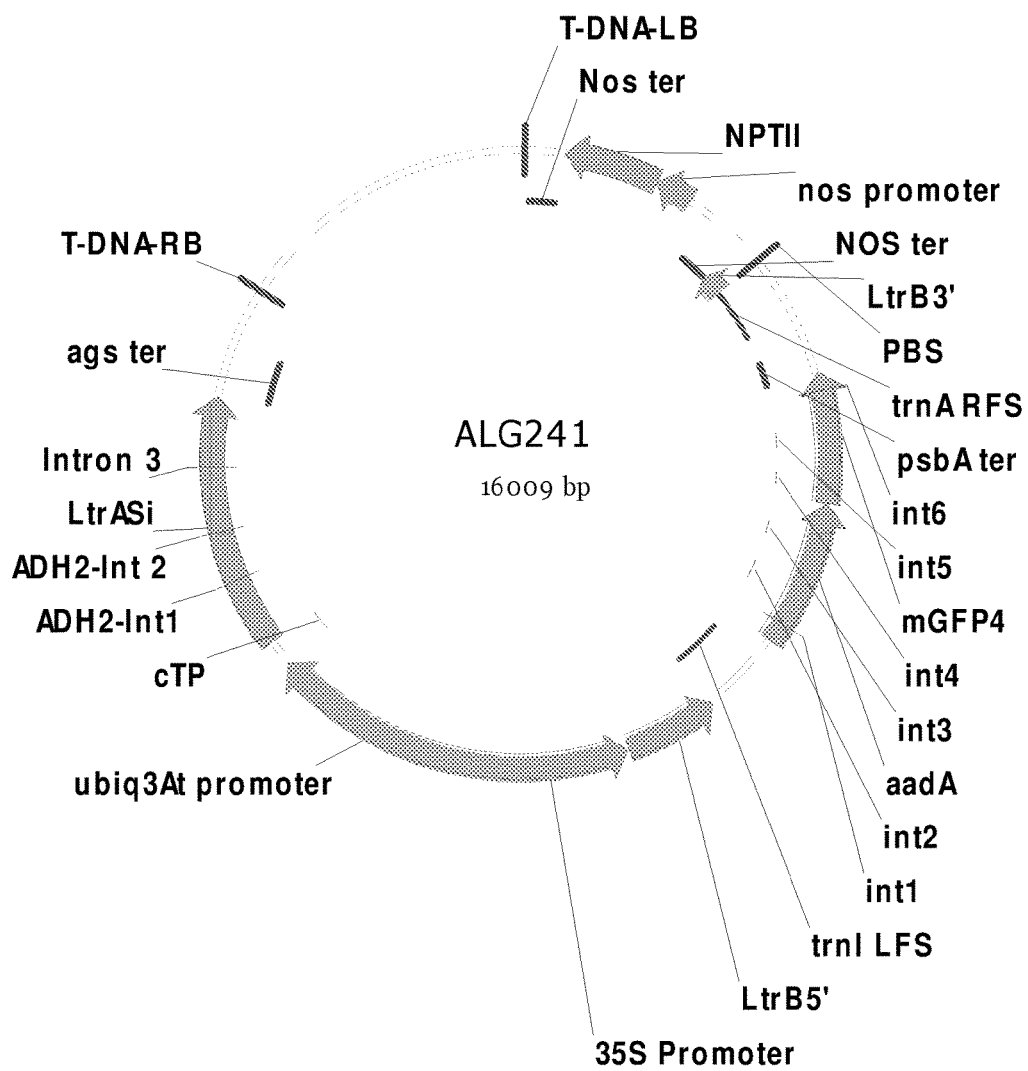
Figure 8B:
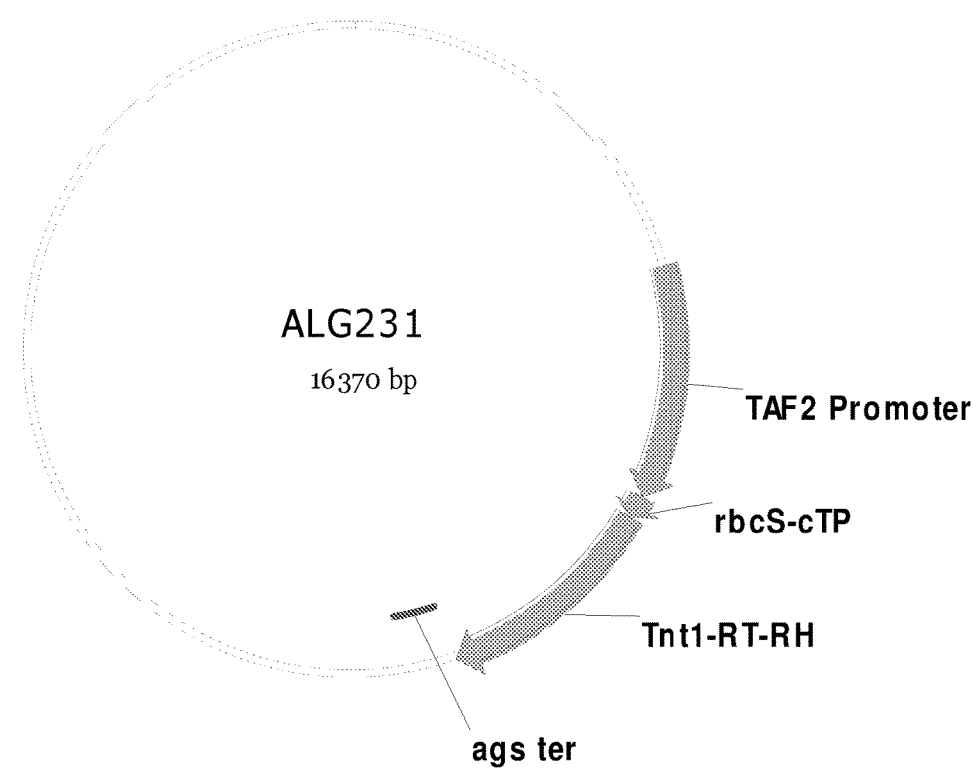

FIGS. 8A and 8B: Vector constructs used for optimisation of chloroplast transformation using group II intron transformation vector. (A) ALG241 vector carrying chloroplast transgene cassette and LtrASi gene in pGreen0029 binary vector (Hellens et al (2000) Plant Mol. Biol 42: 819-832; www.pgreen.ac.uk). (B) ALG231 vector carrying Tnt1RT-RH in pSOUP-0179 binary vector (Hellens, supra). Both plasmids were co-transformed into the *Agrobacterium* strain AGL1 which was used for tobacco transformation.

EXAMPLES

Transgene Delivery to the Chloroplasts Using Group II Intron Vectors.

Concept

We have exploited the functional features of the intron to target and insert polynucleotide sequences of interest into the plastid, for example, the chloroplast genome. Group II introns have a conserved secondary structure and comprise six functional domains. Domain IV has not been shown to play any role in the splicing reaction, but it may contain an open reading frame (ORF) encoding a multifunctional protein (IEP) that is involved in splicing and intron mobility. We have removed this ORF from intron Domain IV and replaced it with a nucleotide sequence of interest for insertion into the chloroplast genome. The native ORF of the intron was fused to an organelle transit peptide and co-expressed separately. We utilised the LtrB intron from *Lactococcus lactis* (amplified from *Lactococcus lactis* strain MG1363, Genoscope, France) and the native chloroplast trnK intron from tobacco (amplified by PCR from tobacco genomic DNA of variety Petite Gerard), both of which contain an ORF in Domain IV. The native maize atpF and petD introns (amplified from maize genomic DNA), which do not have any ORF in Domain IV, were also used. Briefly, the chloroplast transgene cassette was inserted into Domain IV of the above-mentioned introns and it was expected that intron encoded ORF co-expressed in trans or in the case of the native maize atpF and petD introns that have no ORF in Domain IV, that native protein(s) expressed from the nuclear genome would be involved in intron splicing and targeting into the chloroplasts. The chloroplast transgene cassette contains a chloroplast Prrn promoter from tobacco, aadA-GFP4 fusion sequence, psbA 3'UTR terminator sequence from the tobacco chloroplast genome and two flanking regions homologous to the region of tobacco chloroplast genome between rbcL and accD genes.

Technology Rationale

The process of chloroplast transformation comprises two steps.

(1) Targeting of RNA-Protein Complex to the Chloroplasts.

After delivery of the intron construct into the plant cell a strong expression of the intron RNA which contains the chloroplast targeted cassette is achieved from the nuclear-specific promoter. The intron encoded protein (IEP) fused to a chloroplast transit peptide, will be also over-expressed on co-delivery from the same or a different vector and then will bind to the intron RNA and facilitate folding and intron splicing from mRNA. Since the IEP is fused to a chloroplast transit peptide it will then preferentially transfer the intron RNA into the chloroplasts. For introns such as atpF and petD which do not have any ORF for IEP in Domain IV it is expected that a native nuclear-encoded protein will perform similar functions as those of the introduced IEP with the LtrB and trnk introns. Once the intron cassette is presented in the plant cell via nuclear transformation, the chloroplast will then be permanently bombarded by the expressed IEP-intron RNA complex. Such stable and continuous pumping of the complex into the targeted organelle is a prerequisite for achieving a high efficiency of organelle transformation. The technology exploits the finding that the chloroplast transit sequence is sufficient to permit the whole IEP-intron RNA complex to be then taken up by the chloroplast.

(2) Reverse Transcription of the Transgene Cassette and Insertion into the Chloroplast Genome.

Once inside the organelle, the over-expression of the reverse transcriptase (RT-RH) from the tobacco tnt1 retrotransposon fused to the Rubisco small subunit chloroplast transit peptide facilitates reverse transcription of RNA from the transgene cassette. RT-RH recognises a primer binding site (PBS) and initiates reverse transcription using chloroplast encoded tRNA-Met as primer. RT-RH will catalyse reverse transcription of the transgene cassette, and insertion of the reverse transcribed cassette into the chloroplast genome will be induced due to homologous recombination between flanking sequences of the cassette and the homologous region in the chloroplast genome.

Once the population of organelle genomes has been transformed in the initial plant line, the nuclear encoded transgenes are no longer required and they can then be removed through segregation in subsequent plant generations, leaving a clean organelle transformed plant line.

Materials and Methods.

Preparation of Group II Intron Based Vector.

The LtrB intron, not containing the intron-encoded LtrA gene in Domain IV, was amplified using standard procedures known in the art (e.g. *Molecular Cloning: a Laboratory Manual:* 2nd edition, Sambrook et al, 1989, Cold Spring Harbor Laboratory Press) from *Lactococcus lactis* strain MG1364 using the following primers:

```
for 5'-prime part of the intron
IM105
                                                              (SEQ ID NO. 1)
INT5-F (XhoI) TGTCTCGAGTGTGATTGCAACCCACGTCGAT IM106
                                                              (SEQ ID NO. 2)
INT5-R (AscI) TGTGGCGCGCCACGCGTCGCCACGTAATAAATA;
for 3'-prime part of the intron IM107
                                                              (SEQ ID NO. 3)
INT3-F (NotI) TGTGCGGCCGCTGGGAAATGGCAATGATAGCGA IM108
                                                              (SEQ ID NO. 4)
INT3-R (EcoRI) TGTGAATTCCAGTCAAATTGTTTGCCAGTATAAAG LtrB 5'-intron
                                                              (SEQ ID NO. 5)
CTCGAGTGTGATTGCAACCCACGTCGATCGTGAACACATCCATAACGTGCGCCCAGATAGGGTGTTAAGTCAA

GTAGTTTAAGGTACTACTCTGTAAGATAACACAGAAAACAGCCAACCTAACCGAAAAGCGAAAGCTGATACGG

GAACAGAGCACGGTTGGAAAGCGATGAGTTACCTAAAGACAATCGGGTACGACTGAGTCGCAATGTTAATCAG

ATATAAGGTATAAGTTGTGTTTACTGAACGCAAGTTTCTAATTTCGGTTATGTGTCGATAGAGGAAAGTGTCT

GAAACCTCTAGTACAAAGAAAGGTAAGTTATGGTTGTGGACTTATCTGTTATCACCACATTTGTACAATCTGT

AGGAGAACCTATGGGAACGAAACGAAAGCGATGCCGAGAATCTGAATTTACCAAGACTTAACACTAACTGGGG

ATACCCTAAACAAGAATGCCTAATAGAAAGGAGGAAAAAGGCTATAGCACTAGAGCTTGAAAATCTTGCAAGG

GTACGGAGTACTCGTAGTAGTCTGAGAAGGGTAACGCCCTTTACATGGCAAAGGGGTACAGTTATTGTGTACT

AAAATTAAAAATTGATTAGGGAGGAAAACCTCAAAATGAAACCAACAATGGCAATTTTAGAAAGAATCAGTAA

AAATTCACAAGAAAATATAGACGAAGTTTTTACAAGACTTTATCGTTATCTTTTACGTCCAGATATTTATTAC

GTGGCGACGCGTGGCGCGC

LtrB 3'-intron
                                                              (SEQ ID NO. 6)
GCGGCCGCTGGGAAATGGCAATGATAGCGAAACAACGTAAAACTCTTGTTGTATGCTTTCATTGTCATCGTCA

CGTGATTCATAAACACAAGTGAATTTTTACGAACGAACAATAACAGAGCCGTATACTCCGAGAGGGGTACGTA

CGGTTCCCGAAGAGGGTGGTGCAAACCAGTCACAGTAATGTGAACAAGGCGGTACCTCCCTACTTCACCATAT

CATTTTTAATTCTACGAATCTTTATACTGGCAAACAATTTGACTGGAATTC
```

Intron encoded gene for LtrA protein was amplified separately from genomic DNA of *L. lactis* strain MG1363 using the following pair of primers:

```
AS384-F (SphI)
                                                              (SEQ ID NO. 7)
GGCATGCATGAAACCAACAATGGCAATTTTA

AS187-R (SpeI)
                                                              (SEQ ID NO. 8)
GACTAGTTCACTTGTGTTTATGAATCACGTG

LtrA ORF
```

-continued

AS384-F (SphI)
(SEQ ID NO. 9)

```
GCATGCATGAAACCAACAATGGCAATTTTAGAAAGAATCAGTAAAAATTCACAAGAAAATATAGACGAAGTTT

TTACAAGACTTTATCGTTATCTTTTACGTCCAGATATTTATTACGTGGCGTATCAAAATTTATATTCCAATAA

AGGAGCTTCCACAAAAGGAATATTAGATGATACAGCGGATGGCTTTAGTGAAGAAAAAATAAAAAAGATTATT

CAATCTTTAAAAGACGGAACTTACTATCCTCAACCTGTACGAAGAATGTATATTGCAAAAAAGAATTCTAAAA

AGATGAGACCTTTAGGAATTCCAACTTTCACAGATAAATTGATCCAAGAAGCTGTGAGAATAATTCTTGAATC

TATCTATGAACCGGTATTCGAAGATGTGTCTCACGGTTTTAGACCTCAACGAAGCTGTCACACAGCTTTGAAA

ACAATCAAAGAGAGTTTGGCGGCGCAAGATGGTTTGTGGAGGGAGATATAAAAGGCTGCTTCGATAATATAG

ACCACGTTACACTCATTGGACTCATCAATCTTAAAATCAAAGATATGAAAATGAGCCAATTGATTTATAAATT

TCTAAAAGCAGGTTATCTGGAAAACTGGCAGTATCACAAAACTTACAGCGGAACACCTCAAGGTGGAATTCTA

TCTCCTCTTTTGGCCAACATCTATCTTCATGAATTGGATAAGTTTGTTTTACAACTCAAAATGAAGTTTGACC

GAGAAAGTCCAGAAAGAATAACACCTGAATATCGGGAACTTCACAATGAGATAAAAGAATTTCTCACCGTCT

CAAGAAGTTGGAGGGTGAAGAAAAAGCTAAAGTTCTTTTAGAATATCAAGAAAAACGTAAAAGATTACCCACA

CTCCCCTGTACCTCACAGACAAATAAAGTATTGAAATACGTCCGGTATGCGGACGACTTCATTATCTCTGTTA

AAGGAAGCAAAGAGGACTGTCAATGGATAAAAGAACAATTAAAACTTTTTATTCATAACAAGCTAAAAATGGA

ATTGAGTGAAGAAAAAACACTCATCACACATAGCAGTCAACCCGCTCGTTTTCTGGGATATGATATACGAGTA

AGGAGAAGTGGAACGATAAAACGATCTGGTAAAGTCAAAAAGAGAACACTCAATGGGAGTGTAGAACTCCTTA

TTCCTCTTCAAGACAAAATTCGTCAATTTATTTTTGACAAGAAAATAGCTATCCAAAAGAAAGATAGCTCATG

GTTTCCAGTTCACAGGAAATATCTTATTCGTTCAACAGACTTAGAAATCATCACAATTTATAATTCTGAATTA

AGAGGGATTTGTAATTACTACGGTCTAGCAAGTAATTTTAACCAGCTCAATTATTTTGCTTATCTTATGGAAT

ACAGCTGTCTAAAAACGATAGCCTCCAAACATAAGGGAACACTTTCAAAAACCATTTCCATGTTTAAAGATGG

AAGTGGTTCGTGGGGCATCCCGTATGAGATAAAGCAAGGTAAGCAGCGCCGTTATTTTGCAAATTTTAGTGAA

TGTAAATCCCCTTATCAATTTACGGATGAGATAAGTCAAGCTCCTGTATTGTATGGCTATGCCCGGAATACTC

TTGAAAACAGGTTAAAAGCTAAATGTTGTGAATTATGTGGAACATCTGATGAAAATACTTCCTATGAAATTCA

CCATGTCAATAAGGTCAAAAATCTTAAAGGCAAAGAAAATGGGAAATGGCAATGATAGCGAAACAACGTAAA

ACTCTTGTTGTATGCTTTCATTGTCATCGTCACGTGATTCATAAACACAAGTGAACTAGT
```

The LtrA gene was translationally fused to chloroplast transit peptide using methods commonly employed in the art (e.g. Maniatis et al, supra) from pea chloroplast heat shock protein (Accession No. L03299). The sequence for the transit peptide was amplified using the following primers:

AS293-F (XhoI)
(SEQ ID NO. 10)
TCTCGAGTTGATGGCTTCTTCTGCTCAAATA

AS294-R (SphI)
(SEQ ID NO. 11)
GGCATGCAACTCTCAAAGTGAAACCCTTC cTP
(SEQ ID NO. 12)
CTCGAGATGGCTTCTTCTGCTCAAATACACGGTCTCGGAACCGCTTCTTTCTCTTCCCTCAAAAAACCCTCTT

CCATTTCCGGTAATTCCAAAACCCTTTTCTTCGGTCAGCGACTCAATTCCAACCACTCTCCCTTCACCCGCGC

CGCATTCCCTAAGTTAAGTAGCAAAACCTTTAAGAAGGGTTTCACTTTGAGAGTTGCATGC

The trnK intron was amplified from tobacco genomic DNA of variety Petite Gerard using primers for 5' end of intron:

AS402 (XhoI)
(SEQ ID NO. 13)
GCTCGAGGTTGCTAACTCAACGGTAGAGTAC

AS521 (AscI)
(SEQ ID NO. 14)
GCACGCGTGGCGCGCCATTTCTATTTAAACCATGATCA for 3' end of intron:

AS568 (NotI)
(SEQ ID NO. 15)
CACGCGTGCGGCCGCTTCTTCTAGTTTGTGGGGAGTA

AS405 (BamHI)
(SEQ ID NO. 16)
GGGATCCGATATGCTAGTGGGTTGCCCGGGA trnK intron 5' end
(SEQ ID NO. 17)
GTGCGGCTAGTCTCTTTTACACATATGGATGAAGTGAGGGATTCGTCCATACTCTCGGTAAAGTTTGGAAGAC

CACGACTGATCCTGAAAGGGAATGAATGGTAAAAATAGCATGTCGTATCAACGGAAAGTTCTGAGAATATTTC

ATTGTTCCTAGATGGGTATAAAACCGTGTTAGAATTCTTGGAACGGAACAAAATAAAGTTGGGTCGAATGAAT

AAATGGATAGGGCTGCGGCTTCAATTAAATTATAGGGAAAGAAAGAAAAAGCAACGAGCTTTTGTTCTTAATT

TGAATGATTCCCGATCTAATTAGACGTTAAAAATTTATTAGTGCCTGATGCGGGAAGGGTTTCTTGTCCCATG

AGTGGATTCTCCATTTTTTTAATGAATCCTAACTATTACCATTTTCTATTACGGAGATGTGTGTGTAGAAGAA

ACAGTATATTGATAAAGAAAGTTTTTTCCGAAGTCAAAAGAGCGATTAGGTTGAAAAAATAAAGGATTTCTAA

CCATCTTATTATCCTATAACACTATAACATAGACCAATTAAACGAAACGAAAAAAAAAAGAGATGATAGAGAA

TCCGTTGAGAAGTTTACCTGTATCCAAGGTATCTATTCTTACTAAAATACTTTGTTTTAACTGTATCGCACTA

TGTATCATTTGATAACCCTCAAAATCTTCCGTCTTTGGTTCAAATCGAATTTCAAATGGAAGAAATCCAAAGA

TATTTACAGCCAGATAGATCGCAACAACACAACTTCCTATATCCACTTATCTTTCAGGAGTATATTTATGCAC

TTGCTCATGATCATGGTTTAAATAGAAATGCGCC trnK intron 3' end
(SEQ ID NO. 18)
TTCTTCTAGTTTGTGGGGAGTATATAGAAGTCGGATTTGGTATTTGGATATTTTTTGTATCAATGATCTGGCG

AATTATCAATGATTCATTCTTAGATTTTCTAAATGGAAATTTGTTTCTAAATGATGAAGAGATAAAAAAATTT

CACTATTCTGAAATGTTGATTGTAATAGTAATTAAGGGGTAAATCAACTGAGTATTCAACTTTTTAAAGTCTT

TCTAAATTCTATAAGAAAGGAACTGATGTATACATAGGGAAAGCCGTGTGCAATGAAAAATGCAAGCACGGCT

TGGGGAGGGGTCTTTACTTGTTTATTTAATTTAAGATTAACATTTATTTTATTTAACAAGGAACTTATCTACT

CCAT trnK intron encoded protein MatK was amplified from tobacco genomic DNA of variety Petite Gerard with primers
AS442 (SphI)
(SEQ ID NO. 19)
GGCATGCCAAATGGAAGAAATCCAAAGATA AS443 (SstI)
(SEQ ID NO. 20)
GGAGCTCTCATTGATAATTCGCCAGATCA MatK
(SEQ ID NO. 21)
GCATGCCAAATGGAAGAAATCCAAAGATATTTACAGCCAGATAGATCGCAACAACACAACTTCCTATATCCAC

TTATCTTTCAGGAGTATATTTATGCACTTGCTCATGATCATGGTTTAAATAGAAATAGGTCGATTTTGTTGGA

AAATCCAGGTTATAACAATAAATTAAGTTTCCTAATTGTGAAACGTTTAATTACTCGAATGTATCAACAGAAT

CATTTTCTTATTTCTACTAATGATTCTAACAAAAATTCATTTTTGGGGTGCAACAAGAGTTTGTATTCTCAAA

TGATATCAGAGGGATTTGCGTTTATTGTGGAAATTCCGTTTTCTCTACGATTAATATCTTCTTTATCTTCTTT

CGAAGGCAAAAGATTTTTAAATCTTATAATTTACGATCAATTCATTCAACATTTCCTTTTTTAGAGGACAAT

-continued

TTTTCACATCTAAATTATGTATTAGATATACTAATACCCTACCCTGTTCATCTGGAAATCTTGGTTCAAACTC

TTCGCTATTGGGTAAAAGATGCCTCTTCTTTACATTTATTACGATTCTTTCTCCATGAATTTTGGAATTTGAA

TAGTCTTATTACTTCAAAGAAGCCCGGTTACTCCTTTTCAAAAAAAAATCAAAGATTCTTCTTCTTCTTATAT

AATTCTTATGTATATGAATGCGAATCCACTTTCGTCTTTCTACGGAACCAATCTTCTCATTTACGATCAACAT

CTTTTGGAGCCCTTCTTGAACAATATATTTCTATGGAAAAATAGAACGTCTTGTAGAAGTCTTTGCTAAGGA

TTTTCAGGTTACCCTATGGTTATTCAAGGATCCTTTCATGCATTATGTTAGGTATCAAGGAAAATCCATTCTG

GCTTCAAAAGGGACGTTTCTTTTGATGAATAAATGGAAATTTTACCTTGTCAATTTTTGGCAATGTCATTGTT

CTCTGTGCTTTCACACAGGAAGGATCCATATAAACCAATTATCCAATCATTCCCGTGACTTTATGGGCTATCT

TTCAAGTGTGCGACTAAATCCTTCAATGGTACGTAGTCAAATGTTAGAAAATTCATTTCTAATCAATAATGCA

ATTAAGAAGTTCGATACCCTTGTTCCAATTATTCCTTTGATTGGATCATTAGCTAAAGCAAACTTTTGTACCG

TATTAGGGCATCCCATTAGTAAACCGGTTTGGTCCGATTTATCAGATTCTGATATTATTGACCGATTTGGGCG

TATATGCAGAAATCTTTTTCATTATTATAGCGGATCTTCCAAAAAAAAGACTTTATATCGAATAAAGTATATA

CTTCGACTTTCTTGTGCTAGAACTTTAGCTCGGAAACACAAAAGTACTGTACGCACTTTTTTGAAAAGATCGG

GCTCGGAATTATTGGAAGAATTCTTAACGTCGGAAGAACAAGTTCTTTCTTTGACCTTCCCACGAGCTTCTTC

TAGTTTGTGGGGAGTATATAGAAGTCGGATTTGGTATTTGGATATTTTTTGTATCAATGATCTGGCGAATTAT

CAATGAGAGCTC

Mat K was fused to chloroplast transit peptide sequence from pea HSP70
gene (see sequence above).
The atpF intron was amplified from maize genomic DNA using primers
AS409 (XhoI)for 5' end of intron (SEQ ID NO. 22)
GCTCGAGACTGTAGTGGTTGGTGTATTG AS410 (AscI)

(SEQ ID NO. 23)
GGGCGCGCCTTCTTTTTTGTTATGTATTATGGCT for 3' end of intron
AS411 (NotI)

(SEQ ID NO. 24)
GGCGGCCGCAAAAAGGAGCGGGAGAGCCAAA

AS412 (SpeI)

(SEQ ID NO. 25)
GACTAGTGAATAGTACTTAAAATCCTCTG atpF intron 5' end (SEQ ID NO. 26)
CTCGAGACTGTAGTGGTTGGTGTATTGATTTTTTTTGGAAAGGGAGTGTGTGCGAGTTGTCTATTTCAAGAAT

AGATTGGATCTATCCGGCTGCACTTTAGAATATTTTTAGTATTTTTTTTGATAAATAAGAAAAGGTGCACGAT

CTCGACGAATTACTTCTGAATAACTTCAGAAATCATATGGAAGAACCATAGCATTTCGCGATTCATTGGTAAA

TTTACTTTGATTCTCTATAGACCAATAATGTGAGACCATTAACACGGTTAAAGCTAAACTGCTTGAAGTCCGG

GCAAAAAGGGGTACTCTTTCTACAACTACATTAGTATTAGTCTCGAAATGCTTTAAACGGGAAATAGCTAGTG

TAGAATTTATCTGATATAGAACACTCATATCGATAAAATAGTTTGAACTATTTACTAGAAGGGCACGCAGCCC

TTTTTCCAATGCCAAATCGACGACCTATGTATAAAAAAAGAGAAATTTTTTGGATTTGAAGAAAAAATAAAA

GGAATTCTATCAATTTTTATTTTCCATTTATTTAGTTAGTTTTCTTAATGAAATTGAAATTATTAACTAACA

GAGCAAACACAAATAAAGAAACAACTTTGCTGACCATGATAGATTTTTATCTAGTTGGAAGAGTCCTCTTAAT

ATTCATCTAGTCTTATATAAGTTTGGGTATATAGAAATACAAACAGAAAAGAGAGGATAGAGGATAGGCTCAT

TACATAAAAAAAAGATATGGAAATAGCCATAATACATAACAAAAAAGAAGGCGCGCC

```
atpF intron 3' end
                                                              (SEQ ID NO. 27)
GCGGCCGCAAAAAGGAGCGGGAGAGCCAAATGAATCGAAAGATTCATGTTTGGTTCGGGAAGAGATCATAAAA

ATTGTAAACTTAATAGCAAGATAATCTACTTTCATTAAAAGATTTATTAGATAATCGAAAACAGAGGATTTTA

AGTACTATTCACTAGT
``` petD intron was amplified from maize genomic DNA using primers for 5' end of intron:

```
        AS413 (SalI)
                                        (SEQ ID NO. 28)
          GGTCGACGGATACTTCTCTTCAACTTCGAAGT

AS414 (SpeI)
                                        (SEQ ID NO. 29)
          GACTAGTACGCGGGTTCCCCATAATAATTATG
``` for 3' end of intron:

```
AS415 (AscI)
                                                              (SEQ ID NO. 30)
GGGCGCGCCATAATGACTCAATGACTCAAGGTA

AS416 (NotI)
                                                              (SEQ ID NO. 31)
GGCGGCCGCATACCCCTATTCTATTGTGGATC petD intron 5' end
                                                              (SEQ ID NO. 32)
GTCGACGGATACTTCTCTTCAACTTCGAAGTATTTTTATACAAATAGTTGAAGTGAATTTTACGAAAGAAAAT

AAGGCGGATTATGGGAGTGTGTGACTTGAATTATTAATTTGGCCATGCAGATAGAGAATTGGATCTGCCACAT

TAGAATTCACGACCAAAGGTGTCTCCGCATCCAATCAACACGTAAGTCCCCTATCTAGGAAGGATAGGCTGGT

TCACTCGAGGAGAATATTTTCTATGATCATACCCCACCAACCATGTCATCCATGAACAGGCTCCGTAAGATCC

TATAGAGTATAAATGGAATAAGTCATGTGATATGATCCAATTCAATTTTTATTACACTTACTTTTTATTATAG

TATGGAAATGCATTCATTTTCTTTGCATCGATTTTGATCCGCAATACTATCGGAGTAAAAGAAGGGATCTAAG

GAAGAACGCAGGCTAAACTTTTTGATTTTTTATTAGTAACAAGTAAATACTTTGTTTGGACATAAGAAACTTG

CGATATCGAGGGGATAAACAACAACTAATCAAGAGACAATCCACAAAGCAATTGATCATGATCAAATTTGTAA

GCCCACTTGGATATTGAGCATTTAAGCATAAGAATAGGATTCTTTTCAATGAGTAGTTATAGGCGCAACTTCG

GAAAAGATAATTTGATAAAGTTTTTCTTACCTTGAGTCATTGAGTCATTATGGCGCGCC petD intron 3' end
                                                              (SEQ ID NO. 33)
GCGGCCGCATACCCCTATTCTATTGTGGATCCTCCACGGTCTTATTTCTTTCATTCTTGCTCGAGCCGGATGA

TGAAAAATTCTCATGTCCGGTTCCTTTGGGGGATGGATCCTAAAGAATTCACCTATCCCAATAACAAAGAAAC

CTGACTTAAATGATCCTGTATTAAGAGCAAAATTAGCTAAAGGGATGGGACATAATTATTATGGGGAACCCGC

GTACTAGT
```

The chloroplast transformation cassette contains:

```
Prrn promoter tobacco
                                                              (SEQ ID NO. 34)
CTCGAGTTTGCTCCCCCGCCGTCGTTCAATGAGAATGGATAAGAGGCTCGTGGGATTGACGTGAGGGGGCAGG

GATGGCTATATTTCTGGGAGCGAACTCCGGGCGAATACGAAGCGCTTGGATACAGTTGTAGGGAGGGATTTCC

CGGG
```

-continued

Prrn was amplified from tobacco DNA with the primers
AS134-F (XhoI)

(SEQ ID NO. 35)
TCTCGAGTTTGCTCCCCGCCGTCGTTC (SEQ ID NO. 36)
AS135-R (SmaI) CCCCGGGCCCTCCCTGGAGTTCGCTCCCAGAAATAT

Prps16 promoter wheat (SEQ ID NO. 37)
CCGCGGCATTCATATGATAGAATATGGGTTTAAATAAATTGGCTCTTTGCGGAGTCTTTCCCGATAAATACTT

AATTTCTTTTATTCATATTTCTCCATAGATAGCAAAGCAAGTTTGAATTAGTATACAAAAAACGAAACTAATG

ACTATTCATGATTCCATCCATATTGGATCAATTCCCTATAACACTTTGCAATGAAATTAGAGGAATGTTATCG

AT

Prps16 was amplified from wheat genomic DNA cv. Pavon using primers
AS425 (SstII)

(SEQ ID NO. 38)
GCCGCGGCATTCATATGATAGAATATGGGT

AS518 (ClaI)

(SEQ ID NO. 39)
TATCGATAACATTCCTCTAATTTCATTGCA aadA gene (SEQ ID NO. 40)
CCCGGGATGAGGGAAGCGGTGATCGCCGAAGTATCGACTCAACTATCAGAGGTAGTTGGCGTCATCGAGCGCC

ATCTCGAACCGACGTTGCTGGCCGTACATTTGTACGGCTCCGCAGTGGATGGCGGCCTGAAGCCACACAGTGA

TATTGATTTGCTGGTTACGGTGACCGTAAGGCTTGATGAAACAACGCGGCGAGCTTTGATCAACGACCTTTTG

GAAACTTCGGCTTCCCCTGGAGAGAGCGAGATTCTCCGCGCTGTAGAAGTCACCATTGTTGTGCACGACGACA

TCATTCCGTGGCGTTATCCAGCTAAGCGCGAACTGCAATTTGGAGAATGGCAGCGCAATGACATTCTTGCAGG

TATCTTCGAGCCAGCCACGATCGACATTGATCTGGCTATCTTGCTGACAAAAGCAAGAGAACATAGCGTTGCC

TTGGTAGGTCCAGCGGCGGAGGAACTCTTTGATCCGGTTCCTGAACAGGATCTATTTGAGGCGCTAAATGAAA

CCTTAACGCTATGGAACTCGCCGCCCGACTGGGCTGGCGATGAGCGAAATGTAGTGCTTACGTTGTCCCGCAT

TTGGTACAGCGCAGTAACCGGCAAAATCGCGCCGAAGGATGTCGCTGCCGACTGGGCAATGGAGCGCCTGCCG

GCCCAGTATCAGCCCGTCATACTTGAAGCTAGACAGGCTTATCTTGGACAAGAAGAAGATCGCTTGGCCTCGC

GCGCAGATCAGTTGGAAGAATTTGTCCACTACGTGAAAGGCGAGATCACCAAGGTAGTCGGCAAATCAGGATCC aadA gene was amplified from *E. coli* carrying pCN1 plasmid (Chinault et al (1986) Plasmid 15:119-131) using primers:

AS130 (Sma I)

(SEQ ID NO. 41)
GCCCGGGATGAGGGAAGCGGTGATCGCCGA

AS131 (Bam HI)

(SEQ ID NO. 42)
GGGATCCTGATTTGCCGACTACCTTGGT mGFP4 gene (SEQ ID NO. 43)
GGATCCATGAGTAAAGGAGAAGAACTTTTCACTGGAGTTGTCCCAATTCTTGTTGAATTAGATGGTGATGTTA

ATGGGCACAAATTTTCTGTCAGTGGAGAGGGTGAAGGTGATGCAACATACGGAAAACTTACCCTTAAATTTAT

TTGCACTACTGGAAAACTACCTGTTCCATGGCCAACACTTGTCACTACTTTCTCTTATGGTGTTCAATGCTTT

TCAAGATACCCAGATCATATGAAGCGGCACGACTTCTTCAAGAGCGCCATGCCTGAGGGATACGTGCAGGAGA

GGACCATCTTCTTCAAGGACGACGGGAACTACAAGACACGTGCTGAAGTCAAGTTTGAGGGAGACACCCTCGT

CAACAGGATCGAGCTTAAGGGAATCGATTTCAAGGAGGACGGAAACATCCTCGGCCACAAGTTGGAATACAAC

TACAACTCCCACAACGTATACATCATGGCAGACAAACAAAAGAATGGAATCAAAGTTAACTTCAAAATTAGAC

-continued

ACAACATTGAAGATGGAAGCGTTCAACTAGCAGACCATTATCAACAAAATACTCCAATTGGCGATGGCCCTGT
CCTTTTACCAGACAACCATTACCTGTCCACACAATCTGCCCTTTCGAAAGATCCCAACGAAAAGAGAGACCAC
ATGGTCCTTCTTGAGTTTGTAACAGCTGCTGGGATTACACATGGCATGGATGAACTATACAAATAATCTAGA mGFP4 gene was synthesised based on NCBI data bank (http://www.ncbi.nlm.nih.gov/) Ac. No. U87624 and amplified using primers:

AS132 (Bam HI)
(SEQ ID NO. 44)
GGGATCCATGAGTAAAGGAGAAGAACT

AS133 (Xba I)
(SEQ ID NO. 45)
TTCTAGATTATTTGTATAGTTCATCCA

The aadA and mGFP4 were then fused into one sequence to generate aadA-mGFP4 fusion
aadA-mGFP4 fusion sequence
(SEQ ID NO. 46)
CCCGGGATGAGGGAAGCGGTGATCGCCGAAGTATCGACTCAACTATCAGAGGTAGTTGGCGTCATCGAGCGCC
ATCTCGAACCGACGTTGCTGGCCGTACATTTGTACGGCTCCGCAGTGGATGGCGGCCTGAAGCCACACAGTGA
TATTGATTTGCTGGTTACGGTGACCGTAAGGCTTGATGAAACAACGCGGCGAGCTTTGATCAACGACCTTTTG
GAAACTTCGGCTTCCCCTGGAGAGAGCGAGATTCTCCGCGCTGTAGAAGTCACCATTGTTGTGCACGACGACA
TCATTCCGTGGCGTTATCCAGCTAAGCGCGAACTGCAATTTGGAGAATGGCAGCGCAATGACATTCTTGCAGG
TATCTTCGAGCCAGCCACGATCGACATTGATCTGGCTATCTTGCTGACAAAAGCAAGAGAACATAGCGTTGCC
TTGGTAGGTCCAGCGGCGGAGGAACTCTTTGATCCGGTTCCTGAACAGGATCTATTTGAGGCGCTAAATGAAA
CCTTAACGCTATGGAACTCGCCGCCCGACTGGGCTGGCGATGAGCGAAATGTAGTGCTTACGTTGTCCCGCAT
TTGGTACAGCGCAGTAACCGGCAAAATCGCGCCGAAGGATGTCGCTGCCGACTGGGCAATGGAGCGCCTGCCG
GCCCAGTATCAGCCCGTCATACTTGAAGCTAGACAGGCTTATCTTGGACAAGAAGAAGATCGCTTGGCCTCGC
GCGCAGATCAGTTGGAAGAATTTGTCCACTACGTGAAAGGCGAGATCACCAAGGTAGTCGGCAAATCAGGATC
CATGAGTAAAGGAGAAGAACTTTTCACTGGAGTTGTCCCAATTCTTGTTGAATTAGATGGTGATGTTAATGGG
CACAAATTTTCTGTCAGTGGAGAGGGTGAAGGTGATGCAACATACGGAAAACTTACCCTTAAATTTATTTGCA
CTACTGGAAAACTACCTGTTCCATGGCCAACACTTGTCACTACTTTCTCTTATGGTGTTCAATGCTTTTCAAG
ATACCCAGATCATATGAAGCGGCACGACTTCTTCAAGAGCGCCATGCCTGAGGGATACGTGCAGGAGAGGACC
ATCTTCTTCAAGGACGACGGGAACTACAAGACACGTGCTGAAGTCAAGTTTGAGGGAGACACCCTCGTCAACA
GGATCGAGCTTAAGGGAATCGATTTCAAGGAGGACGGAAACATCCTCGGCCACAAGTTGGAATACAACTACAA
CTCCCACAACGTATACATCATGGCAGACAAACAAAAGAATGGAATCAAAGTTAACTTCAAAATTAGACACAAC
ATTGAAGATGGAAGCGTTCAACTAGCAGACCATTATCAACAAAATACTCCAATTGGCGATGGCCCTGTCCTTT
TACCAGACAACCATTACCTGTCCACACAATCTGCCCTTTCGAAAGATCCCAACGAAAAGAGAGACCACATGGT
CCTTCTTGAGTTTGTAACAGCTGCTGGGATTACACATGGCATGGATGAACTATACAAATAATCTAGA psbA terminator from tobacco
(SEQ ID NO. 47)
TCTAGACTGGCCTAGTCTATAGGAGGTTTTGAAAAGAAAGGAGCAATAATCATTTTCTTGTTCTATCAAGAGG
GTGCTATTGCTCCTTTCTTTTTTCTTTTTATTTATTTACTAGTATTTTACTTACATAGACTTTTTTGTTTAC
ATTATAGAAAAGAAGGAGAGGTTATTTTCTTGCATTTATTCATGATTGAGTATTCTATTTTGATTTTGTATT
TGTTTAAATTGTGAAATAGAACTTGTTTCTCTTCTTGCTAATGTTACTATATCTTTTTGATTTTTTTTTCCA
AAAAAAAATCAAATTTTGACTTCTTCTTATCTCTTATCTTTGAATATCTCTTATCTTTGAAATAATAATATC
ATTGAAATAAGAAAGAAGAGCTATATTCGACCGCGG psbA terminator was amplified from tobacco genomic DNA of variety Petite Gerard with primers:

AS136 (Xba I)  
(SEQ ID NO. 48)  
GTCTAGAGATCTTGGCCTAGTCTATAGGA

AS137 (Sac II)  
(SEQ ID NO. 49)  
GCCGCGGTCGAATATAGCTCTTCTTTCTTA atpA terminator from wheat  
(SEQ ID NO. 50)  
ACTAGTCAAATAAATTTTGCATGTCTACTCTTGTTAGTAGAATAGGAATCGTTGAGAAAGATTTTTCATTTGA

ATCATGCAAAAAAGTTTTCTTTGTTTTTAGTTTAGTATAGTTATTTAAAGAATAGATAGAAATAAGATTGCGT

CCAATAGGATTTGAACCTATACCAAAGGTTTAGAAGACCTCTGTCCTATCCATTAGACAATGGACGCTTTTCT

TTCATATTTTATTCTTTCTTTTATTTTTTTTTCTTCTTCCGAGAAAAAACTGTTAGACCAAAACTCTTTTAGG

AAATCAAAAAATCCAGATACAAATGCATGATGTATATATTATATCATGCATATATCATAAAGAAGGAGTATGG

AAGCTT was amplified from wheat genomic DNA cv Pavon using primers  
AS427 (SpeI)  
(SEQ ID NO. 51)  
GACTAGTCAAATAAATTTTGCATGTCTACTC AS428 (HindIII)  
(SEQ ID NO. 52)  
GAAGCTTTCCATACTCCTTCTTTATGATATATG

*Arabidopsis* atpB Flanking Sequence  
(SE ID NO. 53)  
AAGCTTTCTCATAATAAAAAAAATATGTTAAATTTTGTTACGAATTTTTTCGAATACAGAAAAAATCTTCGAT

AGCAAATTAATCGGTTAATTCAATAAAAAGTGGGAGTAAGCACTCGATTTCGTTGGTCCCACCCAAGCGGATG

TGGAATTCAATTTTTTATTCATTCAATGAAGGAATAGTCATTTTCAAGCTCAACTAACTGAAACCTAGTTTTA

AAATAAAAAATATATGAATAAAAAAATTTTTTGCGGAAAGTCTTTTATTTTTTTATCATAATAGGAATAGGCA

AGCCTTTGTTTTATCTAGCGAATTCGAAACGGAACTTTAGTTATGATTCATTATTTCGATCTCATTAGCCTTT

TTTTTCGTATTTTCATTTTAGCATATCCGGTTCTCGAG

40 was amplified from genomic DNA of *Arabidopsis thaliana* (Col-0) with the primers:

Clf-f (Hind III)  
(SEQ ID NO. 54)  
CCCAAGCTTTCTCATAATAAAAAAAATATGTTA

Clf-r (Xho I)  
(SEQ ID NO. 55)  
CCGCTCGAGAACCGGATATGCTAAAATGAAAATA

*Arabidopsis* rbcL Flanking Sequence  
(SEQ ID NO. 56)  
CCGCGGATGCGTCCCATTTATTCATCCCTTTAGCAACCCCCCCTTGTTTTTCATTTTCATGGATGAATTCCGC

ATATTGTCATATCTAGGATTTACATATACAACAGATATTACTGTCAAGAGTGATTTTATTAATATTTTAATTT

TAATATTAAATATTTGGATTTATAAAAAGTCAAAGATTCAAAACTTGAAAAAGAAGTATTAGGTTGCGCTATA

CATATGAAAGAATATACAATAATGATGTATTTGGCGAATCAAATATCATGGTCTAATAAAGAATAATTCTGAT

TAGTTGATAATTTTGTGAAAGATTCCTGTGAAAAAGGTTAATTAAATCTATTCCTAATTTATGTCGAGTAGAC

CTTGTTGTTTTGTTTTATTGCAAGAATTCTAAATTCATGACTTGTAGGGAGGGACTTATGTCTAGA was amplified from genomic DNA of *Arabidopsis thaliana* (Col-0) using primers:

```
Crf-f (Sac II)
                                                   (SEQ ID NO. 57)
TCCCCGCGGATGCGTCCCATTTATTCATCCCT

Crf-r (Xba I)
                                                   (SEQ ID NO. 58)
GCTCTAGACATAAGTCCCTCCCTACAAGT

Tobacco rbcL Flanking Sequence
                                                   (SEQ ID NO. 59)
GGCGCGCCGAGACATAACTTTGGGCTTTGTTGATTTACTGCGTGATGATTTTGTTGAACAAGATCGAAGTCGC

GGTATTTATTTCACTCAAGATTGGGTCTCTTTACCAGGTGTTCTACCCGTGGCTTCAGGAGGTATTCACGTTT

GGCATATGCCTGCTCTGACCGAGATCTTTGGGGATGATTCCGTACTACAGTTCGGTGGAGGAACTTTAGGACA

TCCTTGGGGTAATGCGCCAGGTGCCGTAGCTAATCGAGTAGCTCTAGAAGCATGTGTAAAAGCTCGTAATGAA

GGACGTGATCTTGCTCAGGAAGGTAATGAAATTATTCGCGAGGCTTGCAAATGGAGCCCGGAACTAGCTGCTG

CTTGTGAAGTATGGAAAGAGATCGTATTTAATTTTGCAGCAGTGGACGTTTTGGATAAGTAAAAACAGTAGAC

ATTAGCAGATAAATTAGCAGGAAATAAAGAAGGATAAGGAGAAAGAACTCAAGTAATTATCCTTCGTTCTCTT

AATTGAATTGCAATTAAACTCGGCCCAATCTTTTACTAAAAGGATTGAGCCGAATACAACAAAGATTCTATTG

CATATATTTTGACTAAGTATATACTTACCTAGATATACAAGATTTGAAATACAAAATCTAGCCGCGG
``` was amplified from tobacco genomic DNA of variety Petite Gerard with primers:

```
AS395 (AscI)
                                                   (SEQ ID NO. 60)
GGGCGCGCCGAGACATAACTTTGGGCTTTGTTGA

AS397 (SacII)
                                                   (SEQ ID NO. 61)
GGCCGCGGCTAGATTTTGTATTTCAAATCTTGT

Tobacco accD Flanking Sequence
                                                   (SEQ ID NO. 62)
CTCGAGAACTAAATCAAAATCTAAGACTCAAATCTTTCTATTGTTGTCTTGGATCCACAATTAATCCTACGGA

TCCTTAGGATTGGTATATTCTTTTCTATCCTGTAGTTTGTAGTTTCCCTGAATCAAGCCAAGTATCACACCTC

TTTCTACCCATCCTGTATATTGTCCCCTTTGTTCCGTGTTGAAATAGAACCTTAATTTATTACTTATTTTTTT

ATTAAATTTTAGATTTGTTAGTGATTAGATATTAGTATTAGACGAGATTTTACGAAACAATTATTTTTTTATT

TCTTTATAGGAGAGGACAAATCTCTTTTTTCGATGCGAATTTGACACGACATAGGAGAAGCCGCCCTTTATTA

AAAATTATATTATTTTAAATAATATAAAGGGGGTTCCAACATATTAATATATAGTGAAGTGTTCCCCCAGATT

CAGAACTTTTTTTCAATACTCACAATCCTTATTAGTTAATAATCCTAGTGATTGGATTTCTATGCTTAGTCTG

ATAGGAAATAAGATATTCAAATAAATAATTTTATAGCGAATGACTATTCATCTATTGTATTTTCATGCAAATA

GGGGGCAAGAAAACTCTATGGAAAGATGGTGGTTTAATTCGATGTTGTTTAAGAAGGAGTTCGAACGCACTAG
T
``` was amplified from tobacco genomic DNA of variety Petite Gerard with primers:

```
AS396 (SpeI))
                                                   (SEQ ID NO. 63)
GGACTAGTGCGTTCGAACTCCTTCTTAAACAAC

AS398 (XhoI)
                                                   (SEQ ID NO. 64)
GGCTCGAGAACTAAATCAAAATCTAAGACTCA
```

-continued

Tomato atpB Flanking Sequence (tmLFS)
(SEQ ID NO. 65)
GGCGCGCCGTCCGCTAGCACGTCGATCGGTTAATTCAAAAAAATCGGAATTAGCACTCGATTTCGTTGGCACC

ATGCAATTGAACCAATCCAATTGTTTACTTATTCAATGAGACTGAGTTAATTTGGAAGCTCACCCAACCTATT

TTCATTTAAAAATCTCAAGTGGATGAATCAGAATCTTGAGAAATTCTTTCATTTGTCTATCATTATAGACAAG

CCCATCCATATTATCGATTCTATGGAATTCGAACCTGAACTTTATTTTCTATTTCTATTACGATTCATTATTT

GTATCTAATGGGCTCCTCTTCTTATTTATTTTTTATTTAAATTTCAGCATATCGATTTATGCCTAGCCTATTC

TTTTCTTTGCGTTTTTCTTTCTTTTTTATACCTTTCATAGATTCATAGAGGAATTCCATATATTTTCACATCT

AGGATTTACATATACAACATATACCACTGTCAAGGGGGAAGTTCCCGCGG was amplified from tomato genomic DNA (*Lycopersicon esculentum* var. Moneymaker) with primers AS417 (AscI)
(SEQ ID NO. 66)
GGGCGCGCCGTCCGCTAGCACGTCGATCGGT AS418 (SstII)
(SEQ ID NO. 67)
GCCGCGGGAACTTCCCCCTTGACAGTGGTAT Tomato rbcL Flanking Sequence (tmRFS)
(SEQ ID NO. 68)
GTCGACAGGGGGAAGTTCTTATTATTTAGGTTAGCTAGGTATTTCCATTTCAAAAAAAAAAAGGTAAAAAAT

CAAAATTGGGTTGCGCTATATATATGAAAGAGTATACAATAATGATGTATTTGGCAAATCAAATACCATGGTC

TAATAATCAACCATTCTGATTAATTGATAATATTAGTATTAGTTGGAAATTTTGTGAAAGATTCCTGTGAAAA

GTTTCATTAACGCGGAATTCATGTCGAGTAGACCTTGCTGTTGTGAGAATTCTTAATTCATGAGTTGTAGGGA

GGGATTTATGTCACCACAAACAGAGACTAAAGCAAGTGTTGGATTCAAAGCTGGTGTTAAAGAGTACAAATTG

ACTTATTATACTCCTGAGTACCAAACCAAGGATACTGATATATTGGCAGCATTCCGAGTAACTCCTCAACCTG

GAGTTCCACCTGAAGAAGCAGGGGCCGCGGTAGCTGCCGAATCTTCTACTGGTACATGGACAACTGTATGGAG

CATGC was amplified from tomato genomic DNA (*Lycopersicon esculentum* var. Moneymaker) with primers:

AS419 (SalI)
(SEQ ID NO. 69)
GGTCGACAGGGGGAAGTTCTTATTATTTAGGT

AS420 (SphI)
(SEQ ID NO. 70)
GGCATGCTCCATACAGTTGTCCATGTACCAGT

Rice atpB Flanking Sequence (rLFS)
(SEQ ID NO. 71)
GGCGCGCCCTTGTTGAATAATGCCAAATCAACACCAAAAAAATATCCAAAAATCCAAAAGTCAAAAGGAAATG

AATTAGTTAATTCAATAAGAGAGAAAAGGGGACCAGCACTTGATTTCGTTGCCCAAACGAATCCCATTCAATC

GTTTACTCATGGAATGAGCCCGTCGGAAAGTTCAATCAATCTTTTTTTCATATACATTTTGCCTTTTGTAAAC

GATTTGTGCCTACTCTACTTTCTTATCTAGGACTTCGATATACAAAATATATACTACTGTGAAGCATAGATTG

CTGTCAACAGAGAATTTTCGTAGTATTTAGGTATTTCCACTCAAAATAAGAAAAGGGGGTCTATTAAGAACTT

AATAAGGATTAGAAGTTGATTTGGGGTTGCGCTATATCTATTAAAGAGTATACAATAAAGATGGATTTGGTGA

ATCAAATCCATGGTTTAATAACGAAGCATGTTAACTTACCATAACAACAACAAGCTT was amplified from rice genomic DNA (*Oryza sativa*), var. Nippon bare with primers:

AS421 (AscI)
(SEQ ID NO. 72)
GGGCGCGCCCTTGTTGAATAATGCCAAATCAA

AS422 (HindIII)
(SEQ ID NO. 73)
GAAGCTTGTTGTTGTTATGGTAAGTTAACA

Rice Right rbcL Sequence (rRFS)
(SEQ ID NO. 74)
CCGCGGTCAATTCTTATCGAATTCCTATAGTAGAATTCCTATAGCATAGAATGTACACAGGGTGTACCCATTA

TATATGAATGAAACATATTATATGAATGAAACATATTCATTAACTTAAGCATGCCCCCCATTTTCTTTAATGA

GTTGATATTAATTGAATATCTTTTTTTTAAGATTTTTGCAAAGGTTTCATTTACGCCTAATCCATATCGAGTA

GACCCTGTCGTTGTGAGAATTCTTAATTCATGAGTTGTAGGGAGGGACGTATGTCACCACAAACAGAAACTAA

AGCAAGTGTTGGATTTAAAGCTGGTGTTAAGGATTATAAATTGACTTACTACACCCCGGAGTACGAAACCAAG

GACACTGATATCTTGGCAGCATTCCGAGTAACTCCTCAGCCGGGGGTTCCGCCCGAAGAAGCAGGGGCTGCAG

TAGCTGCCGAATCTTCTACTGGTACATGGACAACTGTTTGGACTGATGGACTTACCAGTCTTGAGCATGC was amplified from rice genomic DNA (*Oryza sativa*), var. Nippon bare
with primers
AS423 (SstII)
(SEQ ID NO. 75)
GCCGCGGTCAATTCCTATCGAATTCCTATAGTA AS424 (SphI)
(SEQ ID NO. 76)
GGCATGCTCAAGACTGGTAAGTCCATCAGTCC 35S Promoter was synthesized based on NCBI data bank Ac. No. NC_001497
(http://www.ncbi.nlm.nih.gov/) was used for expression of intron
containing the chloroplast transgene cassette.
35S Promoter
(SEQ ID NO. 77)
GAATTCCAATCCCACAAAAATCTGAGCTTAACAGCACAGTTGCTCCTCTCAGAGCAGAATCGGGTATTCAACA

CCCTCATATCAACTACTACGTTGTGTATAACGGTCCACATGCCGGTATATACGATGACTGGGGTTGTACAAAG

GCGGCAACAAACGGCGTTCCCGGAGTTGCACACAAGAAATTTGCCACTATTACAGAGGCAAGAGCAGCAGCTG

ACGCGTACACAACAAGTCAGCAAACAGACAGGTTGAACTTCATCCCCAAAGGAGAAGCTCAACTCAAGCCCAA

GAGCTTTGCTAAGGCCCTAACAAGCCCACCAAAGCAAAAAGCCCACTGGCTCACGCTAGGAACCAAAAGGCCC

AGCAGTGATCCAGCCCCAAAAGAGATCTCCTTTGCCCCGGAGATTACAATGGACGATTTCCTCTATCTTTACG

ATCTAGGAAGGAAGTTCGAAGGTGAAGTAGACGACACTATGTTCACCACTGATAATGAGAAGGTTAGCCTCTT

CAATTTCAGAAAGAATGCTGACCCACAGATGGTTAGAGAGGCCTACGCAGCAGGTCTCATCAAGACGATCTAC

CCGAGTAACAATCTCCAGGAGATCAAATACCTTCCCAAGAAGGTTAAAGATGCAGTCAAAAGATTCAGGACTA

ATTGCATCAAGAACACAGAGAAAGACATATTTCTCAAGATCAGAAGTACTATTCCAGTATGGACGATTCAAGG

CTTGCTTCATAAACCAAGGCAAGTAATAGAGATTGGAGTCTCTAAAAAGGTAGTTCCTACTGAATCTAAGGCC

ATGCATGGAGTCTAAGATTCAAATCGAGGATCTAACAGAACTCGCCGTGAAGACTGGCGAACAGTTCATACAG

AGTCTTTTACGACTCAATGACAAGAAGAAAATCTTCGTCAACATGGTGGAGCACGACACTCTGGTCTACTCCA

AAAATGTCAAAGATACAGTCTCAGAAGACCAAAGGGCTATTGAGACTTTTCAACAAAGGATAATTTCGGGAAA

CCTCCTCGGATTCCATTGCCCAGCTATCTGTCACTTCATCGAAAGGACAGTAGAAAAGGAAGGTGGCTCCTAC

AAATGCCATCATTGCGATAAAGGAAAGGCTATCATTCAAGATCTCTCTGCCGACAGTGGTCCCAAAGATGGAC

CCCCACCCACGAGGAGCATCGTGGAAAAAGAAGACGTTCCAACCACGTCTTCAAAGCAAGTGGATTGATGTGA

CATCTCCACTGACGTAAGGGATGACGCACAATCCCACTATCCTTCGCAAGACCCTTCCTCTATATAAGGAAGT

TCATTTCATTTGGAGAGGACACGCTCGAG

*Arabidopsis* TAF2 promoter was used to drive expression of intron encoded proteins (IEP). It was amplified from genomic DNA of *Arabidopsis thaliana* (Col-0) using the following primers:

TAF2-F
(SEQ ID NO. 153)
GGTACCATGATCGCTTCATGTTTTTATC

TAF2-R
(SEQ ID NO. 154)
CTCGAGGTTCCTTTTTTGCCGATATGTT

*Arabidopsis* TAF2 promoter
(SEQ ID NO. 78)
GGTACCATGATCGCTTCATGTTTTTATCTAATTTGTTAGCATATTGAATGATTGATTTTCTTTTAATTTGGAT

ATGTTGATTGTCTTGTTGCATCATCAATGTATGTTTTATTTAACACCGGAAGATCTTATGATGGGTTCATTAC

TTCATAATAATCTCCGAGTTCTACAAGACTACAACTTTCACGTGACTTTTACAGCGACAAAAAATGCATCTAG

CGAAAATTAATCCACAACCTATGCATTTTTGTCACTCTTCACACGCGTATGTGCATAAATATATAGTATATAC

TCGACAATCGATGCGTATGTGTACACAATTACCAAAACAATTATTTGAATATTCAGACATGGGTTGACATCAC

CAAGTAATATTCACAGTATCTGAAAACTATGTTTTGACATCCCTAAATAGTTTGACTAACCAGTTTAATATGA

GAGCATTTGTAAGAGGCAAGAGCCATGGTTTTGTTGGCTCGTTTAATATGCTCATTTAACCCCCCCAAAAAAT

ACTATTAGATTTAAACGTAAAAGAATTAACGAACACAAGAACTGCTAAAACAAAAAAAAATCAATGGCCGACA

TTTCATAGTTCATACATCACTAATACTAAAAGATGCATCATTTCACTAGGGTCTCATGAAATAGGAGTTGACA

TTTTTTTTTGTAACGACAGAAGTTGACATGTTAAGCATCAATTTTTTTAAGAGTGGATTATACTAGTTTTTTT

TTTTTTTTTTAATGTATGGTATGATACAACAACAAAAACTATAAAATAGAAAAAGTCAGTGAAACCTCAAATT

GAAGGAAAAACTTTTGCACAAAAAGAGAGAGAGAGAGAAAGAATGTAAATCCAAATAAATGGGCCTAATTGAG

AATGCTTTAACTTTTTTTTTTGGCTAAAAGAGAATGCTTTAACTAAGCCCATAAAATGAACATCAAACTCAA

AGGGTAAGATTAATACATTTAGAAAACAATAGCCGAATATTTAATAAGTTTAAGACATAGAGGAGTTTTATGT

AATTTAGGAACCGATCCATCGTTGGCTGTATAAAAAGGTTACATCTCCGGCTAACATATCGGCAAAAAAGGAA

CCTCGAG

Plant Transformation

Transformation of *Arabidopsis* Plants

Transformation of *Arabidopsis* plants was performed as described by Clough & Bent (Clough & Bent (1998) Plant Journal 16:735-743). *Agrobacterium tumefacience* strain GV3101 (Koncz & Schell (1986) Mol Gen Genet 204:383-396) was used for transformation. Transformation of plants was carried out with three different constructs ALG4-1, ALG4-2 and ALG8-1 (FIGS. 1A, 1B and 1C) based on the pGreen 0029 binary vector (Hellens et al (2000) Plant Mol. Biol 42: 819-832). In brief, a chloroplast transformation cassette containing atpB flank, Prrn promoter, aadA-mGFP4 fusion, psbA 3' UTR, rbcL flank was inserted into domain IV of the LtrB or trnK introns using AscI-NotI enzymes. The introns containing the transformation cassette were fused to the 35S promoter and nos terminator and introduced into the pGreen0029 binary vector (FIG. 1A). The LtrB intron encoded protein LtrA was fused to a chloroplast transit peptide and inserted into pGreen 0029 together with the cassette from ALG4-1, resulting in ALG4-2. Transgenic lines were recovered on selection medium supplemented with 50 mg/l of kanamycin.

Transformation of Tobacco Plants

Tobacco plants were transformed as described by Horschet (Horschet et al (1985) Science 227: 1229-1231) using *Agrobacterium* strain AGL1 (see protocol, below).

Five constructs comprising four different introns, the LtrB intron from *Lactococcus lactis*, trnK intron from tobacco, and the atpF and petD introns from maize were used for vector construction (FIGS. 2A to 2F). A chloroplast transgene cassette carrying rbcL flank, Prrn promoter, aadA-mGFP4 fusion, psbA 3' UTR, accD flank was inserted into domain IV of each of the said introns. The intron containing the transgene cassette was placed under control of the 35S promoter and nos terminator, and then inserted into the binary vector pGreen0029, resulting in constructs ALG6, ALG8, ALG9, ALG10. The LtrB intron encoded gene for LtrA was fused to a chloroplast transit peptide and *Arabidopsis* TAF2 promoter was added to the ALG6 construct resulting in ALG7 vector. The trnK intron encoded gene for matK proteins was also fused with chloroplast transit peptide and added to ALG8 resulting in ALG8-1 vector. Transgenic tobacco plants were regenerated on selection medium supplemented with 300 mg/l of kanamycin.

Transformation of Tomato Plants

Transgenic tomato plants were generated as described by Fillatti et al. (Fillatti et al (1987) Bio/Technology 5, 726-730) using *Agrobacterium* strain AGL1 (see protocol, below). Two constructs were prepared based on ALG7 and ALG8-2 vectors, wherein tobacco flanking sequences were replaced by tomato specific atpB and rbcL flanking sequences resulting in ALG7-1 and ALG8-3 vectors (FIGS. 3A and 3B).

Transformation of Rice Plants

Rice transformation was performed using particle bombardment as described by Christou et al (Christou et al (1991) Bio/Technology 9:957-962). The japonica rice cultivar Nipponbare was used for transformation. A chloroplast transgene cassette containing rice atpB flanking region, wheat 16S promoter, aadA-mGFP4 fusion, wheat atpA ternminator, and rice rbcL flanking sequences was prepared. This transgene cassette was inserted into the LtrB intron cassette, atpF intron cassette and petD intron cassette in the pGreen 0179 vector containing hygromycin encoded resistance, resulting in vectors ALG7-2, ALG9-1 and ALG10-1 (FIGS. 4A, 4B and 4C). Transgenic plants were recovered on medium supplemented with 50 mg/l of hygromycin.

Molecular-Biological Analysis

DNA from transgenic plants was isolated using the procedure described by Puchooa (Puchooa (2004) African J Biotech 3:253-255) or by using Invitrogen DNeasy plant mini kit following the manufacturer's instructions. RNA was isolated using TRI REAGENT™ (Sigma).

PCR reactions were performed using GoTaq Flexi DNA Polymerase (Promega), following the manufacturer's instructions. The following primers were used:

```
Arabidopsis
MS7
CCCTCTGTCGCACTCATAGCTACAG       (SEQ ID NO. 79)

MS18
GGAGATGTTGTGCGAGTATCGACAGG      (SEQ ID NO. 80)

IM68
CAACCATTACCTGTCCACACAATCTGCC    (SEQ ID NO. 81)

IM69
GCTGGGATTACACATGGCATGGATGAAC    (SEQ ID NO. 82)

IM70
ATAGGTGAAAGTAGTGACAAGTGTTGGC    (SEQ ID NO. 83)

IM71
CGTATGTTGCATCACCTTCACCCTCTC     (SEQ ID NO. 84)

Tobacco
AS457
AGAGAATTGGGCGTTCCGATCGTAA       (SEQ ID NO. 85)

AS458
GGATTCACCGCAAATACTAGCTTG        (SEQ ID NO. 86)

AS459
GAAATTCCGAATGTCTTTAACGCCGA      (SEQ ID NO. 87)

AS460
TGGAATAACTGTCTCCATTCCTATCACT    (SEQ ID NO. 88)

IM68
CAACCATTACCTGTCCACACAATCTGCC    (SEQ ID NO. 81)

IM69
GCTGGGATTACACATGGCATGGATGAAC    (SEQ ID NO. 82)

IM70
ATAGGTGAAAGTAGTGACAAGTGTTGGC    (SEQ ID NO. 83)

IM71
CGTATGTTGCATCACCTTCACCCTCTC     (SEQ ID NO. 84)

Tomato
TM1
AAAGGCTACATCTAGTACCGGAC         (SEQ ID NO. 89)

TM2
CCAGAAGTAGTAGGATTGATTCTCA       (SEQ ID NO. 90)

TM3
CGATCAAGACTGGTAAGTCCAT          (SEQ ID NO. 91)

TM4
ACAATGGAAGTAAGCATATTGGTAA       (SEQ ID NO. 92)
```

-continued

```
Rice
RC1
GGGTCCAATAATTTGATCGATA          (SEQ ID NO. 93)

RC2
CGAGAAGTAGTAGGATTGGTTCTC        (SEQ ID NO. 94)

RC3
GTCTAATGGATAAGCTACATAAGCGA      (SEQ ID NO. 95)

RC4
CCCACAATGGAAGTAAACATGT          (SEQ ID NO. 96)
```

Amplified fragments were cloned into the pGEM t-easy vector and sequenced to confirm correct insertion site. Non-radioactive Southern and Northern analyses were performed using DIG High Prime DNA Labeling and Detection Kit and DIG Northern Kit (Roche) following manufacturer's instructions.

Results and Discussion

The transformation of Arabidopsis, tobacco, tomato and rice was performed with group II-based intron vectors containing transgene cassettes for chloroplast transformation. Vectors with intron encoded proteins (IEP) such as LtrA and matK or without introduced IEP were used. In all cases we were able to detect insertion of the transgene cassette into the chloroplast genome using PCR amplification of junction regions. Five independent transgenic lines were analysed for all constructs and we could amplify correct size DNA fragment for insertion junctions in all lines. The amplified fragments were sequenced and correct insertion sites were confirmed. The same data was generated with PCR amplification of insertion flanks in tobacco for lines with tobacco trnK intron based vector (ALG8) and maize atpF and petD based vectors. Northern analysis was also performed to confirm presence of sense chloroplast transcripts. All transformation vectors had the transgene cassette inserted in the antisense orientation and as a result, the transcript generated from the nucleus will also be in the antisense orientation. Only the transgene cassette which is inserted into the chloroplast genome can generate a sense transcript of the transgene. We have prepared DIG-labeled antisense probes using T3 RNA polymerase and used them in Northern hybridisation. Indeed, we could detect sense transcripts on total RNA in all lines transformed with ALG6,ALG7 and ALG8 vectors. No signal was detected on the mRNA sample indicating that the transcript was of chloroplast origin (chloroplast transcripts are mainly not polyadenylated) or in the negative control where total RNA of wild type tobacco was used.

We have learned that over-expression of the IEP improves the efficiency of transformation, however, endogenous proteins expressed from the nucleus may also perform the same functions due to the conserved structure of the intron. Putative proteins related to group II reverse transcriptase/ maturases were identified using sequence alignments in Arabidopsis and rice genomes (Mohr & Lambowitz (2003) Nucleic Acids Research 31:647-652). It has also been shown that a number of proteins expressed from the nucleus (CRS1, CRS2, CAF1, HCF-152) are participating in splicing of organellar introns (Jenkins et al (1997) Plant Cell 9:283-296; Vogel et al (1999) Nucleic Acids Research 27:3866-3874; Fisk et al (1999) EMBO J 18: 2621-2630; Meierhoff et al (2003) Plant Cell 15: 1480-1495; Ostheimer et al (2003) EMBO J 22: 3919-3929). These proteins bind to intron RNA and are thought to serve as a vessel for targeting of RNA of intron-based vectors into the organelles. The chloroplast genome of plants contains only one ORF matK which is similar to the LtrA gene from *L. lactis* and is encoded by the trnK intron. It has been shown that this protein has intron RNA-binding activity and may be responsible for reverse transcription in the chloroplasts (Liere & Link (1995) Nucleic Acids Research 23: 917-921). The presence of this protein in chloroplasts is the major prerequisite for insertion of intron-based vectors as they could be reverse transcribed by matK after targeting into the chloroplasts by nuclear-encoded proteins involved in splicing.

2. Chloroplast Transformation Optimisation

The following improvements were introduced to optimise efficiency of chloroplast transformation:

1. The Ll.LtrB intron of *Lactococcus lactis* was optimised in silica by eliminating cryptic splicing sites and optimising its expression in plants using the web-based programme found at http://www.cbs.dtu.dk/services/NetPGene/.
2. The chloroplast transgene cassette was modified by insertion of introns from the *Arabidopsis* genes At2g29890 (introns 1, 2, 3, 5, 6) and At1g67090 (intron 4) (http://www.arabidopsis.org/servlets/Search?type=general&action=new search) which stabilises the transcript in plant cells, and by addition of a primer binding site (PBS) to the 3' end of the cassette to better facilitate reverse transcription of the cassette;
3. A synthetic LtrA gene was synthesised with optimal plant codon usage for expression in plants, and selected introns from the *Arabidopsis* At5g43940 gene were introduced to improve stability of the RNA transcript;
4. Over-expression of the reverse transcriptase (RT-RH) from the tobacco tnt1 retrotransposon (Accession No. x13777) fused to the Rubisco small subunit chloroplast transit peptide (Accession No. x02353, position 1048-1218) from tobacco was generated to facilitate reverse transcription of RNA from the transgene cassette. RT-RH recognises the primer binding site (PBS) and so initiates reverse transcription using the chloroplast tRNA-Met as a primer.

```
Optimised L1.LtrB intron
                                                             (SEQ ID NO. 97)
ACACATCCATAACGTGCGCCCAGATAGGGTGTTAAGTCAAGTAGTTTAAGGTACTACTCAGTAAGATAACACT

GAAAACAGCCAACCTAACCGAAAAGCGAAAGCTGATACGGGAACAGAGCACGGTTGGAAAGCGATGAGTTAGC

TAAAGACAATCGGCTACGACTGAGTCGCAATGTTAATCAGATATAAGCTATAAGTTGTGTTTACTGAACGCAA

GTTTCTAATTTCGGTTATGTGTCGATAGAGGAAAGTGTCTGAAACCTCTAGTACAAAGAAAGCTAAGTTATGG

TTGTGGACTTAGCTGTTATCACCACATTTGTACAATCTGTTGGAGAACCAATGGGAACGAAACGAAAGCGATG

GCGAGAATCTGAATTTACCAAGACTTAACACTAACTGGGGATAGCCTAAACAAGAATGCCTAATAGAAAGGAG

GAAAAAGGCTATAGCACTAGAGCTTGAAAATCTTGCAAGGCTACGGAGTAGTCGTAGTAGTCTGAGAAGGCTA

ACGGCCTTTACATGGCAAAGGGCTACAGTTATTGTGTACTAAAATTAAAAATTGATTAGGGAGGAAAACCTCA

AAATGAAACCAACAATGGCAATTTTAGAAAGAATCAGTAAAAATTCACAAGAAAATATAGACGAAGTTTTTAC

AAGACTTTATCGTTATCTTTTACGTCCTGATATTTATTACGTGGCGGGCGCGCCACGCGTGCGGCCGCTGGGA

AATGGCAATGATAGCGAAAGAACCTAAAACTCTGGTTCTATGCTTTCATTGTCATCGTCACGTGATTCATAAA

CACAAGTGAATTTTTACGAACGAACAATAACAGAGCCGTATACTCCGAGAGGGGTACGTACGGTTCCCGAAGA

GGGTGGTGCAAACCAGTCACAGTAATGTGAACAAGGCGGTACCTCCCTACTTCAC

Synthetic LtrA gene optimised for plant transformation (LtrASi)
                                                             (SEQ ID NO. 98)
ATGAAGCCAACAATGGCAATCCTCGAACGAATCTCTAAGAACTCACAGGAGAACATCGACGAGGTCTTCACAA

GACTTTACCGTTACCTTCTCCGTCCTGACATCTACTACGTGGCATATCAGAACCTCTACTCTAACAAGGGAGC

TTCTACAAAGGGAATCCTCGATGATACAGCTGATGGATTCTCTGAGGAGAAGATCAAGAAGATCATCCAATCT

TTGAAGGACGGAACTTACTACCCTCAGCCTGTCCGAAGAATGTACATCGCAAAGAAGAACTCTAAGAAGATGA

GACCTCTTGGAATCCCAACTTTCACAGACAAGTTGATCCAGGAGGCTGTGAGAATCATCCTTGAATCTATCTA

TGAGCCTGTCTTCGAGGATGTGTCTCACGGTTTCCGACCTCAGCGAAGCTGTCACACAGCTTTGAAGACAATC

AAGAGAGAGTTCGGAGGTGCAAGATGGTTCGTGGAGGGAGATATCAAGGGATGCTTCGATAACATCGACCACG

TCACACTCATCGGACTCATCAACCTTAAGATCAAGGATATGAAGATGAGCCAGTTGATCTACAAGTTCCTCAA

GGCAGGTACCTTTATCCTCGATCCTCGCACTCTCACTATCGTAGACATGTTATTGAAAAACCCTATCTCCGA

TTATTAGTTTTCTGATTTTCATTTCATTTTGACGCCGATTCACATAGGTTACCTCGAAAACTGGCAGTACCAC

AAGACTTACAGCGGAACACCTCAGGGCGGAATCCTCTCTCCTCTCCTCGCTAACATCTATCTTCATGAATTGG

ACAAGTTCGTTCTCCAACTCAAGATGAAGTTCGACCGAGAGAGTCCAGAGAGAATCACACCTGAATACCGGGA
```

-continued
```
GCTTCACAACGAGATCAAAAGAATCTCTCACCGTCTCAAGAAGTTGGAGGGCGAGGAGAAGGCTAAGGTTCTC

TTGGAATACCAGGAGAAGAGGAAGAGGTTGCCTACACTCCCTTGTACATCACAAACAAACAAGGTTCGTTCTC

TCCATTTTCATTCGTTTGAGTCTGATTTAGTGTTTTGTGGTTGATCTGAATCGATTTATTGTTGATTAGTGAA

TCAATTTGAGGCTGTGTCCTAATGTTTTGACTTTTGATTACAGGTCTTGAAGTACGTCCGATACGCTGACGAC

TTCATCATCTCTGTTAAGGGAAGCAAGGAGGACTGTCAATGGATCAAGGAGCAATTGAAGCTCTTCATCCATA

ACAAGCTCAAGATGGAATTGAGTGAGGAGAAGACACTCATCACACATAGCAGTCAGCCTGCTCGTTTCCTCGG

ATACGACATCCGAGTCAGGAGAAGTGGAACTATCAAGCGATCTGGAAAGGTCAAGAAGAGAACACTCAACGGG

AGTGTGGAGCTTCTCATCCCTCTCCAAGACAAGATCCGTCAATTCATCTTCGACAAGAAGATCGCTATCCAGA

AGAAGGATAGCTCATGGTTCCCAGTTCACAGGAAGTACCTTATCCGTTCAACAGACTTGGAGATCATCACAAT

CTACAACTCTGAATTGAGAGGTAAGCTGCTACCTCAAACTTTCTAGTGCTTCCATATTTCCTTTCTTCTGCAA

GGCAGAGAACCATTGTGGTTAAGTGTTTTAAATTGTGAATGTATAGGTATCTGCAACTACTACGGTCTCGCAA

GTAACTTCAACCAGCTCAACTACTTCGCTTACCTTATGGAATACTCTTGCTTGAAGACTATCGCATCTAAGCA

TAAGGGAACACTCTCAAAGACCATCTCTATGTTCAAGGATGGAAGTGGTTCTTGGGGAATCCCTTACGAGATC

AAGCAGGGGAAGCAGAGGAGATACTTCGCCAACTTCAGTGAATGCAAATCTCCTTACCAATTCACTGATGAGA

TCAGTCAAGCTCCTGTGCTTTACGGATACGCTCGGAACACTCTTGAGAACAGACTTAAGGCTAAGTGTTGTGA

GCTTTGTGGAACATCTGATGAGAACACATCTTACGAGATCCACCACGTCAACAAGGTCAAGAACCTTAAGGGA

AAGGAGAAGTGGGAGATGGCAATGATCGCTAAGCAGCGGAAGACTCTTGTTGTTTGCTTCCATTGTCATCGTC

ACGTGATCCATAAGCACAAGTGA
```

The LtrASi (LtrASi: LtrA Synthetic+Introns) sequence was designed in silico and then chemically synthesised using introns that were introduced into the synthetic sequence using overlapping primers.

The introns were amplified from *Arabidopsis* genomic DNA using the following primers:

```
IM333
                              (SEQ ID NO. 99)
ATCTACAAGTTCCTCAAGGCAGGTACCTTTATCCTCGATCCTCG

IM334
                              (SEQ ID NO. 100)
TACTGCCAGTTTTCGAGGTAACCTATGTGAATCGGCGTCAAAAT
for intron 1;

IM337
                              (SEQ ID NO. 101)
TTGTACATCACAAACAAACAAGGTTCGTTCTCTCCATTTTCATT

IM338
                              (SEQ ID NO. 102)
CGTATCGGACGTACTTCAAGACCTGTAATCAAAAGTCAAAACAT
for intron 2.

IM341
                              (SEQ ID NO. 103)
ATCTACAACTCTGAATTGAGAGGTAAGCTGCTACCTCAAACTTT

IM342
                              (SEQ ID NO. 104)
AGACCGTAGTAGTTGCAGATACCTATACATTCACAATTTAAAAC
for intron 3.
```

The LtrAS coding region was amplified using standard procedures employed in the art (e.g. Maniatis et al supra) using the following primers:

```
LTRA-F21
                              (SEQ ID NO. 105)
GCATGCATGAAGCCAACAATGG

IM332
                              (SEQ ID NO. 106)
CGAGGATCGAGGATAAAGGTACCTGCCTTGAGGAACTTGTAGAT
for fragment 1;

IM335
                              (SEQ ID NO. 107)
ATTTTGACGCCGATTCACATAGGTTACCTCGAAAACTGGCAGTA

IM336
                              (SEQ ID NO. 108)
AATGAAAATGGAGAGAACGAACCTTGTTTGTTTGTGATGTACAA
for fragment 2;

IM339
                              (SEQ ID NO. 109)
ATGTTTTGACTTTTGATTACAGGTCTTGAAGTACGTCCGATACG

IM340
                              (SEQ ID NO. 110)
AAAGTTTGAGGTAGCAGCTTACCTCTCAATTCAGAGTTGTAGAT
for fragment 3;

IM343
                              (SEQ ID NO. 111)
GTTTTAAATTGTGAATGTATAGGTATCTGCAACTACTACGGTCT

LTRA-R21
                              (SEQ ID NO. 112)
TTACTAGTTCACTTGTGCTTATGG
for fragment 4.
```

The intron and coding sequence fragments were pooled together and PCR amplification using methods commonly employed in the art (Maniatis et al, supra) of the whole LtrASi sequence was performed with LTRA-F21 and LTRA-R21 primers.

aadA-mGFP fusion optimised for transformation (SEQ ID NO. 113)

ATGGCAGAAGCGGTGATCGCCGAAGTATCGACTCAACTATCAGAGGTAAGTAACTTTTAGCTCTCAGCTGCTG
TTTACTAAGTTCATGCCATACATTGATTCTGGTTTATTAAGGGTTATGTTCAGTATTACTAGTAACAAAATCT
ATTTCTTCGTTTCCGTCTGCAGGTAGTTGGCGTCATCGAGCGCCATCTCGAACCGACGTTGCTGGCCGTACAT
TTGTACGGCTCCGCAGTGGATGGCGGCCTGAAGCCACACAGTGATATTGATTTGCTGGTTACGGTGACCGTAA
GGCTTGATGAAACAACGCGGCGAGCTTTGATCAACGACCTTTTGGAAACTTCGGCTTCCCCTGGAGAGAGCGA
GATTCTCCGCGCTGTAGAGGTAATTTTCATCTTTGTTTGGCCTTCCAAGTGCTTTTTTTGCTGTTTACGGGTG
GAACTTCAGTAAAAATGGGATCAAAACATCATATGGCATAAATAAATTTTAAGAATGGCGAACTCGGGGTTAC
CGAATATGGCTTCCTTTTTCAGTGTTTCTTAGTCCATTGTACTTATGAGATTGCAGGTCACCATTGTTGTGCA
CGACGACATCATTCCGTGGCGTTATCCAGCTAAGCGCGAACTGCAATTTGGAGAATGGCAGCGCAATGACATT
CTTGCAGGTATCTTCGAGCCAGCCACGATCGACATTGATCTGGCTATCTTGCTGACAAAAGCAAGAGAACATA
GCGTTGCCTTGGTAGGTCCAGCGGCGGAGGAACTCTTTGATCCGGTTCCTGAACAGGATCTATTTGAGGCGCT
AAATGAAACCTTAACGCTATGGAACTCGCCGCCCGACTGGGCAGGTAAGAAATCTTTTCCCATCTTGAAGTCA
CCTCAAACCGAACGTTAGGAAATTCCAAAATGTTTTGATAGTAGTCTACTTAGTTTCAAGTTTTGGGTTTGTG
TATACTTTCACTAATAATATGCGTGGAAACATTGCAGGTGATGAGCGAAATGTAGTGCTTACGTTGTCCCGCA
TTTGGTACAGCGCAGTAACCGGCAAAATCGCGCCGAAGGATGTCGCTGCCGACTGGGCAATGGAGCGCCTGCC
GGCCCAGTATCAGCCCGTCATACTTGAAGCTAGACAGGCTTATCTTGGACAAGAAGAAGATCGCTTGGCCTCG
CGCGCAGATCAGTTGGAAGAATTTGTCCACTACGTGAAAGGCGAGATCACCAAGGTAGTCGGCAAATCAGGAT
CCATGGCTAGCAAAGGAGAAGAACTTTTCACTGGAGTTGTCCCAATTCTTGTTGAATTAGATGGTGATGTTAA
TGGGCACAAATTTTCTGTCAGTGGAGAGGGTGAAGGTAATTAAACAAAATTTAAACATCTATATAAACTAGCT
AGATCTTAGGAAAATTTGGTTTAATATATTAGGATCTTGATTTATATAAACATGTTCAAAATGTTATCTGAGT
GGTTTGTAACATGTGGTTTGTATAGGTGATGCTACATACGGAAAACTTACCCTTAAATTTATTTGCACTACTG
GAAAACTACCTGTTCCTTGGCCAACACTTGTCACTACTTTCTCTTATGGTGTTCAATGCTTTTCCCGTTATCC
GGATCAGATGAAACGGCATGACTTTTTCAAGAGTGCCATGCCCGAAGGTTATGTACAGGAACGCACTATATCT
TTCAAAGATGACGGGAACTACAAGACGCGTGCTGAAGTCAAGTTTGAAGGTAAGTAAATATTGGTAATATAAC
ATTTTTACATGACTTTGGTGTCTTAATTTGTCGTTTCGCATGTGTTTCATTTAGTTTCTGCCAGAGCATCTGA
GAGGCCATTCTTAATATATGATATGATGTTGCTTTGCTCTAGGTGATACCCTTGTTAATCGTATCGAGTTGAA
AGGAATCGACTTCAAGGAAGATGGAAACATCCTCGGACACAAGCTGGAGTACAACTACAACTCACACAACGTG
TACATCACCGCAGACAAACAGAAGAATGGAATCAAAGCTAACTTCAAAATTCGCCACAACATTGAAGATGGTT
CCGTTCAACTAGCAGACCATTATCAACAAAATACTCCAATAGGTACGCAGGCTATATAGGCTTTGACATTTTT
TTGTTTTCATATTTTTCTTTGTTCCACTATGAACTTCATTCTGTTTTTTGACTTCATTGCAGGTGATGGCCCT
GTCCTTTTACCAGACAACCATTACCTGTCGACACAATCTGCCCTTTCGAAAGATCCCAACGAAAAGCGAGACC
ACATGGTCCTTCTTGAGTTTGTAACAGCTGCTGGGATTACACATGGCATGGATGAGCTCTACAAATAA

The introns were inserted into aadA-mGFP4 fusion sequence by PCR with overlapping primers. Introns were amplified by PCR from *Arabidopsis* genomic DNA using the following primers:

aadAF2
(SEQ ID No. 114)
actatcagaggtaagtaacttttagctctca aadAR2
(SEQ ID No. 115)
cgccaactacctgcagacggaaacgaagaa
for intron 1;

aadAF4
(SEQ ID NO. 116)
cgctgtagaggtaattttcatctttgtttggcct aadAR4
(SEQ ID NO. 117)
caatggtgacctgcaatctcataagtacaatg
for intron 2;

aadAF6
(SEQ ID NO. 118)
gactgggcaggtaagaaatcttttcccatcttga aadAR6
(SEQ ID NO. 119)
cgctcatcacctgcaatgtttccacgcatat
for intron 3;

mGFP2F
(SEQ ID NO. 120)
gagggtgaaggtaatttattcttctttgttttc mGFP2R
(SEQ ID NO. 121)
gtagcatcacctgtttaagaagaaaatcaaaat
for intron 4;

mGFP4F
(SEQ ID NO. 122)
aagtttgaaggtaagtaaatattggtaatataac mGFP4R
(SEQ ID NO. 123)
agggtatcacctagagcaaagcaacatcatatc
for intron 5;

mGFP6F
(SEQ ID NO. 124)
tactccaataggtacgcaggctatataggctttg mGFP6R
(SEQ ID No. 125)
agggccatcacctgcaatgaagtcaaaaaacag
for intron 6 (FIG. 5).

The PCR for aadA fragments was performed with the following primers:

AS756
(SEQ ID NO. 126)
atacaagtgagttgtagggagggaatcatggcagaagcggtgatcgccga aadAR1
(SEQ ID NO. 127)
aagttacttacctctgatagttgagtcgata
for fragment 1;

aadAF3
(SEQ ID NO. 128)
ccgtctgcaggtagttggcgtcatcgagcgcca aadAR3
(SEQ ID NO. 129)
gatgaaaattacctctacagcgcggagaatct
for fragment 2;

aadAF5
(SEQ ID NO. 130)
gagattgcaggtcaccattgttgtgcacgac aadAR5
(SEQ ID NO. 131)
agatttcttacctgcccagtcgggcggcga
for fragment 3;

aadAF7
(SEQ ID NO. 132)
aaacattgcaggtgatgagcgaaatgtagtgct

AS131
(SEQ ID NO. 133)
tcctgatttgccgactaccttggt
for fragment 4.

The fragments amplified with primers for introns 1, 2 and 3 were mixed with the fragments 1, 2, 3 and 4 amplified from the aadA gene and PCR was performed with AS756 and AS131 primers to generate aadA sequence with introns.

mGFP gene fragments were amplified with the following primers:

AS132
(SEQ ID NO. 134)
gggatccatgagtaaaggagaagaact mGFPR1
(SEQ ID NO. 135)
aaaatttagaacagatattgaccttcaccctctccactgacagaa
for fragment 1;

mGFPF3
(SEQ ID NO. 136)
ttcttaaacaggtgatgctacatacggaaaac mGFPR3
(SEQ IS NO. 137)
atttacttaccttcaaacttgacttcagcac
for fragment 2;

mGFPF5
(SEQ ID NO. 138)
ctttgctctaggtgataccccttgttaatcgta mGFPR5
(SEQ ID NO. 139)
agcctgcgtacctattggagtattttgttgataat
for fragment 3;

mGFPF7
(SEQ ID NO. 140)
ttcattgcaggtgatggccctgtccttttacca

AS133
(SEQ ID NO. 141)
ttctagattatttgtatagttcatcca
for fragment 4.

The intron 4, 5 and 6 fragments were mixed with mGFP fragments 1, 2, 3 and 4, and PCR was performed with the primers AS132 and AS133 to generate mGFP sequence with introns.

The generated aadA and mGFP sequences with introns were fused by digestion of aadA fragment with XmaI-BamHI enzymes, mGFP fragment with BamHI-XbaI enzymes and ligation in BlueScript SK digested with XmaI-XbaI enzymes. The resulting fusion fragment was then subsequently inserted in chloroplast cassette (FIG. 5).

Tnt1-RT-RH sequence (RT-RH)
(SEQ ID NO. 142)
ATGTCAGAAAAGGTGAAGAATGGTATAATTCCTAACTTTGTTACTATTCCTTCTACTTCTAACAATCCCACAA
GTGCAGAAAGTACGACCGACGAGGTTTCCGAGCAGGGGAGCAACCTGGTGAGGTTATTGAGCAGGGGGAGCA
ACTTGATGAAGGTGTCGAGGAAGTGGAGCACCCCACTCAGGGAGAAGAACAACATCAACCTCTGAGGAGATCA
GAGAGGCCAAGGGTAGAGTCACGCAGGTACCCTTCCACAGAGTATGTCCTCATCAGTGATGAGGGGGAGCCAG
AAAGTCTTAAGGAGGTGTTGTCCCATCCAGAAAAGAACCAGTGGATGAAAGCTATGCAAGAAGAGATGGAATC
TCTCCAGAAAAATGGCACATACAAGCTGGTTGAACTTCCAAAGGGTAAAAGACCACTCAAATGCAAATGGGTC
TTTAAACTCAAGAAAGATGGAGATGGCAAGCTGGTCAGATACAAAGCTCGATTGGTGGTTAAAGGCTTCGAAC
AGAAGAAAGGTATTGATTTTGACGAAATTTTCTCCCCCGTTGTTAAAATGACTTCTATTCGAACAATTTTGAG
CTTAGCAGCTAGCCTAGATCTTGAAGTGGAGCAGTTGGATGTGAAAACTGCATTTCTTCATGGAGATTTGGAA
GAGGAGATTTATATGGAGCAACCAGAAGGATTTGAAGTAGCTGGAAAGAAACACATGGTGTGCAAATTGAATA
AGAGTCTTTATGGATTGAAGCAGGCACCAAGGCAGTGGTACATGAAGTTTGATTCATTCATGAAAAGTCAAAC
ATACCTAAAGACCTATTCTGATCCATGTGTATACTTCAAAAGATTTTCTGAGAATAACTTTATTATATTGTTG
TTGTATGTGGATGACATGCTAATTGTAGGAAAAGACAAGGGGTTGATAGCAAAGTTGAAAGGAGATCTGTCCA
AGTCATTTGATATGAAGGACTTGGGCCCAGCACAACAAATTCTAGGGATGAAGATAGTTCGAGAGAGAACAAG
TAGAAAGTTGTGGCTATCTCAGGAGAAGTACATTGAACGTGTACTAGAACGCTTCAACATGAAGAATGCTAAG
CCAGTCAGCACACCTCTTGCTGGTCATCTAAAGTTGAGTAAAAAGATGTGTCCTACAACAGTGGAAGAGAAAG
GGAACATGGCTAAAGTTCCTTATTCTTCAGCAGTCGGAAGCTTGATGTATGCAATGGTATGTACTAGACCTGA
TATTGCTCACGCAGTTGGTGTTGTCAGCAGGTTTCTTGAAAATCCTGGAAAGGAACATTGGGAAGCAGTCAAG
TGGATACTCAGGTACCTGAGAGGTACCACGGGAGATTGTTTGTGCTTTGGAGGATCTGATCCAATCTTGAAGG
GCTATACAGATGCTGATATGGCAGGTGACATTGACAACAGAAAATCCAGTACTGGATATTTGTTTACATTTTC
AGGGGGAGCTATATCATGGCAGTCTAAGTTGCAAAAGTGCGTTGCACTTTCAACAACTGAAGCAGAGTACATT
GCTGCTACAGAAACTGGCAAGGAGATGATATGGCTCAAGCGATTCCTTCAAGAGCTTGGATTGCATCAGAAGG
AGTATGTCGTCTATTGTGACAGTCAAAGTGCAATAGACCTTAGCAAGAACTCTATGTACCATGCAAGGACCAA
ACACATTGATGTGAGATATCATTGGATTCGAGAAATGGTAGATGATGAATCTCTAAAAGTCTTGAAGATTTCT
ACAAATGAGAATCCCGCAGATATGCTGACCAAGGTGGTACCAAGGAACAAGTTCGAGCTATGCAAAGAACTTG
TCGGAATGCATTCAAACTAG The RT-RH fragment was amplified from tobacco genomic DNA following standard procedures using the following primers:

AS774
(SEQ ID NO. 143)
ggcatgcatgtcagaaaaggtga

AS775
(SEQ ID NO. 144)
gactagtctagtttgaatgcattccgacaagttct

Rubisco small subunit transit peptide sequence
(SEQ ID NO. 145)
ATGGCTTCCTCAGTTCTTTCCTCTGCAGCAGTTGCCACCCGCAGCAATGT
TGCTCAAGCTAACATGGTTGCACCTTTCACTGGCCTTAAGTCAGCTGCCT
CATTCCCTGTTTCAAGGAAGCAAAACCTTGACATCACTTCCATTGCCAGC
AATGGTGGAAGAGTGCAATGTATGCAGGTA Rubisco small subunit transit peptide sequence was amplified from tobacco genomic DNA using the following primers:

AS794
(SEQ ID NO. 146)
gctcgagacaatggcttcctcagttctttcctct

AS639
(SEQ ID NO. 147)
cgcatgctacctgcatacattgcactcttccaccat

The transit peptide was then fused to RT-RH (FIG. 7)

Primer Binding Site (PBS) sequence
(SEQ ID NO. 148)
TTGGTACCTACT

Primer binding site was introduced to trnA RFS by primer:

RFS-PBS-R
(SEQ ID NO. 149)
gccgcagtaggtaccaattgcccttctccgaccctgac.

Arabidopsis ubiquitin promoter (Ubiq3At)
(SEQ ID NO. 150)
CGGTACCTACCGGATTTGGAGCCAAGTCTCATAAACGCCATTGTGGAAGAAAGTCTTGAGTTGGTGGTAATGT

AACAGAGTAGTAAGAACAGAGAAGAGAGAGAGTGTGAGATACATGAATTGTCGGGCAACAAAAATCCTGAACA

TCTTATTTTAGCAAAGAGAAAGAGTTCCGAGTCTGTAGCAGAAGAGTGAGGAGAAATTTAAGCTCTTGGACTT

GTGAATTGTTCCGCCTCTTGAATACTTCTTCAATCCTCATATATTCTTCTTCTATGTTACCTGAAAACCGGCA

TTTAATCTCGCGGGTTTATTCCGGTTCAACATTTTTTTGTTTTGAGTTATTATCTGGGCTTAATAACGCAGG

CCTGAAATAAATTCAAGGCCCAACTGTTTTTTTTTTAAGAAGTTGCTGTTAAAAAAAAAAAAAGGGAATTAA

CAACAACAACAAAAAAAGATAAAGAAAATAATAACAATTACTTTAATTGTAGACTAAAAAAACATAGATTTTA

TCATGAAAAAAAGAGAAAAGAAATAAAAACTTGGATCAAAAAAAAAACATACAGATCTTCTAATTATTAACTT

TTCTTAAAAATTAGGTCCTTTTTCCCAACAATTAGGTTTAGAGTTTTGGAATTAAACCAAAAAGATTGTTCTA

AAAAATACTCAAATTTGGTAGATAAGTTTCCTTATTTTAATTAGTCAATGGTAGATACTTTTTTTTCTTTTCT

TTATTAGAGTAGATTAGAATCTTTTATGCCAAGTATTGATAAATTAAATCAAGAAGATAAACTATCATAATCA

ACATGAAATTAAAAGAAAAATCTCATATATAGTATTAGTATTCTCTATATATATTATGATTGCTTATTCTTAA

TGGGTTGGGTTAACCAAGACATAGTCTTAATGGAAAGAATCTTTTTTGAACTTTTTCCTTATTGATTAAATTC

TTCTATAGAAAAGAAAGAAATTATTTGAGGAAAAGTATATACAAAAAGAAAAATAGAAAAATGTCAGTGAAGC

AGATGTAATGGATGACCTAATCCAACCACCACCATAGGATGTTTCTACTTGAGTCGGTCTTTTAAAAACGCAC

GGTGGAAAATATGACACGTATCATATGATTCCTTCCTTTAGTTTCGTGATAATAATCCTCAACTGATATCTTC

CTTTTTTTGTTTTGGCTAAAGATATTTTATTCTCATTAATAGAAAAGACGGTTTTGGGCTTTTGGTTTGCGAT

ATAAAGAAGACCTTCGTGTGGAAGATAATAATTCATCCTTTCGTCTTTTTCTGACTCTTCAATCTCTCCCAAA

GCCTAAAGCGATCTCTGCAAATCTCTCGCGACTCTCTCTTTCAAGGTATATTTTCTGATTCTTTTTGTTTTTG

ATTCGTATCTGATCTCCAATTTTTGTTATGTGGATTATTGAATCTTTTGTATAAATTGCTTTTGACAATATTG

TTCGTTTCGTCAATCCAGCTTCTAAATTTTGTCCTGATTACTAAGATATCGATTCGTAGTGTTTACATCTGTG

TAATTTCTTGCTTGATTGTGAAATTAGGATTTTCAAGGACGATCTATTCAATTTTTGTGTTTTCTTTGTTCGA

TTCTCTCTGTTTTAGGTTTCTTATGTTTAGATCCGTTTCTCTTTGGTGTTGTTTTGATTTCTCTTACGGCTTT

TGATTTGGTATATGTTCGCTGATTGGTTTCTACTTGTTCTATTGTTTTATTTCAGGTCACCAAACACTCGAG

Promoter was amplified from Arabidopsis genomic DNA (Col-0) using the following primers:

AS724
(SEQ ID NO. 151)
CGGTACCTACCGGATTTGGAGCCAAGTC

AS726
(SEQ ID NO. 152)
GCTCGAGTGTTTGGTGACCTGAAATAAAACAATGAACAAGT

In conclusion we present an efficient system for chloroplast transformation using groupII intron-based vectors. Both bacterial and native introns could be utilised for delivery and insertion of transgene of interest into the chloroplasts.

Transformation of Tobacco Leaf Explants with *Agrobacterium* Strain AGL1

All items are autoclave-sterilised prior to use.

Filter sterilize antibiotics to prevent fungal growth and keep antibiotics for plant tissue culture in separate box.

Sterilize plant material: Take plants of about 9 cm high; they should not have started to flower. Cut leaves with cuticle (4-6 leaves per construct, enough to cut 100 explants), dip in 70% Ethanol and immediately dip in 1% Na-hypochlorite (cat. No 01032500; use bottle of bleach that is no more than 3 months old because the chlorine gas evaporates), hold leaves with forceps and stir in for 20 min. Avoid damaging the cuticle, otherwise bleach will enter the vascular system. Rinse briefly in sterile water 5-6 times and leave in water until ready to be cut.

Co-cultivation of agro with tobacco explants: Grow AGL1 in LB or L broth with appropriate antibiotics overnight at 28-30° C. and the next day re-suspend agro in co-cultivation solution so that the final concentration is around 0.4-0.6 $OD_{600\ nm}$. Place tobacco leaves in co-culture broth and cut squares of 1-1.5 cm×1-1.5 cm with a rounded sterile scalpel using a rolling action. Dip the leaf explants in the agro solution with sterile forceps (stored in 100% ethanol, flamed and let cool prior to touching the leaf tissue) blot on sterile Whatman paper and transfer onto non-selective TSM plates (6 explants per plate), preparing about 15 plates per construct. Repeat this procedure for each construct, making sure that the scalpel and forceps are dipped in ethanol and flamed between each construct to prevent cross-contamination. Leave for 2 days only for AGL1 (3-4 days for other agro strains).

Transfer onto selective TSM plates: Use sterile flamed forceps to pick up and wash explants in 100 mls co-cultivation broth supplemented with timentin 320 mg/l (one pot per construct), shake well, blot on sterile whatman paper and place the washed explants on selective TSM plates supplemented with appropriate selective antibiotics and timentin 320 mg/l to kill *agrobacterium*.

Shoot regeneration: Takes around 1 month to see shoots appear, explants should be transferred on fresh plates every 10-14 days. Watch for AGL1 recurrent growth; if Timentin is not enough to kill agro, add cefotaxime at 250 mg/l.

Root regeneration: Takes around 1 week. Shoots are cut from the explants; place in growth boxes containing TRM supplemented with the appropriate selective antibiotics and timentin 320 mg/l+cefotaxime 250 mg/l to prevent *agrobacterium* recurrent growth.

Maintain plants in TRM boxes: Sub them every two weeks until ready to be transferred into glasshouse Adaptation to glasshouse conditions: Soak peat pellets in sterile water until they swell to normal size and carefully place one plant per pellet, incubate the plants under 100% humidity conditions in a propagator, gradually opening the little windows until plants adapt to normal atmosphere over several days.

Recipes:
Co-culture: MS with vitamins and MES+0.1 mg/l NAA+1 mg/l BA+3% sucrose, pH 5.7
TSM: MS with vitamins and MES+0.1 mg/l NAA+1 mg/l BA+3% sucrose, pH5.7, 0.2% gelrite
TRM: ½ MS salts with vitamins and MES+0.5% sucrose, pH5.7, 0.2% gelrite.
Autoclave.
Antibiotics Concentration
For *Agrobacterium* LB or L Cultures:
To grow AGL1 carrying pGreen/pSOUP: Carbenicillin 100 mg/l Tetracycline 5 mg/ml, Rifampicin 50 mg/ml, Kanamycin 50 mg/ml
AGL1 carrying pSOUP: Carbenicilin 100 mg/l, Tetracycline 5 mg/ml, Rifampicin 50 mg/ml.
AGL1 empty: Carbenicillin 100 mg/l, Rifampicin 50 mg/ml.
For Plant Culture:
Kanamycin: 300 mg/l (100 mg/l if using benthamiana)
Hygromycin: 30 mg/l (10 mg/l if using benthamiana)
PPT: 20 mg/l (2 mg/l if using benthamiana)
Timentin: 320 mg/l. It is used to kill agro, but it is rather unstable. Make up small amount of stock and store in freezer for up to 1 month; after that the antibiotic is no longer efficient.
Cefotaxime: 250 mg/l. Also used to kill agro, add to TS Tomato Transformation Protocol Seed Germination
Surface Sterilisation
Give tomato seeds a 70% EtOH treatment for 2 minutes to loosen gelatinous seed coat.
Remove EtOH and rinse once with sterile water.
(At this stage you can include a 20 minute trisodium phosphate treatment to eliminate seed transmission of TMV). Rinse.
Add 10% Domestos/Vortex for 3 hours, shaking.
Wash 4 times with water. Leave in final change of water and shake at 25° C. overnight.

(The long bleach treatment and overnight imbibition are to encourage more even germination). Seeds may be left for up to 3 months at 4° C. Indeed after 3 weeks in a refrigerator, nearly all the seeds will germinate at the same time.

20-30 seeds are placed in tubs containing germination medium and left at 25° C. in culture room (16 hour photoperiod, supplemented with Gro-Lux or incandescent light, which is especially important for regeneration).

Seedlings are grown for 7-10 days. For transformation ideally cotyledons are young and still expanding, no true leaf formation is visible.

Transformation Procedure
Day 1
Morning; set up *Agrobacterium tumefaciens* culture
Inoculate 10 mls of minimal A medium containing the appropriate
antibiotics with LBA4404 strain. Grow shaking at 28° C.
Afternoon; set up feeder layers
Put 1 ml of fine tobacco suspension culture onto plates containing the cell suspension medium solidified with 0.6% agarose or MS medium with 0.5 mg/L 2,4-D, 0.6% agarose. Spread around to give an even layer. Place plates unsealed and stacked in the culture room in low light.
Day 2
Morning;
Incubation of Explants.
Place a Whatman no. 1 filter paper on top of the feeder plates. Take care to exclude any air bubbles and make sure the paper is completely wetted.
Cutting up plant material.
Cotyledons are used-hypocotyls give rise to a high number of tetraploids. Always cut under water and with a rolling action of a rounded scalpel blade to minimise damage to the tissue. In a petri dish cut off the tip of the cotyledon and then make two more transverse cuts to give two explants of about 0.5 cm long. Transfer the explants to a new petri dish of water to prevent any damage during further cutting. Always handle pieces with great care. The use of rounded forceps to scoop up the cut cotyledons helps prevent puncture with sharp tips.
Once a number of explants are collected in the pool, blot them on sterile filter paper and place about 30-40 on a feeder plate, abaxil surface uppermost (upside down). Place petri dishes unsealed and stacked at 25° C. under low light intensity.
Leave preincubating for 8 hours.
Afternoon; co-cultivation
Spin down *Agrobacterium* culture and resuspend pellet in MS medium 3% sucrose to an $OD_{600}$ of 0.4-0.5.
Put bacterial suspension in a petri dish and immerse the explants from one feeder plate. Remove them and blot on sterile filter paper before returning to the original feeder plate, again taking care not to damage the tissue. No particular period of time is required in the bacteria, but ensure that the pieces have been completely immersed. Return the plates to the same conditions as used in the preincubation phase.
Co-Cultivate for 40 Hours.
Day 4
Morning; apply selection
Take the pieces from the feeder layers and place on tomato regeneration plates containing Augmentin or carbenicillin at 500 ug/ml and the appropriate antibiotic to select for the T-DNA transformation marker, e.g. kanamycin at 100 ug/ml or preferably Augmentin since it may have a slight stimulatory effecton regeneration. Place the cotyledons right side upwards so that they curl into the medium ensuring good contact between the cut edges of the leaf with the nutrients and antibiotics.

Using Agar gel as the setting agent produces a soft medium into which the pieces can be pushed gently. Place 12 pieces per petri dish. Plates are left unsealed and returned to the culture room.

Week 2 or 3

Explants are transferred to fresh medium every 2-3 weeks. When regenerating material is too large for petri dishes it is placed on larger screw-capped glass jars, a petri dish lid replacing the plastic cap to allow better light penetration and better gas exchange.

Shoots are cut from the explants and placed in rooting medium with reduced antibiotic concentrations, Augmentin at 200 ug/ml and kanamycin at 5 ug/ml. If they do not root at first, re-cut and place in fresh medium. If they still fail to produce roots they are probably escapes. If using the kanamycin resistance gene as the selectable marker a simple npt II assay can be carried out to confirm the identity of true transformants.

To transfer to soil, remove as much of the medium as possible by washing the roots gently under running water. Plant carefully in hydrated, autoclaved Jiffy pots (peat pots) and keep enclosed to keep humidity high while in the growth room. Gradually decrease humidity. Once roots can be seen growing through the Jiffy-pots the plants are ready to go to the glasshouse.

N.B. 1 This protocol is used with the Moneymaker variety of tomato. Transformation efficiencies with other varieties may be lower using these conditions and alterations in preincubation period, density of the *Agrobacterium* suspension and the length of the period of co-cultivation may be necessary to optimise the protocol for any particular variety.

N.B. 2 One difficulty that may arise, especially if the transgenic plants are required for seed production, is that of tetraploidy. It seems that a significant proportion of regenerants may have a doubled chromosome number. This can be assessed, either by chloroplast number in guard cells or by chromosome counts.

| REGENERATION | |
|---|---|
| | /Liter |
| MS salts | 1x |
| myo-inositol | 100 mg |
| Nitsch's vitamins | 1 ml of 1000X stock |
| Sucrose | 20 g |
| Agargel | 4 g |
| pH 6.0 (KOH) | |
| Autoclave | |
| Zeatin Riboside (trans isomer) | 2 mg |

(Filter sterilise and add after autoclaving)

| Nitsch's Vitamins | | |
|---|---|---|
| | Final conc. | |
| | mg/l | 1000x stock (mg/100 ml) |
| Thiamine | 0.5 | 50 |
| Glycine | 2.0 | 200 |
| Nicotinic acid | 5.0 | 500 |
| Pyridoxine HCl | 0.5 | 50 |
| Folic acid | 0.5 | 50 |
| Biotin | 0.05 | 5 |

At 1000x not all vitamins go into solution. Keep at 4° C. and shake before using.

| Rooting | |
|---|---|
| | g/Liter |
| MS medium | 0.5X |
| Sucrose | 5 g |
| Gelrite | 2.25 g |
| pH 6.0 (KOH) | |

Media

| Seed Germination | |
|---|---|
| | /Liter |
| MS medium | 1x |
| Glucose | 10 g |
| Agarose | 6 g |
| pH 5.8 | |
| Pour into round Sigma 'margarine' tubs. | |

| Minimal A | |
|---|---|
| | /Liter |
| $K_2HPO_4$ | 10.5 g |
| $KH_2PO_4$ | 4.5 g |
| $(NH_4)_2SO_4$ | 1.0 g |
| Na citrate•$2H_2O$ | 0.5 g |

Autoclave in 990 ml
Before use add; 1.0 ml of 1M $MgSO_4.H_2O$
10 ml of 20% Glucose
For plates;
Make the above in 500 ml and autoclave.
Separately autoclave 15 g Bactoagar in 490 ml $H_2O$
Add $MgSO_4$ and glucose and combine.
Transformation of Rice Immature Embryos.
Immature Embryo Excision
Day 1:
Remove milky/post-milky stage immature seeds from panicles (immature embryos 1-2 mm in size are desired).
Sterilize immature seeds: 50% sodium hypochlorite (12%)+1 drop of tween 20. Shake 10 min.
Rinse 3-5× in sterile deionised water. Drain off surplus water. Aliquot seeds (around 40) in sterile Petri dishes.
Set up a 60×15 mm Petri dish containing a 50% sodium hypochlorite solution and next to this a sterile beaker on its side with a sterile filter paper in it. Use sterile forceps to aseptically remove glumes from the first seed. Immerse this seed in the 50% sodium hypochlorite. Remove glumes from a second seed and immerse the second seed into the sodium hypochlorite solution whilst removing the first seed and storing this dehusked/sterilized seed on the filter paper in the beaker. Continue.

After all the glumes are removed:

Sterilize dehusked seeds: 50% sodium hypochlorite: 5 min. with agitation.

Rinse: 5-7× in sterile deionized water, drain.

Place all seeds in a large sterile Petri dish. Aliquot for embryo excision (to keep seeds from drying out, work with only 50-100 in the plate at a time leaving the rest in the master plate).

Remove the embryo from each seed and place embryo, scutellum up, in a 90×15 mm Petri dish containing proliferation medium (40-50 embryos/plate). Culture at 28° C. in the dark for 2 days prior to bombardment Day 3:

Check each embryo for contamination before blasting

Remove the embryos from the proliferation medium. Distribute 35-40 embryos scutellum upwards in an area 1 cm² in the centre of a 60×15 mm target plate containing 10 ml of proliferation medium+osmoticum (0.6M).

Check each target plate so that the scutellum is straight. Allow enough room so the scutella do not shade each other out.

Bombardment:

| Gun | 14 kV |
|---|---|
| | Vacuum: 25 inches of Hg |
| 1$^{st}$ bombardment | 4 hours after osmoticum treatment |
| 2$^{nd}$ bombardment | 4 hours after 1$^{st}$ bombardment |

Day 4:

4-16 hours after the 2nd blast transfer immature embryos to proliferation medium without osmoticum. Culture in the dark at 28° C. for 2 days.

Selection:

Day 5:

Aseptically cut out with scissors the germinating shoot. Transfer 16-20 immature embryos to fresh proliferation medium containing 30-50 mg/l Hygromycin (depending on the genotype); culture in the dark at 28° C.; record total number of embryos.

After 10 days carefully remove the callus from the scutellum by breaking it up into 2-10 small pieces; subculture onto fresh proliferation medium+hygromycin. Do not subculture brown tissue and remaining immature embryo which could inhibit further growth of healthy callus.

Subculture every 10 days by selecting healthy tissue: (embryogenic if present) and transfer it to fresh proliferation medium+hygromycin. Remove brown callus as it could be inhibiting to embryogenic callus.

30 to 40 days after bombardment change selection procedure. Instead of eliminating bad-looking tissue keep embryogenic tissue only (eliminate healthy non-embryogenic tissue)

Regeneration:

After 40 to 60 days, transfer established embryogenic callus showing differential growth on proliferation medium+hygromycin to regeneration medium+hygromycin. Culture at 28° C. under low light for 10 days then under high light for 10 additional days. Check plates periodically in the light for the development of embryos and green shoots. As shoots develop it is sometimes beneficial to gently move the developing shoot away from the callus it originated from and remove any dead tissue from the shoot itself to prevent inhibition of growth.

Germination:

Transfer white compact embryos and green shoots initiating roots to the germination medium under high light at 28° C. for 1 to 2 weeks. Check plates periodically. Remove necrotic tissue and divide germinating embryos if necessary.

The invention claimed is:

1. A method of producing at least a heterologous or exogenous polypeptide in a plant or plant cell wherein said method comprises:
   1) introducing into the nucleus of the plant cell a DNA construct comprising a plant nuclear promoter operably linked to a group II intron selected from the group consisting of the LtrB intron from *Lactococcus lactis* and a trnK intron of a plant, wherein the group II intron comprises a plastid transgene cassette inserted in Domain IV of said group II intron operably linked to a primer binding domain (PBD),
      a) said plastid transgene cassette comprising a left flanking sequence, a plastid specific promoter, a nucleic acid of interest that encodes a heterologous or exogenous polypeptide, a plastid specific terminator, and a right flanking sequence;
   2) introducing into the nucleus of the plant cell a second DNA construct comprising a plant nuclear promoter operably linked to a polynucleotide encoding a plastid transit peptide sequence fused to an intron encoded protein selected from the group consisting of LtrA when the introduced intron is LtrB and MatK when the introduced intron is trnK;
   3) growing said plant cells of 1) and 2) under conditions expressing the first and second DNA constructs;
   4) selecting a plant cell of 3) comprising said plastid transgene cassette integrated into the plastid genome;
   5) growing the plant cell of 4) or a plant regenerated therefrom under conditions wherein said plant plastid promoter expresses said heterologous or exogenous polypeptide from said plastid transgene cassette.

2. The method according to claim 1, wherein the nucleic acid sequence that encodes the intron encoded protein is a bacterial LtrA nucleic acid sequence that is codon optimized for expression in plants.

3. The method according to claim 1, wherein the plant plastid is selected from the group consisting of chloroplasts, proplastids, etioplasts, chromoplasts, amyloplasts, leucoplasts and elaioplasts.

4. The method according to claim 3, wherein the plant plastid is a chloroplast.

5. The method according to claim 1, wherein the heterologous or exogenous polypeptide is at least one selected from the group consisting of insulin, preproinsulin, proinsulin, glucagon, interferons, Factor VII, Factor VIII, Factor IX, Factor X, Factor XI, Factor XII, fertility hormones, follicle stimulating hormone growth factors, platelet-derived growth factor, granulocyte colony stimulating factor, prolactin, oxytocin, thyroid stimulating hormone, adrenocorticotropic hormone, calcitonin, parathyroid hormone, somatostatin, erythropoietin (EPO), enzymes, hemoglobin, serum albumin, collagen, insect toxic proteins from *Bacillus thuringiensis*, herbicide resistance proteins, salt-tolerance proteins, and edible vaccines.

6. The method according to claim 1, wherein the plant nuclear promoter is selected from the group consisting of inducible, chemically regulated, constitutive, and tissue specific promoters.

7. The method according to claim 1, wherein the plant plastid promoter is selected from the group consisting of a RNA polymerase promoter, a rpo B promoter element, a atpB promoter element, a clpP promoter element, a 16S rDNA promoter element, a PrbcL promoter, a Prps16 promoter, a Prrn16 promoter, a Prrn-62 promoter, a Pycf2-1577 promoter, a PatpB-289 promoter, a Prps2-152 promoter, a Prps16-107 promoter, a Pycf1-41 promoter, a PatpI-207 promoter, a PclpP-511 promoter, a PclpP-173 promoter, a PaccD-129 promoter, a PaccD-129 promoter of the tobacco accD gene, a PclpP-53 promoter of the clpP gene, a Prrn-62 promoter of the rrn gene, a Prps16-107 promoter of the rps16 gene, a PatpB/E-290 promoter of the tobacco atpB/E gene, and a PrpoB-345 promoter of the rpoB gene.

8. The method according to claim 1, wherein the primer binding site is homologous to the 3'-end of a chloroplast specific tRNA.

9. A polynucleotide construct comprising a plant nuclear promoter operably linked to a group II intron selected from the group consisting of the LtrB intron from *Lactococcus lactis* and a trnK intron of a plant, wherein the group II intron comprises a plastid transgene cassette inserted in Domain IV of said group II intron operably linked to a primer binding domain (PBD),
   a) said plastid transgene cassette comprising a left flanking sequence, a plastid specific promoter, a nucleic acid of interest that encodes a heterologous or exogenous polypeptide, a plastid specific terminator, and a right flanking sequence.

10. The isolated polynucleotide according to claim 9, comprising genomic DNA.

11. The isolated polynucleotide according to claim 9, comprising a cDNA component.

12. A polynucleotide construct comprising a plant nuclear promoter operably linked to a polynucleotide encoding a plastid transit peptide sequence fused to an intron encoded protein selected from the group consisting of LtrA and MatK.

13. A host cell containing the isolated polynucleotide according to claim 9.

14. The host cell according to claim 13, wherein the host cell is comprised in a plant, a plant part, a plant propagule, or a plant cell culture.

15. A plant comprising a plant cell, wherein said plant cell is the host cell according to claim 13.

16. The plant according to claim 15, wherein the plant is selected from the group consisting of cotton, rice, oilseed, corn, and soybean.

17. The method according to claim 5, wherein the heterologous or exogenous polypeptide is at least one selected from the group consisting of α-interferon, β-interferon, γ-interferon, β-glucocerebrosidase, luteinizing hormone, and epidermal growth factor.

18. The method according to claim 1, wherein the heterologous or exogenous polypeptide is a nutritional enhancement protein involved in the biosynthesis of phenolics, starches, sugars, alkaloids, or vitamins.

\* \* \* \* \*

SEQUENCE LISTING

```
<160> NUMBER OF SEQ ID NOS: 155

<210> SEQ ID NO 1
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 1
tgtctcgagt gtgattgcaa cccacgtcga t                          31

<210> SEQ ID NO 2
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 2
tgtggcgcgc cacgcgtcgc cacgtaataa ata                        33

<210> SEQ ID NO 3
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 3
```

```
tgtgcggccg ctgggaaatg gcaatgatag cga                          33
```

<210> SEQ ID NO 4
<211> LENGTH: 35
<212> TYPE: DNA
<213> ORGANISM: Artificial sequence
<220> FEATURE:
<223> OTHER INFORMATION: Synthetic sequence: Primer

<400> SEQUENCE: 4

```
tgtgaattcc agtcaaattg tttgccagta taaag                        35
```

<210> SEQ ID NO 5
<211> LENGTH: 749
<212> TYPE: DNA
<213> ORGANISM: Lactococcus lactis

<400> SEQUENCE: 5

```
ctcgagtgtg attgcaaccc acgtcgatcg tgaacacatc cataacgtgc gcccagatag    60
ggtgttaagt caagtagttt aaggtactac tctgtaagat aacacagaaa acagccaacc   120
taaccgaaaa gcgaaagctg atacgggaac agagcacgtg tggaaagcga tgagttacct   180
aaagacaatc gggtacgact gagtcgcaat gttaatcaga tataaggtat aagttgtgtt   240
tactgaacgc aagtttctaa tttcggttat gtgtcgatag aggaaagtgt ctgaaacctc   300
tagtacaaag aaaggtaagt tatggttgtg gacttatctg ttatcaccac atttgtacaa   360
tctgtaggag aacctatggg aacgaaacga aagcgatgcc gagaatctga atttaccaag   420
acttaacact aactggggat accctaaaca agaatgccta atagaaagga ggaaaaaggc   480
tatagcacta gagcttgaaa atcttgcaag ggtacggagt actcgtagta gtctgagaag   540
ggtaacgccc tttacatggc aaaggggtac agttattgtg tactaaaatt aaaaattgat   600
tagggaggaa aacctcaaaa tgaaaccaac aatggcaatt ttagaaagaa tcagtaaaaa   660
ttcacaagaa aatatagacg aagttttttac aagactttat cgttatcttt tacgtccaga   720
tatttattac gtggcgacgc gtggcgcgc                                     749
```

<210> SEQ ID NO 6
<211> LENGTH: 270
<212> TYPE: DNA
<213> ORGANISM: Lactococcus lactis

<400> SEQUENCE: 6

```
gcggccgctg ggaaatggca atgatagcga acaacgtaa aactcttgtt gtatgctttc    60
attgtcatcg tcacgtgatt cataaacaca agtgaatttt tacgaacgaa caataacaga   120
gccgtatact ccgagagggg tacgtacggt tcccgaagag ggtggtgcaa accagtcaca   180
gtaatgtgaa caaggcggta cctccctact tcaccatatc attttttaatt ctacgaatct   240
ttatactggc aaacaatttg actggaattc                                    270
```

<210> SEQ ID NO 7
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 7

```
ggcatgcatg aaaccaacaa tggcaatttt a                            31
```

```
<210> SEQ ID NO 8
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 8
gactagttca cttgtgttta tgaatcacgt g                                 31

<210> SEQ ID NO 9
<211> LENGTH: 1812
<212> TYPE: DNA
<213> ORGANISM: Lactococcus lactis

<400> SEQUENCE: 9
gcatgcatga aaccaacaat ggcaatttta gaaagaatca gtaaaaattc acaagaaaat    60
atagacgaag tttttacaag actttatcgt tatcttttac gtccagatat ttattacgtg   120
gcgtatcaaa atttatattc aataaaagga gcttccacaa aaggaatatt agatgataca   180
gcggatggct ttagtgaaga aaaaataaaa aagattattc aatctttaaa agacggaact   240
tactatcctc aacctgtacg aagaatgtat attgcaaaaa agaattctaa aaagatgaga   300
cctttaggaa ttccaacttt cacagataaa ttgatccaag aagctgtgag ataattctt    360 gaatctatct atgaaccggt attcgaagat gtgtctcacg ttttagacc tcaacgaagc    420 tgtcacacag ctttgaaaac aatcaaaaga gagtttggcg gcgcaagatg gtttgtggag   480
ggagatataa aaggctgctt cgataatata gaccacgtta cactcattgg actcatcaat   540
cttaaaatca agatatgaa atgagccaa tgatttata aatttctaaa agcaggttat     600
ctggaaaact ggcagtatca caaaacttac agcggaacac tcaaggtgg aattctatct   660 cctcttttgg ccaacatcta tcttcatgaa ttggataagt ttgttttaca actcaaaatg   720
aagtttgacc gagaaagtcc agaaagaata cacctgaat ctcgggaact tcacaatgag    780
ataaaaagaa tttctcaccg tctcaagaag ttggagggtg aagaaaaagc taaagttctt   840
ttagaatatc aagaaaaacg taaaagatta cccacactcc cctgtacctc acagacaaat   900
aaagtattga atacgtccg gtatgcggac gacttcatta tctctgttaa aggaagcaaa   960
gaggactgtc aatggataaa agaacaatta aaacttttta ttcataacaa gctaaaaatg   1020
gaattgagtg aagaaaaac actcatcaca catagcagtc aacccgctcg ttttctggga   1080
tatgatatac gagtaaggag aagtggaacg ataaaacgat ctggtaaagt caaaagagag   1140
acactcaatg ggagtgtaga actccttatt cctcttcaag acaaaattcg tcaatttatt   1200
tttgacaaga aaatagctat ccaaaagaaa gatagctcat ggtttccagt tcacaggaaa   1260
tatcttattc gttcaacaga cttagaaatc atcacaattt ataattctga attaagaggg   1320
atttgtaatt actacggtct agcaagtaat tttaaccagc tcaattattt tgcttatctt   1380
atggaataca gctgtctaaa aacgatagcc tccaaacata agggaacact ttcaaaaacc   1440
atttccatgt ttaaagatgg aagtggttcg tggggcatcc cgtatgagat aaagcaaggt   1500
aagcagcgcc gttattttgc aaattttagt gaatgtaaat ccccttatca atttacggat   1560
gagataagtc aagctcctgt attgtatggc tatgcccgga atactcttga aaacaggtta   1620
aaagctaaat gttgtgaatt atgtggaaca tctgatgaaa atacttccta tgaaattcac   1680
catgtcaata aggtcaaaaa tcttaaaggc aaagaaaat gggaaatggc aatgatagcg    1740
aaacaacgta aaactcttgt tgtatgcttt cattgtcatc gtcacgtgat tcataaacac   1800
```
aagtgaacta gt         1812

<210> SEQ ID NO 10
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 10
tctcgagttg atggcttctt ctgctcaaat a         31

<210> SEQ ID NO 11
<211> LENGTH: 29
<212> TYPE: DNA
<213> ORGANISM: Artificial sequence
<220> FEATURE:
<223> OTHER INFORMATION: Synthetic sequence: Primer

<400> SEQUENCE: 11
ggcatgcaac tctcaaagtg aaacccttc         29

<210> SEQ ID NO 12
<211> LENGTH: 207
<212> TYPE: DNA
<213> ORGANISM: Pisum sativum

<400> SEQUENCE: 12
ctcgagatgg cttcttctgc tcaaatacac ggtctcggaa ccgcttcttt ctcttccctc         60
aaaaaaccct cttccatttc cggtaattcc aaaacccttt tcttcggtca gcgactcaat        120
tccaaccact ctcccttcac ccgcgccgca ttccctaagt taagtagcaa aacctttaag        180
aagggtttca ctttgagagt tgcatgc         207

<210> SEQ ID NO 13
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 13
gctcgaggtt gctaactcaa cggtagagta c         31

<210> SEQ ID NO 14
<211> LENGTH: 38
<212> TYPE: DNA
<213> ORGANISM: Artificial sequence
<220> FEATURE:
<223> OTHER INFORMATION: Synthetic sequence: Primer

<400> SEQUENCE: 14
gcacgcgtgg cgcgccattt ctatttaaac catgatca         38

<210> SEQ ID NO 15
<211> LENGTH: 37
<212> TYPE: DNA
<213> ORGANISM: Artificial sequence
<220> FEATURE:
<223> OTHER INFORMATION: Synthetic sequence: Primer

<400> SEQUENCE: 15
cacgcgtgcg gccgcttctt ctagtttgtg gggagta         37

<210> SEQ ID NO 16
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 16

```
gggatccgat atgctagtgg gttgcccggg a                              31
```

<210> SEQ ID NO 17
<211> LENGTH: 837
<212> TYPE: DNA
<213> ORGANISM: Nicotiana tabacum

<400> SEQUENCE: 17

```
gtgcggctag tctctttta c acatatggat gaagtgaggg attcgtccat actctcggta    60
aagtttggaa gaccacgact gatcctgaaa gggaatgaat ggtaaaaata gcatgtcgta   120
tcaacggaaa gttctgagaa tatttcattg ttcctagatg ggtataaaac cgtgttagaa   180
ttcttggaac ggaacaaaat aaagttgggt cgaatgaata aatggatagg gctgcggctt   240
caattaaatt atagggaaag aaagaaaaag caacgagctt tgttcttaa tttgaatgat    300 tcccgatcta attagacgtt aaaaatttat tagtgcctga tgcgggaagg gtttcttgtc   360
ccatgagtgg attctccatt tttttaatga atcctaacta ttaccatttt ctattacgga   420
gatgtgtgtg tagaagaaac agtatattga taaagaaagt ttttccgaa gtcaaaagag    480 cgattaggtt gaaaaaataa aggatttcta accatcttat tatcctataa cactataaca   540
tagaccaatt aaacgaaacg aaaaaaaaaa gagatgatag agaatccgtt gagaagttta   600
cctgtatcca aggtatctat tcttactaaa atactttgtt ttaactgtat cgcactatgt   660
atcatttgat aaccctcaaa atcttccgtc tttggttcaa atcgaatttc aaatggaaga   720
aatccaaaga tatttacagc cagatagatc gcaacaacac aacttcctat atccacttat   780
ctttcaggag tatatttatg cacttgctca tgatcatggt ttaaatagaa atgcgcc      837
```

<210> SEQ ID NO 18
<211> LENGTH: 369
<212> TYPE: DNA
<213> ORGANISM: Nicotiana tabacum

<400> SEQUENCE: 18

```
ttcttctagt ttgtggggag tatatagaag tcggatttgg tatttggata ttttttgtat    60
caatgatctg gcgaattatc aatgattcat tcttagattt tctaaatgga aatttgtttc   120
taaatgatga agagataaaa aaatttcact attctgaaat gttgattgta atagtaatta   180
aggggtaaat caactgagta ttcaactttt taaagtcttt ctaatttcta taagaaagga   240
actgatgtat acatagggaa agccgtgtgc aatgaaaaat gcaagcacgg cttggggagg   300
ggtctttact tgtttattta atttaagatt aacatttatt ttatttaaca aggaacttat   360
ctactccat                                                           369
```

<210> SEQ ID NO 19
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 19

```
ggcatgccaa atggaagaaa tccaaagata                                         30
```

<210> SEQ ID NO 20
<211> LENGTH: 29
<212> TYPE: DNA
<213> ORGANISM: Artificial sequence
<220> FEATURE:
<223> OTHER INFORMATION: Synthetic sequence: Primer

<400> SEQUENCE: 20

```
ggagctctca ttgataattc gccagatca                                          29
```

<210> SEQ ID NO 21
<211> LENGTH: 1545
<212> TYPE: DNA
<213> ORGANISM: Nicotiana tabacum

<400> SEQUENCE: 21

```
gcatgccaaa tggaagaaat ccaaagatat ttacagccag atagatcgca acaacacaac         60
ttcctatatc cacttatctt tcaggagtat atttatgcac ttgctcatga tcatggttta        120
aatagaaata ggtcgatttt gttggaaaat ccaggttata acaataaatt aagtttccta        180
attgtgaaac gtttaattac tcgaatgtat caacagaatc attttcttat ttctactaat        240
gattctaaca aaaattcatt tttggggtgc aacaagagtt tgtattctca atgatatca         300
gagggatttg cgtttattgt ggaaattccg ttttctctac gattaatatc ttctttatct        360
tctttcgaag gcaaaaagat ttttaaatct tataatttac gatcaattca ttcaacattt        420
cctttttttag aggacaattt ttcacatcta aattatgtat tagatatact aatacccac        480
cctgttcatc tggaaatctt ggttcaaact cttcgctatt gggtaaaaga tgcctcttct        540
ttacatttat tacgattctt tctccatgaa ttttggaatt tgaatagtct tattacttca        600
aagaagcccg ttactccctt tcaaaaaaaa atcaaagat tcttcttctt cttatataat         660
tcttatgtat atgaatgcga atccactttc gtctttctac ggaaccaatc ttctcattta        720
cgatcaacat cttttggagc ccttcttgaa cgaatatatt tctatggaaa aatagaacgt        780
cttgtagaag tctttgctaa ggattttcag gttaccctat ggttattcaa ggatcctttc        840
atgcattatg ttaggtatca aggaaaatcc attctggctt caaaagggac gtttcttttg        900
atgaataaat ggaaatttta ccttgtcaat ttttggcaat gtcattgttc tctgtgcttt        960
cacacaggaa ggatccatat aaaccaatta tccaatcatt cccgtgactt tatgggctat       1020
ctttcaagtg tgcgactaaa tccttcaatg gtacgtagtc aaatgttaga aaattcatt        1080
ctaatcaata atgcaattaa gaagttcgat acccttgttc caattattcc tttgattgga       1140
tcattagcta aagcaaactt ttgtaccgta ttagggcatc ccattagtaa accggtttgg       1200
tccgatttat cagattctga tattattgac cgatttgggc gtatatgcag aaatctttt        1260
cattattata gcggatcttc caaaaaaaag actttatatc gaataaagta tatacttcga       1320
ctttcttgtg ctagaacttt agctcggaaa cacaaaagta ctgtacgcac ttttttgaaa       1380
agatcgggct cggaattatt ggaagaattc ttaacgtcgg aagaacaagt tctttctttg       1440
accttcccac gagcttcttc tagtttgtgg ggagtatata gaagtcggat ttggtatttg       1500
gatatttttt gtatcaatga tctggcgaat tatcaatgag agctc                      1545
```

<210> SEQ ID NO 22
<211> LENGTH: 28
<212> TYPE: DNA

```
<213> ORGANISM: Artificial sequence
<220> FEATURE:
<223> OTHER INFORMATION: Synthetic sequence: Primer

<400> SEQUENCE: 22
gctcgagact gtagtggttg gtgtattg                                         28

<210> SEQ ID NO 23
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 23
gggcgcgcct tcttttttgt tatgtattat ggct                                  34

<210> SEQ ID NO 24
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 24
ggcggccgca aaaggagcg ggagagccaa a                                      31

<210> SEQ ID NO 25
<211> LENGTH: 29
<212> TYPE: DNA
<213> ORGANISM: Artificial sequence
<220> FEATURE:
<223> OTHER INFORMATION: Synthetic sequence: Primer

<400> SEQUENCE: 25
gactagtgaa tagtacttaa aatcctctg                                        29

<210> SEQ ID NO 26
<211> LENGTH: 787
<212> TYPE: DNA
<213> ORGANISM: Zea mays

<400> SEQUENCE: 26
ctcgagactg tagtggttgg tgtattgatt ttttttggaa agggagtgtg tgcgagttgt       60
ctatttcaag aatagattgg atctatccgg ctgcacttta gaatattttt agtatttttt      120
ttgataaata agaaaaggtg cacgatctcg acgaattact tctgaataac ttcagaaatc      180
atatggaaga accatagcat ttcgcgattc attggtaaat ttactttgat tctctataga      240
ccaataatgt gagaccatta acacggttaa agctaaactg cttgaagtcc gggcaaaaag      300
gggtactctt tctacaacta cattagtatt agtctcgaaa tgctttaaac gggaaatagc      360
tagtgtagaa tttatctgat atagaacact catatcgata aaatagtttg aactatttac      420
tagaagggca cgcagccctt tttccaatgc caaatcgacg acctatgtat aaaaaaaaga      480
gaaatttttt ggatttgaag aaaaaataaa aggaattcta tcaattttta ttttccattt      540
atttagttag ttttttcttaa tgaaattgaa attattaact aacagagcaa acacaaataa      600
agaaacaact ttgctgacca tgatagattt ttatctagtt ggaagagtcc tcttaatatt      660
catctagtct tatataagtt tgggtatata gaaatacaaa cagaaaagag aggatagagg      720
ataggctcat tacataaaaa aaagatatgg aaatagccat aatacataac aaaaaagaag      780
gcgcgcc                                                               787
```

<210> SEQ ID NO 27
<211> LENGTH: 162
<212> TYPE: DNA
<213> ORGANISM: Zea mays

<400> SEQUENCE: 27
gcggccgcaa aaaggagcgg gagagccaaa tgaatcgaaa gattcatgtt tggttcggga      60
agagatcata aaaattgtaa acttaatagc aagataatct actttcatta aaagatttat    120
tagataatcg aaaacagagg attttaagta ctattcacta gt                        162

<210> SEQ ID NO 28
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 28
ggtcgacgga tacttctctt caacttcgaa gt                                    32

<210> SEQ ID NO 29
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 29
gactagtacg cgggttcccc ataataatta tg                                    32

<210> SEQ ID NO 30
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 30
gggcgcgcca taatgactca atgactcaag gta                                   33

<210> SEQ ID NO 31
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 31
ggcggccgca tacccctatt ctattgtgga tc                                    32

<210> SEQ ID NO 32
<211> LENGTH: 716
<212> TYPE: DNA
<213> ORGANISM: Zea mays

<400> SEQUENCE: 32
gtcgacggat acttctcttc aacttcgaag tattttttata caaatagttg aagtgaattt     60
tacgaaagaa aataaggcgg attatgggag tgtgtgactt gaattattaa tttggccatg    120
cagatagaga attggatctg ccacattaga attcacgacc aaaggtgtct ccgcatccaa    180
tcaacacgta agtcccctat ctaggaagga taggctggtt cactcgagga gaatattttc    240

```
tatgatcata ccccaccaac catgtcatcc atgaacaggc tccgtaagat cctatagagt      300
ataaatggaa taagtcatgt gatatgatcc aattcaattt ttattacact tacttttat       360 tatagtatgg aaatgcattc attttctttg catcgatttt gatccgcaat actatcggag      420
taaaagaagg gatctaagga agaacgcagg ctaaacttttt tgattttta ttagtaacaa      480 gtaaatactt tgtttggaca taagaaactt gcgatatcga ggggataaac aacaactaat      540
caagagacaa tccacaaagc aattgatcat gatcaaattt gtaagcccac ttggatattg      600
agcatttaag cataagaata ggattctttt caatgagtag ttataggcgc aacttcggaa      660
aagataattt gataaagttt ttcttacctt gagtcattga gtcattatgg cgcgcc         716
```

<210> SEQ ID NO 33
<211> LENGTH: 227
<212> TYPE: DNA
<213> ORGANISM: Zea mays

<400> SEQUENCE: 33

```
gcggccgcat acccctattc tattgtggat cctccacggt cttatttctt tcattcttgc      60
tcgagccgga tgatgaaaaa ttctcatgtc cggttccttt ggggatgga tcctaaagaa       120 ttcacctatc ccaataacaa agaaacctga cttaaatgat cctgtattaa gagcaaaatt     180
agctaaaggg atgggacata attattatgg ggaacccgcg tactagt                   227
```

<210> SEQ ID NO 34
<211> LENGTH: 150
<212> TYPE: DNA
<213> ORGANISM: Nicotiana tabacum

<400> SEQUENCE: 34

```
ctcgagtttg ctcccccgcc gtcgttcaat gagaatggat aagaggctcg tgggattgac      60 gtgaggggc agggatggct atatttctgg gagcgaactc cgggcgaata cgaagcgctt      120
ggatacagtt gtagggaggg atttcccggg                                      150
```

<210> SEQ ID NO 35
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 35

```
tctcgagttt gctcccccgc cgtcgttc                                         28
```

<210> SEQ ID NO 36
<211> LENGTH: 36
<212> TYPE: DNA
<213> ORGANISM: Artificial sequence
<220> FEATURE:
<223> OTHER INFORMATION: Synthetic sequence: Primer

<400> SEQUENCE: 36

```
ccccgggccc tccctggagt tcgctcccag aaatat                                36
```

<210> SEQ ID NO 37
<211> LENGTH: 221
<212> TYPE: DNA
<213> ORGANISM: Triticum aestivum

<400> SEQUENCE: 37

```
ccgcggcatt catatgatag aatatgggtt taaataaatt ggctctttgc ggagtctttc      60
``` ccgataaaata cttaatttct tttattcata ttctccata gatagcaaag caagtttgaa    120
ttagtataca aaaaacgaaa ctaatgacta ttcatgattc catccatatt ggatcaattc    180
cctataacac tttgcaatga aattagagga atgttatcga t                       221

<210> SEQ ID NO 38
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 38
gccgcggcat tcatatgata gaatatgggt                                     30

<210> SEQ ID NO 39
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 39
tatcgataac attcctctaa tttcattgca                                     30

<210> SEQ ID NO 40
<211> LENGTH: 804
<212> TYPE: DNA
<213> ORGANISM: Escherichia coli

<400> SEQUENCE: 40
cccgggatga gggaagcggt gatcgccgaa gtatcgactc aactatcaga ggtagttggc     60
gtcatcgagc gccatctcga accgacgttg ctggccgtac atttgtacgg ctccgcagtg    120
gatggcggcc tgaagccaca cagtgatatt gatttgctgg ttacggtgac cgtaaggctt    180
gatgaaacaa cgcggcgagc tttgatcaac gaccttttgg aaacttcggc ttcccctgga    240
gagagcgaga ttctccgcgc tgtagaagtc accattgttg tgcacgacga catcattccg    300
tggcgttatc cagctaagcg cgaactgcaa tttggagaat ggcagcgcaa tgacattctt    360
gcaggtatct tcgagccagc cacgatcgac attgatctgg ctatcttgct gacaaaagca    420 agaaacata gcgttgcctt ggtaggtcca gcggcgagg aactctttga tccggttcct    480
gaacaggatc tatttgaggc gctaaatgaa accttaacgc tatggaactc gccgcccgac    540
tgggctggcg atgagcgaaa tgtagtgctt acgttgtccc gcatttggta cagcgcagta    600
accggcaaaa tcgcgccgaa ggatgtcgct gccgactggg caatggagcg cctgccggcc    660
cagtatcagc ccgtcatact tgaagctaga caggcttatc ttggacaaga agaagatcgc    720
ttggcctcgc gcgcagatca gttggaagaa tttgtccact acgtgaaagg cgagatcacc    780
aaggtagtcg gcaaatcagg atcc                                           804

<210> SEQ ID NO 41
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 41
gcccgggatg agggaagcgg tgatcgccga                                     30

<210> SEQ ID NO 42
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 42
gggatcctga tttgccgact accttggt                                     28

<210> SEQ ID NO 43
<211> LENGTH: 729
<212> TYPE: DNA
<213> ORGANISM: Artificial sequence
<220> FEATURE:
<223> OTHER INFORMATION: Synthetic construct; mGFP4 gene

<400> SEQUENCE: 43
ggatccatga gtaaaggaga agaacttttc actggagttg tcccaattct tgttgaatta    60
gatggtgatg ttaatgggca caaattttct gtcagtggag agggtgaagg tgatgcaaca   120
tacggaaaac ttacccttaa atttatttgc actactggaa aactacctgt tccatggcca   180
acacttgtca ctactttctc ttatggtgtt caatgctttt caagataccc agatcatatg   240
aagcggcacg acttcttcaa gagcgccatg cctgagggat acgtgcagga gaggaccatc   300
ttcttcaagg acgacgggaa ctacaagaca cgtgctgaag tcaagtttga gggagacacc   360
ctcgtcaaca ggatcgagct taagggaatc gatttcaagg aggacggaaa catcctcggc   420
cacaagttgg aatacaacta caactcccac aacgtataca tcatggcaga caaacaaaag   480
aatggaatca agttaacttc aaaattagac acaacattg aagatggaag cgttcaacta   540
gcagaccatt atcaacaaaa tactccaatt ggcgatggcc ctgtcctttt accagacaac   600
cattacctgt ccacacaatc tgccctttcg aaagatccca cgaaaagag agaccacatg   660 gtccttcttg agtttgtaac agctgctggg attacacatg gcatggatga actatacaaa   720
taatctaga                                                          729

<210> SEQ ID NO 44
<211> LENGTH: 27
<212> TYPE: DNA
<213> ORGANISM: Artificial sequence
<220> FEATURE:
<223> OTHER INFORMATION: Synthetic sequence: Primer

<400> SEQUENCE: 44
gggatccatg agtaaaggag aagaact                                      27

<210> SEQ ID NO 45
<211> LENGTH: 27
<212> TYPE: DNA
<213> ORGANISM: Artificial sequence
<220> FEATURE:
<223> OTHER INFORMATION: Synthetic sequence: Primer

<400> SEQUENCE: 45
ttctagatta tttgtatagt tcatcca                                      27

<210> SEQ ID NO 46
<211> LENGTH: 1527
<212> TYPE: DNA
<213> ORGANISM: Artificial sequence
<220> FEATURE:
<223> OTHER INFORMATION: Synthetic sequence: aadA - mGFP4 fusion sequence

<400> SEQUENCE: 46

| | |
|---|---|
| cccgggatga gggaagcggt gatcgccgaa gtatcgactc aactatcaga ggtagttggc | 60 |
| gtcatcgagc gccatctcga accgacgttg ctggccgtac atttgtacgg ctccgcagtg | 120 |
| gatggcggcc tgaagccaca cagtgatatt gatttgctgg ttacggtgac cgtaaggctt | 180 |
| gatgaaacaa cgcggcgagc tttgatcaac gaccttttgg aaacttcggc ttccctgga | 240 |
| gagagcgaga ttctccgcgc tgtagaagtc accattgttg tgcacgacga catcattccg | 300 |
| tggcgttatc cagctaagcg cgaactgcaa tttggagaat ggcagcgcaa tgacattctt | 360 |
| gcaggtatct tcgagccagc cacgatcgac attgatctgg ctatcttgct gacaaaagca | 420 |
| agagaacata gcgttgcctt ggtaggtcca gcggcggagg aactctttga tccggttcct | 480 |
| gaacaggatc tatttgaggc gctaaatgaa accttaacgc tatggaactc gccgcccgac | 540 |
| tgggctggcg atgagcgaaa tgtagtgctt acgttgtccc gcatttggta cagcgcagta | 600 |
| accggcaaaa tcgcgccgaa ggatgtcgct gccgactggg caatggagcg cctgccggcc | 660 |
| cagtatcagc ccgtcatact tgaagctaga caggcttatc ttggacaaga agaagatcgc | 720 |
| ttggcctcgc gcgcagatca gttggaagaa tttgtccact acgtgaaagg cgagatcacc | 780 |
| aaggtagtcg gcaaatcagg atccatgagt aaaggagaag aacttttcac tggagttgtc | 840 |
| ccaattcttg ttgaattaga tggtgatgtt aatgggcaca atttcttgt cagtggagag | 900 |
| ggtgaaggtg atgcaacata cggaaaactt acccttaaat ttatttgcac tactggaaaa | 960 |
| ctacctgttc catggccaac acttgtcact actttctctt atggtgttca atgcttttca | 1020 |
| agatacccag atcatatgaa gcggcacgac ttcttcaaga gcgccatgcc tgagggatac | 1080 |
| gtgcaggaga ggaccatctt cttcaaggac gacgggaact acaagacacg tgctgaagtc | 1140 |
| aagtttgagg gagacaccct cgtcaacagg atcgagctta agggaatcga tttcaaggag | 1200 |
| gacgaaaaca tcctcggcca caagttggaa tacaactaca actcccacaa cgtatacatc | 1260 |
| atggcagaca acaaaagaa tggaatcaaa gttaacttca aaattagaca caacattgaa | 1320 |
| gatggaagcg ttcaactagc agaccattat caacaaaata ctccaattgg cgatggccct | 1380 |
| gtccttttac cagacaacca ttacctgtcc acacaatctg ccctttcgaa agatcccaac | 1440 |
| gaaaagagag accacatggt ccttcttgag tttgtaacag ctgctgggat tacacatggc | 1500 |
| atggatgaac tatacaaata atctaga | 1527 |

<210> SEQ ID NO 47
<211> LENGTH: 401
<212> TYPE: DNA
<213> ORGANISM: Nicotiana tabacum

<400> SEQUENCE: 47

| | |
|---|---|
| tctagactgg cctagtctat aggaggtttt gaaaagaaag gagcaataat cattttcttg | 60 |
| ttctatcaag agggtgctat tgctcctttc tttttttctt tttatttatt tactagtatt | 120 |
| ttacttacat agactttttt gtttacatta tagaaaaaga aggagaggtt attttcttgc | 180 |
| atttattcat gattgagtat tctatttga ttttgtattt gtttaaattg tgaaatagaa | 240 |
| cttgtttctc ttcttgctaa tgttactata tcttttgat ttttttttc caaaaaaaa | 300 |
| atcaaatttt gacttcttct tatctcttat ctttgaatat ctcttatctt tgaaataata | 360 |
| atatcattga aataagaaag aagagctata ttcgaccgcg g | 401 |

```
<210> SEQ ID NO 48
<211> LENGTH: 29
<212> TYPE: DNA
<213> ORGANISM: Artificial sequence
<220> FEATURE:
<223> OTHER INFORMATION: Synthetic sequence: Primer

<400> SEQUENCE: 48
gtctagagat cttggcctag tctatagga                                29

<210> SEQ ID NO 49
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 49
gccgcggtcg aatatagctc ttctttctta                               30

<210> SEQ ID NO 50
<211> LENGTH: 371
<212> TYPE: DNA
<213> ORGANISM: Triticum aestivum

<400> SEQUENCE: 50
actagtcaaa taaattttgc atgtctactc ttgttagtag aataggaatc gttgagaaag    60 attttcatt tgaatcatgc aaaaaagttt tctttgtttt tagtttagta tagttattta   120
aagaatagat agaaataaga ttgcgtccaa taggatttga acctatacca aaggtttaga   180
agacctctgt cctatccatt agacaatgga cgcttttctt tcatattta ttctttctt    240 tattttttt tcttcttccg agaaaaaact gttagaccaa aactcttta ggaaatcaaa    300 aaatccagat acaaatgcat gatgtatata ttatatcatg catatatcat aaagaaggag   360
tatggaagct t                                                       371

<210> SEQ ID NO 51
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 51
gactagtcaa ataaattttg catgtctact c                             31

<210> SEQ ID NO 52
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 52
gaagctttcc atactccttc tttatgatat atg                           33

<210> SEQ ID NO 53
<211> LENGTH: 403
<212> TYPE: DNA
<213> ORGANISM: Arabidopsis thaliana

<400> SEQUENCE: 53
aagctttctc ataataaaaa aaatatgtta aattttgtta cgaatttttt cgaatacaga    60
```

| aaaaatcttc gatagcaaat taatcggtta attcaataaa aagtgggagt aagcactcga | 120 |
| tttcgttggt cccacccaag cggatgtgga attcaatttt ttattcattc aatgaaggaa | 180 |
| tagtcatttt caagctcaac taactgaaac ctagttttaa aataaaaaat atatgaataa | 240 |
| aaaaatttt tgcggaaagt cttttatttt tttatcataa taggaatagg caagcctttg | 300 |
| ttttatctag cgaattcgaa acggaacttt agttatgatt cattatttcg atctcattag | 360 |
| ccttttttt cgtatttca ttttagcata tccggttctc gag | 403 |

<210> SEQ ID NO 54
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 54

| cccaagcttt ctcataataa aaaaaatatg tta | 33 |

<210> SEQ ID NO 55
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 55

| ccgctcgaga accggatatg ctaaaatgaa aata | 34 |

<210> SEQ ID NO 56
<211> LENGTH: 431
<212> TYPE: DNA
<213> ORGANISM: Arabidopsis thaliana

<400> SEQUENCE: 56

| ccgcggatgc gtcccattta ttcatcccct tagcaacccc cccttgtttt tcattttcat | 60 |
| ggatgaattc cgcatattgt catatctagg atttacatat acaacagata ttactgtcaa | 120 |
| gagtgatttt attaatattt taattttaat attaaatatt tggatttata aaaagtcaaa | 180 |
| gattcaaaac ttgaaaaaga agtattaggt tgcgctatac atatgaaaga atatacaata | 240 |
| atgatgtatt tggcgaatca aatatcatgg tctaataaag aataattctg attagttgat | 300 |
| aattttgtga agattcctg tgaaaaaggt taattaaatc tattcctaat ttatgtcgag | 360 |
| tagaccttgt tgttttgttt tattgcaaga attctaaatt catgacttgt agggagggac | 420 |
| ttatgtctag a | 431 |

<210> SEQ ID NO 57
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 57

| tccccgcgga tgcgtcccat ttattcatcc ct | 32 |

<210> SEQ ID NO 58
<211> LENGTH: 29
<212> TYPE: DNA
<213> ORGANISM: Artificial sequence
<220> FEATURE:
<223> OTHER INFORMATION: Synthetic sequence: Primer

<400> SEQUENCE: 58

```
gctctagaca taagtccctc cctacaagt                                    29
```

<210> SEQ ID NO 59
<211> LENGTH: 651
<212> TYPE: DNA
<213> ORGANISM: Nicotiana tabacum

<400> SEQUENCE: 59

```
ggcgcgccga gacataactt tgggctttgt tgatttactg cgtgatgatt ttgttgaaca    60
agatcgaagt cgcggtattt atttcactca agattgggtc tctttaccag gtgttctacc   120
cgtggcttca ggaggtattc acgtttggca tatgcctgct ctgaccgaga tctttgggga   180
tgattccgta ctacagttcg gtggaggaac tttaggacat ccttgggta atgcgccagg    240
tgccgtagct aatcgagtag ctctagaagc atgtgtaaaa gctcgtaatg aaggacgtga   300
tcttgctcag gaaggtaatg aaattattcg cgaggcttgc aaatggagcc cggaactagc   360
tgctgcttgt gaagtatgga agagatcgt atttaatttt gcagcagtgg acgttttgga   420
taagtaaaaa cagtgacat agcagataa attagcagga aataaagaag gataaggaga   480
aagaactcaa gtaattatcc ttcgttctct taattgaatt gcaattaaac tcggcccaat   540
cttttactaa aaggattgag ccgaatacaa caaagattct attgcatata ttttgactaa   600
gtatatactt acctagatat acaagatttg aaatacaaaa tctagccgcg g            651
```

<210> SEQ ID NO 60
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 60

```
gggcgcgccg agacataact tgggctttg ttga                               34
```

<210> SEQ ID NO 61
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 61

```
ggccgcggct agatttgta tttcaaatct tgt                                33
```

<210> SEQ ID NO 62
<211> LENGTH: 658
<212> TYPE: DNA
<213> ORGANISM: Nicotiana tabacum

<400> SEQUENCE: 62

```
ctcgagaact aaatcaaaat ctaagactca aatctttcta ttgttgtctt ggatccacaa    60
ttaatcctac ggatccttag gattggtata ttcttttcta tcctgtagtt tgtagttcc   120
ctgaatcaag ccaagtatca cacctctttc tacccatcct gtatattgtc ccctttgttc   180
cgtgttgaaa tagaacctta atttattact tattttttta ttaaatttta gatttgttag   240
tgattagata ttagtattag acgagatttt acgaaacaat tatttttta tttctttata   300
ggagaggaca aatctctttt ttcgatgcga atttgacacg acataggaga agccgcccctt   360
```

```
tattaaaaat tatattattt taaataatat aaaggggggtt ccaacatatt aatatatagt    420
gaagtgttcc cccagattca gaactttttt tcaatactca caatccttat tagttaataa    480
tcctagtgat tggatttcta tgcttagtct gataggaaat aagatattca aataaataat    540
tttatagcga atgactattc atctattgta ttttcatgca aatagggggc aagaaaactc    600
tatggaaaga tggtggttta attcgatgtt gtttaagaag gagttcgaac gcactagt     658
```

<210> SEQ ID NO 63
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 63

```
ggactagtgc gttcgaactc cttcttaaac aac                                  33
```

<210> SEQ ID NO 64
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 64

```
ggctcgagaa ctaaatcaaa atctaagact ca                                   32
```

<210> SEQ ID NO 65
<211> LENGTH: 488
<212> TYPE: DNA
<213> ORGANISM: Lycopersicon esculentum

<400> SEQUENCE: 65

```
ggcgcgccgt ccgctagcac gtcgatcggt taattcaaaa aaatcggaat tagcactcga     60
tttcgttggc accatgcaat tgaaccaatc caattgttta cttattcaat gagactgagt    120
taatttggaa gctcacccaa cctatttcca tttaaaaatc tcaagtggat gaatcagaat    180
cttgagaaat tctttcattt gtctatcatt atagacaagc ccatccatat tatcgattct    240
atggaattcg aacctgaact ttattttcta tttctattac gattcattat ttgtatctaa    300
tgggctcctc ttcttatta tttttttattt aaatttcagc atatcgattt atgcctagcc    360
tattcttttc tttgcgtttt tctttctttt ttataccttt catagattca tagaggaatt    420
ccatatattt tcacatctag gatttacata tacaacatat accactgtca aggggggaagt    480 tcccgcgg                                                              488
```

<210> SEQ ID NO 66
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 66

```
gggcgcgccg tccgctagca cgtcgatcgg t                                    31
```

<210> SEQ ID NO 67
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 67
gccgcgggaa cttccccctt gacagtggta t                                    31

<210> SEQ ID NO 68
<211> LENGTH: 516
<212> TYPE: DNA
<213> ORGANISM: Lycopersicon esculentum

<400> SEQUENCE: 68
gtcgacaggg ggaagttctt attatttagg ttagctaggt atttccattt caaaaaaaaa     60
aaaggtaaaa aatcaaaatt gggttgcgct atatatga aagagtatac aataatgatg      120
tatttggcaa atcaaatacc atggtctaat aatcaaccat tctgattaat tgataatatt    180
agtattagtt ggaaattttg tgaaagattc ctgtgaaaag tttcattaac gcggaattca    240
tgtcgagtag accttgctgt tgtgagaatt cttaattcat gagttgtagg gagggattta    300
tgtcaccaca aacagagact aaagcaagtg ttggattcaa agctggtgtt aaagagtaca    360
aattgactta ttatactcct gagtaccaaa ccaaggatac tgatatattg gcagcattcc    420
gagtaactcc tcaacctgga gttccacctg aagaagcagg ggccgcggta gctgccgaat    480
cttctactgg tacatggaca actgtatgga gcatgc                              516

<210> SEQ ID NO 69
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 69
ggtcgacagg gggaagttct tattatttag gt                                   32

<210> SEQ ID NO 70
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 70
ggcatgctcc atacagttgt ccatgtacca gt                                   32

<210> SEQ ID NO 71
<211> LENGTH: 495
<212> TYPE: DNA
<213> ORGANISM: Oryza sativa

<400> SEQUENCE: 71
ggcgcgccct tgttgaataa tgccaaatca acaccaaaaa aatatccaaa aatccaaaag     60
tcaaaaggaa atgaattagt taattcaata agagagaaaa ggggaccagc acttgatttc    120
gttgcccaaa cgaatcccat tcaatcgttt actcatggaa tgagcccgtc ggaaagttca    180
atcaatcttt ttttcatata cattttgcct tttgtaaacg atttgtgcct actctacttt    240
cttatctagg acttcgatat acaaaatata tactactgtg aagcatagat tgctgtcaac    300
agagaatttt cgtagtattt aggtatttcc actcaaaata gaaaagggg gtctattaag    360 aacttaataa ggattagaag ttgatttggg gttgcgctat atctattaaa gagtatacaa    420
taaagatgga tttggtgaat caaatccatg gtttaataac gaagcatgtt aacttaccat    480
aacaacaaca agctt                                                        495

<210> SEQ ID NO 72
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 72
gggcgcgccc ttgttgaata atgccaaatc aa                                      32

<210> SEQ ID NO 73
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 73
gaagcttgtt gttgttatgg taagttaaca                                         30

<210> SEQ ID NO 74
<211> LENGTH: 508
<212> TYPE: DNA
<213> ORGANISM: Oryza sativa

<400> SEQUENCE: 74
ccgcggtcaa ttcttatcga attcctatag tagaattcct atagcataga atgtacacag        60
ggtgtaccca ttatatatga atgaaacata ttatatgaat gaaacatatt cattaactta       120
agcatgcccc ccatttctct taatgagttg atattaattg aatatctttt ttttaagatt       180
tttgcaaagg tttcatttac gcctaatcca tatcgagtag accctgtcgt tgtgagaatt       240
cttaattcat gagttgtagg gagggacgta tgtcaccaca aacagaaact aaagcaagtg       300
ttggattaa agctggtgtt aaggattata aattgactta ctacaccccg gagtacgaaa        360
ccaaggacac tgatatcttg gcagcattcc gagtaactcc tcagccgggg gttccgcccg       420
aagaagcagg ggctgcagta gctgccgaat cttctactgg tacatggaca actgtttgga       480
ctgatggact taccagtctt gagcatgc                                          508

<210> SEQ ID NO 75
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 75
gccgcggtca attcctatcg aattcctata gta                                     33

<210> SEQ ID NO 76
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 76
ggcatgctca agactggtaa gtccatcagt cc                                      32

<210> SEQ ID NO 77
<211> LENGTH: 1343

<212> TYPE: DNA
<213> ORGANISM: Artificial sequence
<220> FEATURE:
<223> OTHER INFORMATION: Synthetic sequence: 35S promoter based on NCBI
      data bank Accession number NC_001497

<400> SEQUENCE: 77

```
gaattccaat cccacaaaaa tctgagctta acagcacagt tgctcctctc agagcagaat      60
cgggtattca acaccctcat atcaactact acgttgtgta taacggtcca catgccggta     120
tatacgatga ctggggttgt acaaaggcgg caacaaacgg cgttcccgga gttgcacaca     180
agaaatttgc cactattaca gaggcaagag cagcagctga cgcgtacaca acaagtcagc     240
aaacagacag gttgaacttc atccccaaag gagaagctca actcaagccc aagagctttg     300
ctaaggccct aacaagccca ccaaagcaaa agcccactg gctcacgcta ggaaccaaaa      360
ggcccagcag tgatccagcc ccaaaagaga tctcctttgc cccggagatt acaatggacg     420
atttcctcta tctttacgat ctaggaagga agttcgaagg tgaagtagac gacactatgt     480
tcaccactga taatgagaag gttagcctct tcaatttcag aaagaatgct gacccacaga     540
tggttagaga ggcctacgca gcaggtctca tcaagacgat ctacccgagt aacaatctcc     600
aggagatcaa ataccttccc aagaaggtta agatgcagt caaaagattc aggactaatt     660
gcatcaagaa cacagagaaa gacatatttc tcaagatcag aagtactatt ccagtatgga     720
cgattcaagg cttgcttcat aaaccaaggc aagtaataga gattggagtc tctaaaaagg     780
tagttcctac tgaatctaag gccatgcatg gagtctaaga ttcaaatcga ggatctaaca     840
gaactcgccg tgaagactgg cgaacagttc atacagagtc ttttacgact caatgacaag     900
aagaaaatct tcgtcaacat ggtggagcac gacactctgg tctactccaa aaatgtcaaa     960
gatacagtct cagaagacca aagggctatt gagactttc aacaaggat aatttcggga     1020
aacctcctcg gattccattg cccagctatc tgtcacttca tcgaaggac agtagaaaag    1080
gaaggtggct cctacaaatg ccatcattgc gataaaggaa aggctatcat tcaagatctc    1140
tctgccgaca gtggtcccaa agatggaccc ccacccacga ggagcatcgt ggaaaaagaa    1200
gacgttccaa ccacgtcttc aaagcaagtg gattgatgtg acatctccac tgacgtaagg    1260
gatgacgcac aatcccacta tccttcgcaa gacccttcct ctatataagg aagttcattt    1320
catttggaga ggacacgctc gag                                            1343
```

<210> SEQ ID NO 78
<211> LENGTH: 1102
<212> TYPE: DNA
<213> ORGANISM: Arabidopsis thaliana

<400> SEQUENCE: 78

```
ggtaccatga tcgcttcatg tttttatcta atttgttagc atattgaatg attgattttc      60
ttttaatttg gatatgttga ttgtcttgtt gcatcatcaa tgtatgtttt atttaacacc     120
ggaagatctt atgatgggtt cattacttca taataatctc cgagttctac aagactacaa     180
ctttcacgtg acttttacag cgacaaaaaa tgcatctagc gaaaattaat ccacaaccta     240
tgcattttg tcactcttca cacgcgtatg tgcataaata tatagtatat actcgacaat     300
cgatgcgtat gtgtacacaa ttaccaaaac aattatttga atattcagac atgggttgac     360
atcaccaagt aatattcaca gtatctgaaa actatgtttt gacatcccta aatagtttga     420
ctaaccagtt taatatgaga gcatttgtaa gaggcaagag ccatggtttt gttggctcgt     480
ttaatatgct catttaaccc ccccaaaaaa tactattaga tttaaacgta aaagaattaa     540
```

-continued

```
cgaacacaag aactgctaaa acaaaaaaaa atcaatggcc gacatttcat agttcataca    600
tcactaatac taaagatgc atcatttcac tagggtctca tgaaatagga gttgacattt    660
ttttttgtaa cgacagaagt tgacatgtta agcatcaatt ttttaagag tggattatac    720 tagtttttt ttttttttt aatgtatggt atgatacaac aacaaaaact ataaaataga    780
aaaagtcagt gaaacctcaa attgaaggaa aaacttttgc acaaaagag agagagagag    840 aaagaatgta aatccaaata aatgggccta attgagaatg ctttaactt ttttttttgg    900 ctaaaagaga atgctttaac taagcccata aaatgaacat caaactcaaa gggtaagatt    960
aatacattta gaaacaata gccgaatatt taataagttt aagacataga ggagttttat   1020
gtaatttagg aaccgatcca tcgttggctg tataaaaagg ttacatctcc ggctaacata   1080
tcggcaaaaa aggaacctcg ag                                             1102
```

<210> SEQ ID NO 79
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 79
ccctctgtcg cactcatagc tacag                                            25

<210> SEQ ID NO 80
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 80
ggagatgttg tgcgagtatc gacagg                                           26

<210> SEQ ID NO 81
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 81
caaccattac ctgtccacac aatctgcc                                         28

<210> SEQ ID NO 82
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 82
gctgggatta cacatggcat ggatgaac                                         28

<210> SEQ ID NO 83
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 83

```
ataggtgaaa gtagtgacaa gtgttggc                                              28

<210> SEQ ID NO 84
<211> LENGTH: 27
<212> TYPE: DNA
<213> ORGANISM: Artificial sequence
<220> FEATURE:
<223> OTHER INFORMATION: Synthetic sequence: Primer

<400> SEQUENCE: 84
cgtatgttgc atcaccttca ccctctc                                               27

<210> SEQ ID NO 85
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 85
agagaattgg gcgttccgat cgtaa                                                 25

<210> SEQ ID NO 86
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 86
ggattcaccg caaatactag cttg                                                  24

<210> SEQ ID NO 87
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 87
gaaattccga atgtctttaa cgccga                                                26

<210> SEQ ID NO 88
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 88
tggaataact gtctccattc ctatcact                                              28

<210> SEQ ID NO 89
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 89
aaaggctaca tctagtaccg gac                                                   23

<210> SEQ ID NO 90
<211> LENGTH: 25
<212> TYPE: DNA
<213> ORGANISM: Artificial sequence
```

```
<220> FEATURE:
<223> OTHER INFORMATION: Synthetic sequence: Primer

<400> SEQUENCE: 90
ccagaagtag taggattgat tctca                                          25

<210> SEQ ID NO 91
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 91
cgatcaagac tggtaagtcc at                                             22

<210> SEQ ID NO 92
<211> LENGTH: 25
<212> TYPE: DNA
<213> ORGANISM: Artificial sequence
<220> FEATURE:
<223> OTHER INFORMATION: Synthetic sequence: Primer

<400> SEQUENCE: 92
acaatggaag taagcatatt ggtaa                                          25

<210> SEQ ID NO 93
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 93
gggtccaata atttgatcga ta                                             22

<210> SEQ ID NO 94
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 94
cgagaagtag taggattggt tctc                                           24

<210> SEQ ID NO 95
<211> LENGTH: 26
<212> TYPE: DNA
<213> ORGANISM: Artificial sequence
<220> FEATURE:
<223> OTHER INFORMATION: Synthetic sequence: Primer

<400> SEQUENCE: 95
gtctaatgga taagctacat aagcga                                         26

<210> SEQ ID NO 96
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 96
cccacaatgg aagtaaacat gt                                             22
```

<210> SEQ ID NO 97
<211> LENGTH: 931
<212> TYPE: DNA
<213> ORGANISM: Artificial sequence
<220> FEATURE:
<223> OTHER INFORMATION: Synthetic sequence: Optimised L1.LtrB intron

<400> SEQUENCE: 97

| acacatccat aacgtgcgcc cagatagggt gttaagtcaa gtagtttaag gtactactca | 60 |
| gtaagataac actgaaaaca gccaacctaa ccgaaaagcg aaagctgata cgggaacaga | 120 |
| gcacggttgg aaagcgatga gttagctaaa gacaatcggc tacgactgag tcgcaatgtt | 180 |
| aatcagatat aagctataag ttgtgtttac tgaacgcaag tttctaattt cggttatgtg | 240 |
| tcgatagagg aaagtgtctg aaacctctag tacaaagaaa gctaagttat ggttgtggac | 300 |
| ttagctgtta tcaccacatt tgtacaatct gttggagaac caatgggaac gaaacgaaag | 360 |
| cgatggcgag aatctgaatt taccaagact aacactaac tggggatagc ctaaacaaga | 420 |
| atgcctaata gaaggagga aaaggctat agcactagag cttgaaaatc ttgcaaggct | 480 |
| acggagtagt cgtagtagtc tgagaaggct aacggccttt acatggcaaa gggctacagt | 540 |
| tattgtgtac taaaattaaa aattgattag ggaggaaaac ctcaaaatga aaccaacaat | 600 |
| ggcaatttta gaaagaatca gtaaaaattc acaagaaaat atagacgaag tttttacaag | 660 |
| actttatcgt tatcttttac gtcctgatat ttattacgtg gcgggcgcgc cacgcgtgcg | 720 |
| gccgctggga aatggcaatg atagcgaaag aacctaaaac tctggttcta tgctttcatt | 780 |
| gtcatcgtca cgtgattcat aaacacaagt gaatttttac gaacgaacaa taacagagcc | 840 |
| gtatactccg agagggtac gtacggttcc cgaagagggt ggtgcaaacc agtcacagta | 900 |
| atgtgaacaa ggcggtacct ccctacttca c | 931 |

<210> SEQ ID NO 98
<211> LENGTH: 2140
<212> TYPE: DNA
<213> ORGANISM: Artificial sequence
<220> FEATURE:
<223> OTHER INFORMATION: Synthetic sequence: Synthetic LtrA gene
      optimised for plant transformation (LtrASi)

<400> SEQUENCE: 98

| atgaagccaa caatggcaat cctcgaacga atctctaaga actcacagga gaacatcgac | 60 |
| gaggtcttca caagacttta ccgttacctt ctccgtcctg acatctacta cgtggcatat | 120 |
| cagaacctct actctaacaa gggagcttct acaaagggaa tcctcgatga tacagctgat | 180 |
| ggattctctg aggagaagat caagaagatc atccaatctt tgaaggacgg aacttactac | 240 |
| cctcagcctt ccgaagaat gtacatcgca aagaagaact ctaagaagat gagacctctt | 300 |
| ggaatcccaa ctttcacaga caagttgatc caggaggctg tgagaatcat ccttgaatct | 360 |
| atctatgagc ctgtcttcga ggatgtgtct cacggtttcc gacctcagcg aagctgtcac | 420 |
| acagctttga agacaatcaa gagagagttc ggaggtgcaa gatggttcgt ggagggagat | 480 |
| atcaagggat gcttcgataa catcgaccac gtcacactca tcggactcat caaccttaag | 540 |
| atcaaggata tgaagatgag ccagttgatc tacaagttcc tcaaggcagg tacctttatc | 600 |
| ctcgatcctc gcactctcac tatctgtaga catgttattg aaaaaccta tctccgatta | 660 |
| ttagtttttct gattttcatt tcattttgac gccgattcac ataggttacc tcgaaaactg | 720 |
| gcagtaccac aagacttaca gcggaacacc tcaggcggga tcctctctc ctctcctcgc | 780 |

```
taacatctat cttcatgaat tggacaagtt cgttctccaa ctcaagatga agttcgaccg   840
agagagtcca gagagaatca cacctgaata ccgggagctt cacaacgaga tcaaaagaat   900
ctctcaccgt ctcaagaagt tggagggcga ggagaaggct aaggttctct tggaatacca   960
ggagaagagg aagaggttgc ctacactccc ttgtacatca caaacaaaca aggttcgttc  1020
tctccatttt cattcgtttg agtctgattt agtgttttgt ggttgatctg aatcgattta  1080
ttgttgatta gtgaatcaat ttgaggctgt gtcctaatgt tttgacttt  gattacaggt  1140 cttgaagtac gtccgatacg ctgacgactt catcatctct gttaagggaa gcaaggagga  1200
ctgtcaatgg atcaaggagc aattgaagct cttcatccat aacaagctca agatggaatt  1260
gagtgaggag aagacactca tcacacatag cagtcagcct gctcgtttcc tcggatacga  1320
catccgagtc aggagaagtg gaactatcaa gcgatctgga aaggtcaaga agagaacact  1380
caacgggagt gtggagcttc tcatccctct ccaagacaag atccgtcaat tcatcttcga  1440
caagaagatc gctatccaga agaaggatag ctcatggttc ccagttcaca ggaagtacct  1500
tatccgttca acagacttgg agatcatcac aatctacaac tctgaattga gaggtaagct  1560
gctacctcaa actttctagt gcttccatat ttcctttctt ctgcaaggca gagaaccatt  1620
gtggttaagt gttttaaatt gtgaatgtat aggtatctgc aactactacg gtctcgcaag  1680
taacttcaac cagctcaact acttcgctta ccttatggaa tactcttgct tgaagactat  1740
cgcatctaag cataagggaa cactctcaaa gaccatctct atgttcaagg atggaagtgg  1800
ttcttgggga atcccttacg agatcaagca ggggaagcag aggagatact tcgccaactt  1860
cagtgaatgc aaatctcctt accaattcac tgatgagatc agtcaagctc ctgtgcttta  1920
cggatacgct cggaacactc ttgagaacag acttaaggct aagtgttgtg agctttgtgg  1980
aacatctgat gagaacacat cttacgagat ccaccacgtc aacaaggtca agaaccttaa  2040
gggaaaggag aagtgggaga tggcaatgat cgctaagcag cggaagactc ttgttgtttg  2100
cttccattgt catcgtcacg tgatccataa gcacaagtga                        2140
```

<210> SEQ ID NO 99
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 99
atctacaagt tcctcaaggc aggtaccttt atcctcgatc ctcg                       44

<210> SEQ ID NO 100
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 100
tactgccagt tttcgaggta acctatgtga atcggcgtca aaat                       44

<210> SEQ ID NO 101
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 101
ttgtacatca caaacaaaca aggttcgttc tctccatttt catt                44

<210> SEQ ID NO 102
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 102
cgtatcggac gtacttcaag acctgtaatc aaaagtcaaa acat                44

<210> SEQ ID NO 103
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 103
atctacaact ctgaattgag aggtaagctg ctacctcaaa cttt                44

<210> SEQ ID NO 104
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 104
agaccgtagt agttgcagat acctatacat tcacaattta aaac                44

<210> SEQ ID NO 105
<211> LENGTH: 22
<212> TYPE: DNA
<213> ORGANISM: Artificial sequence
<220> FEATURE:
<223> OTHER INFORMATION: Synthetic sequence: Primer

<400> SEQUENCE: 105
gcatgcatga agccaacaat gg                                        22

<210> SEQ ID NO 106
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 106
cgaggatcga ggataaaggt acctgccttg aggaacttgt agat                44

<210> SEQ ID NO 107
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 107
attttgacgc cgattcacat aggttacctc gaaaactggc agta                44

<210> SEQ ID NO 108
<211> LENGTH: 44
<212> TYPE: DNA

```
<210> SEQ ID NO 108
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 108
aatgaaaatg gagagaacga accttgtttg tttgtgatgt acaa             44

<210> SEQ ID NO 109
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 109
atgttttgac ttttgattac aggtcttgaa gtacgtccga tacg             44

<210> SEQ ID NO 110
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 110
aaagtttgag gtagcagctt acctctcaat tcagagttgt agat             44

<210> SEQ ID NO 111
<211> LENGTH: 44
<212> TYPE: DNA
<213> ORGANISM: Artificial sequence
<220> FEATURE:
<223> OTHER INFORMATION: Synthetic sequence: Primer

<400> SEQUENCE: 111
gttttaaatt gtgaatgtat aggtatctgc aactactacg gtct             44

<210> SEQ ID NO 112
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 112
ttactagttc acttgtgctt atgg                                   24

<210> SEQ ID NO 113
<211> LENGTH: 2331
<212> TYPE: DNA
<213> ORGANISM: Artificial sequence
<220> FEATURE:
<223> OTHER INFORMATION: Synthetic sequence: aadA - mGFP fusion
      optimised for transformation

<400> SEQUENCE: 113
atggcagaag cggtgatcgc cgaagtatcg actcaactat cagaggtaag taacttttag    60
ctctcagctg ctgtttacta agttcatgcc atacattgat tctggtttat taagggttat   120
gttcagtatt actagtaaca aaatctattt cttcgtttcc gtctgcaggt agttggcgtc   180
atcgagcgcc atctcgaacc gacgttgctg gccgtacatt tgtacggctc cgcagtggat   240
ggcggcctga agccacacag tgatattgat ttgctggtta cggtgaccgt aaggcttgat   300
gaaacaacgc ggcgagcttt gatcaacgac cttttggaaa cttcggcttc ccctggagag   360
```

```
agcgagattc tccgcgctgt agaggtaatt ttcatctttg tttggccttc caagtgcttt    420
ttttgctgtt tacgggtgga acttcagtaa aaatgggatc aaaacatcat atggcataaa    480
taaattttaa gaatggcgaa ctcggggtta ccgaatatgg cttccttttt cagtgtttct    540
tagtccattg tacttatgag attgcaggtc accattgttg tgcacgacga catcattccg    600
tggcgttatc cagctaagcg cgaactgcaa tttggagaat ggcagcgcaa tgacattctt    660
gcaggtatct tcgagccagc cacgatcgac attgatctgg ctatcttgct gacaaaagca    720
agagaacata gcgttgcctt ggtaggtcca gcggcggagg aactctttga tccggttcct    780
gaacaggatc tatttgaggc gctaaatgaa accttaacgc tatggaactc gccgcccgac    840
tgggcaggta agaaatcttt tcccatcttg aagtcacctc aaaccgaacg ttaggaaatt    900
ccaaaatgtt ttgatagtag tctacttagt ttcaagtttt gggtttgtgt atactttcac    960
taataatatg cgtggaaaca ttgcaggtga tgagcgaaat gtagtgctta cgttgtcccg   1020
catttggtac agcgcagtaa ccggcaaaat cgcgccgaag gatgtcgctg ccgactgggc   1080
aatggagcgc ctgccggccc agtatcagcc cgtcatactt gaagctagac aggcttatct   1140
tggacaagaa gaagatcgct tggcctcgcg cgcagatcag ttggaagaat ttgtccacta   1200
cgtgaaaggc gagatcacca aggtagtcgg caaatcagga tccatggcta gcaaaggaga   1260
agaactttc actggagttg tcccaattct tgttgaatta gatggtgatg ttaatgggca   1320
caaattttct gtcagtggag agggtgaagg taattaaaca aaatttaaac atctatataa   1380
actagctaga tcttaggaaa atttggttta atatattagg atcttgattt atataaacat   1440
gttcaaaatg ttatctgagt ggtttgtaac atgtggtttg tataggtgat gctacatacg   1500
gaaaacttac ccttaaattt atttgcacta ctggaaaact acctgttcct tggccaacac   1560
ttgtcactac tttctcttat ggtgttcaat gcttttcccg ttatccggat cagatgaaac   1620
ggcatgactt tttcaagagt gccatgcccg aaggttatgt acaggaacgc actatatctt   1680
tcaaagatga cgggaactac aagacgcgtg ctgaagtcaa gtttgaaggt aagtaaatat   1740
tggtaatata acattttac atgactttgg tgtcttaatt tgtcgtttcg catgtgtttc   1800
atttagtttc tgccagagca tctgagaggc cattcttaat atatgatatg atgttgcttt   1860
gctctaggtg ataccttgt taatcgtatc gagttgaaag gaatcgactt caaggaagat   1920
ggaaacatcc tcggacacaa gctggagtac aactacaact cacacaacgt gtacatcacc   1980
gcagacaaac agaagaatgg aatcaaagct aacttcaaaa ttcgccacaa cattgaagat   2040
ggttccgttc aactagcaga ccattatcaa caaaatactc caataggtac gcaggctata   2100
taggctttga catttttttg ttttcatatt tttctttgtt ccactatgaa cttcattctg   2160
tttttttgact tcattgcagg tgatggcccct gtccttttac cagacaacca ttacctgtcg   2220
acacaatctg cccttttcgaa agatcccaac gaaaagcgag accacatggt ccttcttgag   2280
tttgtaacag ctgctgggat tacacatggc atggatgagc tctacaaata a            2331
```

<210> SEQ ID NO 114
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 114

```
actatcagag gtaagtaact tttagctctc a                                    31
```

```
<210> SEQ ID NO 115
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 115
cgccaactac ctgcagacgg aaacgaagaa                                    30

<210> SEQ ID NO 116
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 116
cgctgtagag gtaattttca tctttgtttg gcct                               34

<210> SEQ ID NO 117
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 117
caatggtgac ctgcaatctc ataagtacaa tg                                 32

<210> SEQ ID NO 118
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 118
gactgggcag gtaagaaatc ttttcccatc ttga                               34

<210> SEQ ID NO 119
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 119
cgctcatcac ctgcaatgtt tccacgcata t                                  31

<210> SEQ ID NO 120
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 120
gagggtgaag gtaatttatt cttctttgtt ttc                                33

<210> SEQ ID NO 121
<211> LENGTH: 33
<212> TYPE: DNA
<213> ORGANISM: Artificial sequence
<220> FEATURE:
<223> OTHER INFORMATION: Synthetic sequence: Primer
```

<400> SEQUENCE: 121
gtagcatcac ctgtttaaga agaaaatcaa aat                              33

<210> SEQ ID NO 122
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 122
aagtttgaag gtaagtaaat attggtaata taac                             34

<210> SEQ ID NO 123
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 123
agggtatcac ctagagcaaa gcaacatcat atc                              33

<210> SEQ ID NO 124
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 124
tactccaata ggtacgcagg ctatataggc tttg                             34

<210> SEQ ID NO 125
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 125
agggccatca cctgcaatga agtcaaaaaa cag                              33

<210> SEQ ID NO 126
<211> LENGTH: 50
<212> TYPE: DNA
<213> ORGANISM: Artificial sequence
<220> FEATURE:
<223> OTHER INFORMATION: Synthetic sequence: Primer

<400> SEQUENCE: 126
atacaagtga gttgtaggga gggaatcatg gcagaagcgg tgatcgccga             50

<210> SEQ ID NO 127
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 127
aagttactta cctctgatag ttgagtcgat a                                31

<210> SEQ ID NO 128
<211> LENGTH: 33

<212> TYPE: DNA
<213> ORGANISM: Artificial sequence
<220> FEATURE:
<223> OTHER INFORMATION: Synthetic sequence: Primer

<400> SEQUENCE: 128
ccgtctgcag gtagttggcg tcatcgagcg cca                              33

<210> SEQ ID NO 129
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 129
gatgaaaatt acctctacag cgcggagaat ct                               32

<210> SEQ ID NO 130
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 130
gagattgcag gtcaccattg ttgtgcacga c                                31

<210> SEQ ID NO 131
<211> LENGTH: 30
<212> TYPE: DNA
<213> ORGANISM: Artificial sequence
<220> FEATURE:
<223> OTHER INFORMATION: Synthetic sequence: Primer

<400> SEQUENCE: 131
agatttctta cctgcccagt cgggcggcga                                  30

<210> SEQ ID NO 132
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 132
aaacattgca ggtgatgagc gaaatgtagt gct                              33

<210> SEQ ID NO 133
<211> LENGTH: 24
<212> TYPE: DNA
<213> ORGANISM: Artificial sequence
<220> FEATURE:
<223> OTHER INFORMATION: Synthetic sequence: Primer

<400> SEQUENCE: 133
tcctgatttg ccgactacct tggt                                        24

<210> SEQ ID NO 134
<211> LENGTH: 27
<212> TYPE: DNA
<213> ORGANISM: Artificial sequence
<220> FEATURE:
<223> OTHER INFORMATION: Synthetic sequence: Primer

<400> SEQUENCE: 134
gggatccatg agtaaaggag aagaact                                              27

<210> SEQ ID NO 135
<211> LENGTH: 45
<212> TYPE: DNA
<213> ORGANISM: Artificial sequence
<220> FEATURE:
<223> OTHER INFORMATION: Synthetic sequence: Primer

<400> SEQUENCE: 135
aaaatttaga acagatattg accttcaccc tctccactga cagaa                          45

<210> SEQ ID NO 136
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 136
ttcttaaaca ggtgatgcta catacggaaa ac                                        32

<210> SEQ ID NO 137
<211> LENGTH: 31
<212> TYPE: DNA
<213> ORGANISM: Artificial sequence
<220> FEATURE:
<223> OTHER INFORMATION: Synthetic sequence: Primer

<400> SEQUENCE: 137
atttacttac cttcaaactt gacttcagca c                                         31

<210> SEQ ID NO 138
<211> LENGTH: 32
<212> TYPE: DNA
<213> ORGANISM: Artificial sequence
<220> FEATURE:
<223> OTHER INFORMATION: Synthetic sequence: Primer

<400> SEQUENCE: 138
ctttgctcta ggtgataccc ttgttaatcg ta                                        32

<210> SEQ ID NO 139
<211> LENGTH: 35
<212> TYPE: DNA
<213> ORGANISM: Artificial sequence
<220> FEATURE:
<223> OTHER INFORMATION: Synthetic sequence: Primer

<400> SEQUENCE: 139
agcctgcgta cctattggag tattttgttg ataat                                     35

<210> SEQ ID NO 140
<211> LENGTH: 33
<212> TYPE: DNA
<213> ORGANISM: Artificial sequence
<220> FEATURE:
<223> OTHER INFORMATION: Synthetic sequence: Primer

<400> SEQUENCE: 140
ttcattgcag gtgatggccc tgtcctttta cca                                       33

<210> SEQ ID NO 141
<211> LENGTH: 27
<212> TYPE: DNA
<213> ORGANISM: Artificial sequence
<220> FEATURE:
<223> OTHER INFORMATION: Synthetic sequence: Primer

<400> SEQUENCE: 141
ttctagatta tttgtatagt tcatcca                                          27

<210> SEQ ID NO 142
<211> LENGTH: 1845
<212> TYPE: DNA
<213> ORGANISM: Nicotiana tabacum

<400> SEQUENCE: 142

| | | | | | |
|---|---|---|---|---|---|
| atgtcagaaa | aggtgaagaa | tggtataatt | cctaactttg | ttactattcc | ttctacttct | 60 |
| aacaatccca | caagtgcaga | agtacgacc | gacgaggttt | ccgagcaggg | ggagcaacct | 120 |
| ggtgaggtta | ttgagcaggg | ggagcaactt | gatgaaggtg | tcgaggaagt | ggagcacccc | 180 |
| actcagggag | aagaacaaca | tcaacctctg | aggagatcag | agaggccaag | ggtagagtca | 240 |
| cgcaggtacc | cttccacaga | gtatgtcctc | atcagtgatg | aggggagcc | agaaagtctt | 300 |
| aaggaggtgt | tgtcccatcc | agaaaagaac | cagtggatga | agctatgca | agaagagatg | 360 |
| gaatctctcc | agaaaaatgg | cacatacaag | ctggttgaac | ttccaaaggg | taaaagacca | 420 |
| ctcaaatgca | aatgggtctt | taaactcaag | aaagatggag | atggcaagct | ggtcagatac | 480 |
| aaagctcgat | tggtggttaa | aggcttcgaa | cagaagaaag | gtattgattt | tgacgaaatt | 540 |
| ttctccccg | ttgttaaaat | gacttctatt | cgaacaattt | tgagcttagc | agctagccta | 600 |
| gatcttgaag | tggagcagtt | ggatgtgaaa | actgcatttc | ttcatggaga | tttggaagag | 660 |
| gagatttata | tggagcaacc | agaaggattt | gaagtagctg | gaaagaaaca | catggtgtgc | 720 |
| aaattgaata | gagtctttta | tggattgaag | caggcaccaa | ggcagtggta | catgaagttt | 780 |
| gattcattca | tgaaaagtca | aacataccta | agacctatt | ctgatccatg | tgtatacttc | 840 |
| aaaagattt | ctgagaataa | ctttattata | ttgttgttgt | atgtggatga | catgctaatt | 900 |
| gtaggaaaag | acaagggt | gatagcaaag | ttgaaaggag | atctgtccaa | gtcatttgat | 960 |
| atgaaggact | tgggcccagc | acaacaaatt | ctagggatga | agatagttcg | agagagaaca | 1020 |
| agtagaaagt | tgtggctatc | tcaggagaag | tacattgaac | gtgtactaga | acgcttcaac | 1080 |
| atgaagaatg | ctaagccagt | cagcacacct | cttgctggtc | atctaaagtt | gagtaaaaag | 1140 |
| atgtgtccta | caacagtgga | agagaaaggg | aacatggcta | agttccctta | ttcttcagca | 1200 |
| gtcggaagct | tgatgtatgc | aatggtatgt | actagacctg | atattgctca | cgcagttggt | 1260 |
| gttgtcagca | ggtttcttga | aaatcctgga | aggaacatt | gggaagcagt | caagtggata | 1320 |
| ctcaggtacc | tgagaggtac | cacgggagat | tgtttgtgct | ttggaggatc | tgatccaatc | 1380 |
| ttgaagggct | atacagatgc | tgatatggca | ggtgacattg | acaacagaaa | atccagtact | 1440 |
| ggatatttgt | ttacattttc | aggggagct | atatcatggc | agtctaagtt | gcaaaagtgc | 1500 |
| gttgcacttt | caacaactga | agcagagtac | attgctgcta | cagaaactgg | caaggagatg | 1560 |
| atatggctca | agcgattcct | tcaagagctt | ggattgcatc | agaaggagta | tgtcgtctat | 1620 |
| tgtgacagtc | aaagtgcaat | agaccttagc | aagaactcta | tgtaccatgc | aaggaccaaa | 1680 |
| cacattgatg | tgagatatca | ttggattcga | gaaatggtag | atgatgaatc | tctaaaagtc | 1740 |
| ttgaagattt | ctacaaatga | gaatcccgca | gatatgctga | ccaaggtggt | accaaggaac | 1800 |
| aagttcgagc | tatgcaaaga | acttgtcgga | atgcattcaa | actag | | 1845 |

<210> SEQ ID NO 143

```
<211> LENGTH: 23
<212> TYPE: DNA
<213> ORGANISM: Artificial sequence
<220> FEATURE:
<223> OTHER INFORMATION: Synthetic sequence: Primer

<400> SEQUENCE: 143
ggcatgcatg tcagaaaagg tga                                            23

<210> SEQ ID NO 144
<211> LENGTH: 35
<212> TYPE: DNA
<213> ORGANISM: Artificial sequence
<220> FEATURE:
<223> OTHER INFORMATION: Synthetic sequence: Primer

<400> SEQUENCE: 144
gactagtcta gtttgaatgc attccgacaa gttct                               35

<210> SEQ ID NO 145
<211> LENGTH: 180
<212> TYPE: DNA
<213> ORGANISM: Nicotiana tabacum

<400> SEQUENCE: 145
atggcttcct cagttctttc ctctgcagca gttgccaccc gcagcaatgt tgctcaagct    60
aacatggttg cacctttcac tggccttaag tcagctgcct cattccctgt ttcaaggaag   120
caaaaccttg acatcacttc cattgccagc aatggtggaa gagtgcaatg tatgcaggta   180

<210> SEQ ID NO 146
<211> LENGTH: 34
<212> TYPE: DNA
<213> ORGANISM: Artificial sequence
<220> FEATURE:
<223> OTHER INFORMATION: Synthetic sequence: Primer

<400> SEQUENCE: 146
gctcgagaca atggcttcct cagttctttc ctct                                34

<210> SEQ ID NO 147
<211> LENGTH: 36
<212> TYPE: DNA
<213> ORGANISM: Artificial sequence
<220> FEATURE:
<223> OTHER INFORMATION: Synthetic sequence: Primer

<400> SEQUENCE: 147
cgcatgctac ctgcatacat tgcactcttc caccat                              36

<210> SEQ ID NO 148
<211> LENGTH: 12
<212> TYPE: DNA
<213> ORGANISM: Artificial sequence
<220> FEATURE:
<223> OTHER INFORMATION: Synthetic sequence: Primer binding site (PBS)
      sequence

<400> SEQUENCE: 148
ttggtaccta ct                                                        12

<210> SEQ ID NO 149
<211> LENGTH: 38
<212> TYPE: DNA
<213> ORGANISM: Artificial sequence
<220> FEATURE:
```

<223> OTHER INFORMATION: Synthetic sequence: Primer

<400> SEQUENCE: 149

| gccgcagtag gtaccaattg cccttctccg accctgac | 38 |

<210> SEQ ID NO 150
<211> LENGTH: 1751
<212> TYPE: DNA
<213> ORGANISM: Arabidopsis thaliana

<400> SEQUENCE: 150

| cggtacctac cggatttgga gccaagtctc ataaacgcca ttgtggaaga aagtcttgag | 60 |
| ttggtggtaa tgtaacagag tagtaagaac agagaagaga gagagtgtga gatacatgaa | 120 |
| ttgtcgggca acaaaaatcc tgaacatctt attttagcaa agagaaagag ttccgagtct | 180 |
| gtagcagaag agtgaggaga aatttaagct cttggacttg tgaattgttc cgcctcttga | 240 |
| atacttcttc aatcctcata tattcttctt ctatgttacc tgaaaacgg catttaatct | 300 |
| cgcgggttta ttccggttca acattttttt tgttttgagt tattatctgg cttaataac | 360 |
| gcaggcctga aataaattca aggcccaact gtttttttt taagaagtt gctgttaaaa | 420 |
| aaaaaaaaag ggaattaaca acaacaacaa aaaagataa agaaataat aacaattact | 480 |
| ttaattgtag actaaaaaaa catagatttt atcatgaaaa aagagaaaa gaaataaaaa | 540 |
| cttggatcaa aaaaaaaaca tacagatctt ctaattatta acttttctta aaaattaggt | 600 |
| ccttttccc aacaattagg tttagagttt tggaattaaa ccaaaaagat tgttctaaaa | 660 |
| aatactcaaa tttggtagat aagtttcctt attttaatta gtcaatggta gatacttttt | 720 |
| tttcttttct ttattagagt agattagaat cttttatgcc aagtattgat aaattaaatc | 780 |
| aagaagataa actatcataa tcaacatgaa attaaaagaa aaatctcata tatagtatta | 840 |
| gtattctcta tatatattat gattgcttat tcttaatggg ttgggttaac caagacatag | 900 |
| tcttaatgga aagaatcttt tttgaacttt ttccttattg attaaattct tctatagaaa | 960 |
| agaaagaaat tatttgagga aaagtatata caaaagaaa aatagaaaaa tgtcagtgaa | 1020 |
| gcagatgtaa tggatgacct aatccaacca ccaccatagg atgtttctac ttgagtcggt | 1080 |
| cttttaaaaa cgcacggtgg aaaatatgac acgtatcata tgattccttc ctttagtttc | 1140 |
| gtgataataa tcctcaactg atatcttcct ttttttgttt tggctaaaga tattttattc | 1200 |
| tcattaatag aaaagacggt tttgggcttt tggtttgcga tataaagaag accttcgtgt | 1260 |
| ggaagataat aattcatcct ttcgtctttt tctgactctt caatctctcc caaagcctaa | 1320 |
| agcgatctct gcaaatctct cgcgactctc tctttcaagg tatattttct gattcttttt | 1380 |
| gttttttgatt cgtatctgat ctccaatttt tgttatgtgg attattgaat cttttgtata | 1440 |
| aattgcttt gacaatattg ttcgtttcgt caatccagct tctaaatttt gtcctgatta | 1500 |
| ctaagatatc gattcgtagt gtttacatct gtgtaatttc ttgcttgatt gtgaaattag | 1560 |
| gattttcaag gacgatctat tcaattttg tgttttcttt gttcgattct ctctgtttta | 1620 |
| ggtttcttat gtttagatcc gtttctcttt ggtgttgttt tgatttctct tacggctttt | 1680 |
| gatttggtat atgttcgctg attggtttct acttgttcta ttgttttatt tcaggtcacc | 1740 |
| aaacactcga g | 1751 |

<210> SEQ ID NO 151
<211> LENGTH: 28
<212> TYPE: DNA
<213> ORGANISM: Artificial sequence

```
<220> FEATURE:
<223> OTHER INFORMATION: Synthetic sequence: Primer

<400> SEQUENCE: 151
cggtacctac cggatttgga gccaagtc                                              28

<210> SEQ ID NO 152
<211> LENGTH: 42
<212> TYPE: DNA
<213> ORGANISM: Artificial sequence
<220> FEATURE:
<223> OTHER INFORMATION: Synthetic sequence: Primer

<400> SEQUENCE: 152
gctcgagtgt ttggtgacct gaaataaaac aatagaacaa gt                              42

<210> SEQ ID NO 153
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 153
ggtaccatga tcgcttcatg tttttatc                                              28

<210> SEQ ID NO 154
<211> LENGTH: 28
<212> TYPE: DNA
<213> ORGANISM: Artificial sequence
<220> FEATURE:
<223> OTHER INFORMATION: Synthetic sequence: Primer

<400> SEQUENCE: 154
ctcgaggttc ctttttgcc gatatgtt                                               28

<210> SEQ ID NO 155
<211> LENGTH: 10
<212> TYPE: DNA
<213> ORGANISM: Artificial sequence
<220> FEATURE:
<223> OTHER INFORMATION: Synthetic sequence: Consensus near the
      transcription initiation site of NEP promoters

<400> SEQUENCE: 155
atagaataaa                                                                  10
```